(12) United States Patent
Hu et al.

(10) Patent No.: US 6,685,632 B1
(45) Date of Patent: Feb. 3, 2004

(54) SURGICAL INSTRUMENTS FOR ACCESSING AND STABILIZING A LOCALIZED PORTION OF A BEATING HEART

(75) Inventors: Lawrence W. Hu, Santa Clara, CA (US); David J. Paul, Scotts Valley, CA (US); Eugene Edward Reis, San Jose, CA (US); Harry Leonard II Green, Santa Cruz, CA (US); Joshua K. Wallin, Cupertino, CA (US); Dwight P. Morejohn, Davis, CA (US); Charles S. Taylor, San Francisco, CA (US); Gary B. Weller, Los Gatos, CA (US); Richard M. Ferrari, Saratoga, CA (US)

(73) Assignee: Cardiothoracic Systems, Inc., Santa Clara, CA (US)

( * ) Notice: Subject to any disclaimer, the term of this patent is extended or adjusted under 35 U.S.C. 154(b) by 0 days.

(21) Appl. No.: 09/958,263

(22) PCT Filed: May 4, 2000

(86) PCT No.: PCT/US00/12239
§ 371 (c)(1),
(2), (4) Date: Mar. 6, 2002

(87) PCT Pub. No.: WO00/66008
PCT Pub. Date: Nov. 9, 2000

Related U.S. Application Data

(63) Continuation-in-part of application No. 09/372,661, filed on May 4, 1999, now abandoned, and a continuation-in-part of application No. 09/305,803, filed on May 4, 1999, now Pat. No. 6,231,506, and a continuation-in-part of application No. 09/305,810, filed on May 4, 1999, now Pat. No. 6,331,158, and a continuation-in-part of application No. 09/305,811, filed on May 4, 1999, now Pat. No. 6,283,912, and a continuation-in-part of application No. 09/305,813, filed on May 4, 1999, now Pat. No. 6,290,644, which is a continuation-in-part of application No. 09/305,810, filed on May 4, 1999, now Pat. No. 6,331,158.

(51) Int. Cl.$^7$ ............................................. A61B 17/00
(52) U.S. Cl. ..................... 600/234; 600/231; 600/232; 600/235
(58) Field of Search ................................ 600/201, 210, 600/226, 227, 228, 229, 235, 234

(56) References Cited

U.S. PATENT DOCUMENTS

| 452,131 A | 5/1891 | Haughawout |
| 810,675 A | 1/1906 | Richter |
| 1,706,500 A | 3/1929 | Smith |

(List continued on next page.)

FOREIGN PATENT DOCUMENTS

| DE | 90 04513 | 6/1990 |

(List continued on next page.)

OTHER PUBLICATIONS

U.S. patent application Ser. No. 09/345,859 Looney et al. filed on Jul. 1, 1999.

(List continued on next page.)

Primary Examiner—Cary E. O'Connor
(74) Attorney, Agent, or Firm—Law Office of Alan W. Cannon

(57) ABSTRACT

Surgical devices for stabilizing the heart which facilitate anastomosis under beating heart conditions. Various instruments or devices may be maneuvered and secured on a retractor device to provide stabilization of the heart. An instrument mount is provided which is preferably configured to accept a surgical instrument, such as a tissue stabilizer, and to allow the instrument to be easily maneuvered to a desired position and subsequently locked into position. Stabilizer devices each having at least one surface for contacting the heart and each being adapted to be mounted to the retractor while having the ability to be positioned in the desired location against the heart are provided.

82 Claims, 37 Drawing Sheets

U.S. PATENT DOCUMENTS

| | | |
|---|---|---|
| 2,296,793 A | 9/1942 | Kirschbaum |
| 2,590,527 A | 3/1952 | Fluck |
| 2,693,795 A | 11/1954 | Grieshaber |
| 2,863,444 A | 12/1958 | Winsten |
| 3,392,722 A | 7/1968 | Jorgensen |
| 3,683,926 A | 8/1972 | Suzuki |
| 3,720,433 A | 3/1973 | Rosfelder |
| 3,783,373 A | 1/1974 | Jocobs |
| 3,783,873 A | 1/1974 | Jacobs |
| 3,858,926 A | 1/1975 | Ottenhues |
| 3,882,855 A | 5/1975 | Schulte et al. |
| 3,882,885 A | 5/1975 | Schulte et al. |
| 3,983,863 A | 10/1976 | Janke et al. |
| 4,047,532 A | 9/1977 | Phillips et al. |
| 4,048,987 A | 9/1977 | Hurson |
| 4,049,000 A | 9/1977 | Williams |
| 4,049,002 A | 9/1977 | Kletschka et al. |
| 4,052,980 A | 10/1977 | Grams et al. |
| 4,226,228 A | 10/1980 | Shin et al. |
| 4,230,119 A | 10/1980 | Blum |
| 4,306,561 A | 12/1981 | de Medinaceli |
| 4,366,819 A | 1/1983 | Kaster |
| 4,368,736 A | 1/1983 | Kaster |
| 4,421,107 A | 12/1983 | Estes et al. |
| 4,428,368 A | 1/1984 | Torii |
| 4,434,791 A | 3/1984 | Darnell |
| 4,461,284 A | 7/1984 | Fackler |
| 4,492,229 A | 1/1985 | Grunwald |
| 4,617,916 A | 10/1986 | Le Vahn et al. |
| 4,627,421 A | 12/1986 | Symbas et al. |
| 4,637,377 A | 1/1987 | Loop |
| 4,646,747 A | 3/1987 | Lundback |
| 4,688,570 A | 8/1987 | Kramer et al. |
| 4,702,230 A | 10/1987 | Pelta |
| 4,718,418 A | 1/1988 | L=Esperance, Jr. |
| 4,726,356 A | 2/1988 | Santilli et al. |
| 4,726,358 A | 2/1988 | Brady |
| 4,736,749 A | 4/1988 | Lundback |
| 4,747,394 A | 5/1988 | Wananabe |
| 4,747,395 A | 5/1988 | Brief |
| 4,754,746 A | 7/1988 | Cox |
| 4,803,984 A | 2/1989 | Narayanan et al. |
| 4,808,163 A | 2/1989 | Laub |
| 4,829,985 A | 5/1989 | Couetil |
| 4,852,552 A | 8/1989 | Chaux |
| 4,854,318 A | 8/1989 | Solem et al. |
| 4,863,133 A | 9/1989 | Bonnell |
| 4,865,019 A | 9/1989 | Phillips |
| 4,884,559 A | 12/1989 | Collins |
| 4,925,443 A | 5/1990 | Heilman et al. |
| 4,949,707 A | 8/1990 | LeVahn et al. |
| 4,955,896 A | 9/1990 | Freeman |
| 4,962,758 A | 10/1990 | Lasner et al. |
| 4,971,037 A | 11/1990 | Pelta |
| 4,973,300 A | 11/1990 | Wright |
| 4,989,587 A | 2/1991 | Farley |
| 4,991,578 A | 2/1991 | Cohen |
| 4,993,862 A | 2/1991 | Pelta |
| 5,009,660 A | 4/1991 | Clapham |
| 5,011,469 A | 4/1991 | Buckberg et al. |
| 5,025,779 A | 6/1991 | Bugge |
| 5,036,868 A | 8/1991 | Berggren et al. |
| 5,037,428 A | 8/1991 | Picha et al. |
| 5,052,373 A | 10/1991 | Michelson |
| 5,053,041 A | 10/1991 | Ansari et al. |
| 5,080,088 A | 1/1992 | LeVahn |
| 5,098,369 A | 3/1992 | Heilman et al. |
| 5,102,853 A | 4/1992 | Chattha et al. |
| 5,119,804 A | 6/1992 | Anstadt |
| 5,131,905 A | 7/1992 | Grooters et al. |
| 5,133,724 A | 7/1992 | Wilson, Jr. et al. |
| 5,159,921 A | 11/1992 | Hoover |
| RE34,150 E | 12/1992 | Santilli et al. |
| 5,167,223 A | 12/1992 | Koros et al. |
| 5,171,254 A | 12/1992 | Sher |
| 5,231,974 A | 8/1993 | Giglio et al. |
| 5,287,861 A | 2/1994 | Wilk |
| 5,293,863 A | 3/1994 | Zhu et al. |
| 5,300,087 A | 4/1994 | Knoepfler |
| 5,318,013 A | 6/1994 | Wilk |
| 5,336,252 A | 8/1994 | Cohen |
| 5,382,256 A | 1/1995 | Del Castillo |
| 5,382,756 A | 1/1995 | Dagan |
| 5,383,840 A | 1/1995 | Heiman et al. |
| 5,417,709 A | 5/1995 | Slater |
| 5,437,651 A | 8/1995 | Todd et al. |
| 5,452,733 A | 9/1995 | Sterman et al. |
| 5,467,763 A | 11/1995 | McMahon et al. |
| 5,498,256 A | 3/1996 | Furnish |
| 5,503,617 A | 4/1996 | Jako |
| 5,509,890 A | 4/1996 | Kazama |
| 5,512,037 A | 4/1996 | Russell et al. |
| 5,514,075 A | 5/1996 | Moll et al. |
| 5,514,076 A | 5/1996 | Ley |
| 5,520,610 A | 5/1996 | Giglio et al. |
| 5,529,571 A | 6/1996 | Daniel |
| 5,547,458 A | 8/1996 | Ortiz et al. |
| 5,573,496 A | 11/1996 | McPherson et al. |
| 5,582,580 A | 12/1996 | Buckman, Jr. et al. |
| 5,607,421 A | 3/1997 | Jeevanandam et al. |
| 5,607,446 A | 3/1997 | Beehler et al. |
| 5,613,937 A | 3/1997 | Garrison et al. |
| 5,616,117 A | 4/1997 | Dinkler et al. |
| 5,651,378 A | 7/1997 | Matheny et al. |
| 5,727,569 A | 3/1998 | Benetti et al. |
| 5,730,757 A | 3/1998 | Benetti et al. |
| 5,749,892 A | 5/1998 | Vierra et al. |
| 5,755,660 A | 5/1998 | Tyagi |
| 5,772,583 A | 6/1998 | Wright et al. |
| 5,782,746 A | 7/1998 | Wright |
| 5,795,291 A | 8/1998 | Koros et al. |
| 5,799,661 A | 9/1998 | Boyd et al. |
| 5,807,243 A | 9/1998 | Vierra et al. |
| 5,813,410 A | 9/1998 | Levin |
| 5,836,311 A | 11/1998 | Borst et al. |
| 5,846,187 A | 12/1998 | Wells et al. |
| 5,846,193 A | 12/1998 | Wright |
| 5,846,194 A | 12/1998 | Wasson et al. |
| 5,865,730 A | 2/1999 | Fox et al. |
| 5,868,770 A | 2/1999 | Rygaard |
| 5,875,782 A | 3/1999 | Ferrari et al. |
| 5,876,332 A | 3/1999 | Looney |
| 5,879,291 A | 3/1999 | Kolata et al. |
| 5,882,299 A | 3/1999 | Rastegar et al. |
| 5,885,271 A | 3/1999 | Hamilton et al. |
| 5,888,247 A | 3/1999 | Benetti |
| 5,891,017 A | 4/1999 | Swindle et al. |
| 5,894,843 A | 4/1999 | Benetti et al. |
| 5,906,602 A | 5/1999 | Taylor et al. |
| 5,906,607 A | 5/1999 | Taylor et al. |
| 5,908,382 A | 6/1999 | Koros et al. |
| 5,913,876 A | 6/1999 | Taylor et al. |
| 5,927,284 A | 7/1999 | Borst et al. |
| 5,944,658 A | 8/1999 | Koros et al. |
| 5,944,736 A | 8/1999 | Taylor et al. |
| 5,947,125 A | 9/1999 | Benetti |
| 5,947,896 A | 9/1999 | Sherts et al. |
| 5,957,835 A | 9/1999 | Anderson et al. |
| 5,967,972 A | 10/1999 | Santilli et al. |

| | | | |
|---|---|---|---|
| 5,976,080 A | 11/1999 | Farascioni | |
| 5,976,171 A | 11/1999 | Taylor | |
| 5,984,865 A | 11/1999 | Farley et al. | |
| 5,984,867 A | 11/1999 | Deckman et al. | |
| 6,007,486 A | 12/1999 | Hunt et al. | |
| 6,017,304 A | 1/2000 | Vierra et al. | |
| 6,019,722 A | 2/2000 | Spence et al. | |
| 6,030,340 A | 2/2000 | Maffei et al. | |
| D421,803 S | 3/2000 | Koros et al. | |
| 6,032,672 A | 3/2000 | Taylor | |
| 6,033,362 A | 3/2000 | Cohn | |
| 6,036,641 A | 3/2000 | Taylor et al. | |
| 6,050,266 A | 4/2000 | Benetti et al. | |
| 6,063,021 A | 5/2000 | Hossain et al. | |
| 6,071,295 A | 6/2000 | Takahashi | |
| 6,099,468 A | 8/2000 | Santilli et al. | |
| 6,102,854 A | 8/2000 | Carfier et al. | |
| 6,139,492 A | 10/2000 | Vierra et al. | |
| 6,183,486 B1 | 2/2001 | Snow et al. | |
| 6,190,311 B1 | 2/2001 | Glines et al. | |
| 6,193,652 B1 | 2/2001 | Berky et al. | |
| 6,200,263 B1 | 3/2001 | Person | |
| 6,210,323 B1 | 4/2001 | Gilhuly et al. | |
| 6,213,940 B1 | 4/2001 | Sherts et al. | |
| 6,213,941 B1 | 4/2001 | Benetti et al. | |
| 6,231,506 B1 | 5/2001 | Hu et al. | |
| 6,283,912 B1 | 9/2001 | Hu et al. | |
| 6,290,644 B1 | 9/2001 | Green, II et al. | |
| 6,315,717 B1 | 11/2001 | Benetti et al. | |
| 6,331,157 B2 | 12/2001 | Hancock | |
| 6,331,158 B1 | 12/2001 | Hu et al. | |
| 6,346,077 B1 | 2/2002 | Taylor et al. | |
| 6,348,036 B1 | 2/2002 | Looney et al. | |
| 6,394,951 B1 | 5/2002 | Taylor et al. | |

FOREIGN PATENT DOCUMENTS

| | | |
|---|---|---|
| EP | 0 293 760 A3 | 12/1988 |
| EP | 0 293 760 B1 | 12/1988 |
| EP | 0 293 760 A2 | 12/1988 |
| EP | 0 630 629 | 5/1994 |
| EP | 668 058 A1 | 8/1995 |
| EP | 0 993 806 A2 | 4/2000 |
| EP | 0 803 228 A1 | 10/2000 |
| FR | 473451 | 1/1915 |
| GB | 168216 | 9/1921 |
| GB | 2 233 561 A | 1/1991 |
| GB | 2 267 827 A | 12/1993 |
| WO | WO 87/04081 | 7/1987 |
| WO | WO 94/14383 | 7/1994 |
| WO | WO 94/18881 | 9/1994 |
| WO | WO 95/01757 | 1/1995 |
| WO | WO 95/15715 | 6/1995 |
| WO | WO 95/17127 | 6/1995 |
| WO | WO 96/00033 | 1/1996 |
| WO | WO 97/10753 | 3/1997 |
| WO | WO 97/32514 A3 | 9/1997 |
| WO | WO 97/32514 A2 | 9/1997 |
| WO | WO 97/40752 | 11/1997 |
| WO | WO 98/27869 | 7/1998 |
| WO | WO 99/16367 * | 9/1998 |
| WO | WO 98/48703 | 11/1998 |
| WO | WO 98/49947 | 11/1998 |
| WO | WO 99/08585 | 2/1999 |
| WO | WO 99/09892 | 3/1999 |
| WO | WO 99/16367 | 4/1999 |
| WO | WO 00/06041 | 2/2000 |
| WO | WO 00/10466 | 3/2000 |
| WO | WO 00/16367 | 3/2000 |
| WO | WO 00/2000 | 7/2000 |
| WO | WO/42920 | 7/2000 |
| WO | WO 00/42921 | 7/2000 |
| WO | WO 00/42935 | 7/2000 |
| WO | WO 00/42936 | 7/2000 |
| WO | WO 00/42937 | 7/2000 |

OTHER PUBLICATIONS

U.S. patent application Ser. No. 09/438,670 Parsons, et al. filed on Nov. 12, 1999.

U.S. patent application Ser. No. 09/489,274 Brown et al. filed on Jan. 21, 2000.

U.S. patent application Ser. No. 60/117,333 Looney et al. (provisional) filed on Jan. 24, 1999.

Akins, et al., "*Preservation of Interventricular Septal Function in Patients Having Coronary Artery Bypass Graft Without Cardiopulmonary Bypass,*" American Heart Journal, vol. 107, No. 2, Feb., 1984, pp. 304–309.

Ancalmo, N. and J. L. Ochsner: "*A Modified Sternal Retractor,*" Ann. Thorac, Surg. 21 (1976) 174.

Angelini, G.D., M.D. et al., "*Fiber–Optic Retractor for Harvesting the Internal Mammary Artery,*" Ann. Thorac. Surg. (1990; 50:314–5).

Angelini, G.D., M.D., "*Simple, Inexpensive Method of Heart Retraction During Coronary Artery Bypass Surgery,*" Ann. Thora. Surg 46:46–247, Aug 1988.

Anstadt, M.D., et al., *Direct Mechanical Ventricular Actuation for Cardiac Arrest in Humans,* @ Chest, vol. 100, no. 1, Jul. 1991.

Antinori, C. et al., "*A Method of Retraction During Reoperative Coronary Operations Using the Favaloro Retractor,*" The Society of Thoracic Surgeons: 1989.

Archer, DO, et al., "*Coronary Artery Revascularization Without Cardiopulmonary Bypass.*" Texas Heart Institute Journal , vol. 11, no. 1, Mar. 1984, pp. 52–57.

Arom, J.V., et al., "Mini–Sternotomy for Coronary Artery Bypass Grafting," The Annals of Thoracic Surgery 1996;61:1271–2.

Arom, K.V. et al., "Mini–Sternotomy for Corony Artery Bypass Grafting," The Annals of Thoracic Surgery 1996; 62:1884–85.

Ballantyne, M.D., et al., "*Delayed Recovery of Severely "Stunned" Myocardium With the Support of a Left Ventricular Assist Device After Coronary Artery Bypass Graft Surgery,*" Journal of the American College of Cardiology, vol. 10, no. 3, Sep. 1987, pgs 710–712.

Bedellino, M.M., et al., "*The Cardiac Rag—Simple Exposure of the Heart,*" Texas Heart Institute Journal, vol. 15, no. 2, 1988, 134–35.

Beg, R.A., et al., "*Internal Mammary Retractor,*" Ann Thorac, Surg., vol. 39, no. 1, pp. 286–287, Jan. 1985.

Benetti, et al., "*Direct Coronary Surgery with Saphenous Vein Bypass Without Either Cardiopulmonary Bypass or Cardiac Arrest,*" The Journal of Cardiovascular Surgery, vol. 26, no. 3, May–Jun., 1985, pp. 217–222.

Benetti, et al., "*Direct Myocardial Revascularization Without Extracorporeal Circulation,*" Chest, vol. 100, no. 2 Aug., 1991, pgs 312–316.

Benetti, J., et al., "*A Single Coronary Artery Bypass Grafting—A Comparison Between Minimally Invasive Off Pump Techniques and Conventional Procedures,*" European Journal of Cardio–Thoracic Surgery, 14 (Suppl. I) (1998) S7–S12.

Borst, et al., "*Coronary Artery Bypass Grafting Without Cardiopulmonary Bypass and Without Interruption of native Coronary Flow Using a Novel Anastomosis Site Restraining Device ("Octopus"),*" J Am Coll Cardiol, May 1996, vol. 27, no. 6, pp. 1356–64.

Borst, et al., "*Regional Cardiac Wall Immunobilization for Open Chest and Closed Chest Coronary Artery Bypass Grafting on the Beating Heart: The 'Octopus' Method,*" Circulation, Oct. 15, 1995, vol. 92, no. 8, Supplement 1, 1–177.

British Heart Journal, "Coronary Surgery Without Cardiopulmonary Bypass," pp. 203–205, 1995.

Buffolo, et al., "*Direct Myocardial Revascularization Without Cardiopulmonary Bypass,*" Thoac. Cardiovas. Surgeon, 33 (1985) pp. 26–29.

Bugge, M., "*A New Internal Mammary Artery Retractor,*" Thorac. Cardiovasc Surgeon 38, pp. 316–17 (1990).

Calafiore, A.M., et al., "*Minimally Invasive Coronary Artery Bypass Grafting,*" The Annals of Thoracic Surgery, 62:1545–8, 1996.

Campalani et al., "A New Self–Retaining Internal mammary Artery Retractor." *J. Cardiovas. Surg.,* vol. 28. (1987).

Cartier, R, MD., "*Triple Coronary Artery Revascularization on the Stabilized Beating Heart: Initial Experience,*" Montreal Heart Institute, CJS, vol. 41, No. 4, pp. 283–288, Aug. 1998.

Chaux, A. and C. Blanche, "*A New Concept in Sternal Retraction: Applications for Internal Mammary Artery Dissection and Valve Replacement Surgery,*" Ann. Thorac. Surg. 42, pp. 473–474, Oct. 1986.

Cooley, D.A., "*Limited Access Myocardial Revascularization,*" Texas Heart Institute Journal, pp. 81–84, vol. 23, no. 2, 1996.

*Correspondence and Brief Communications,* Archives of Surgery—Volume 115, 1136–37, Sep. 1980.

Cremer, J, MD, "*Off–Bypass Coronary Bypass Grafting Via Minithoracotomy Using Mechanical Epicardial Stabilization,*" The Annals Of Thoracic Surgery, 63:S79–83, 1997.

Delacroix–Chevalier Surgical Instruments, IMA Saving Packages Brochure.

DelRossi, A J and Lemole, GM, "*A New Retractor to Aid in Coronary Artery Surgery,*" The Annals of Thoracic Surgery, vol. 36, No. 1, 101–102, Jul. 1983.

Fanning, MD., "*Reoperative Coronary Artery Bypass Grafting Without Cardiopulmonary Bypass,*" The Annals of Thoracic Surgery, vol. 55, no. 2, Feb. 1993, pp. 486–489.

Favaloro, M.D., et al, "*Direct Myocardial Revascularization by Saphenous Vein Graft,*" The Annals of Thoracic Surgery, vol. 10, no. 2, Aug. 1970.

Fonger, et al., "*Enhanced Preservation of Actuely Ischemic Myocardium with Transeptal Left Ventricular Assist,*" The Annals of Thoracic Surgery, vol. 57, no. 3, Mar. 1994, pp. 570–575.

Gacioch, et al., "*Cardiogenic Shock Complicating Acute Myocardial Infarction: The Use of Coronary Angioplasty and the Integration of the New Support Device into Patient Management,*" Journal of the American College of Cardiology, vol. 19, no. 3, Mar. 1, 1992.

Green, GE., "*Technique of Internal Mammary–Coronary Artery Anastomosis,*" The Journal of Cardiovascular Surgery, 78:455–79, 1979.

Groopman, J., "*Heart Surgery, Unplugged: Making the Coronary Bypass Safer, Chepaer, and Easier,*" The New Yorker, Jan. 11, 1999, pp. 43–46, 50–51.

Guzman, F. M.D., "*Transient Radial Nerve Injury Related to the Use of A Self Retraining Retractor for Internal Mammary Artery Dissection,*" J. Cardiovasc. Surg. 30, 1989, pp. 1015–1016.

Hasan, RI, et al., "*Technique of Dissecting the Internal Mammary After Using the Moussalli Bar,*" Euopean Journal of Cardiothoracic Surgery, 4:571–572, 1990.

Itoh, Toshiaki, M.D., et al., "*New Modification of a Mammary Artery Retractor,*" Ann. Thorac. Surg. 9, 1994; 57:1670–1.

Izzat, FRCS, et al., "*Cardiac Stabilizer for Minimally Invasive Direct Coronary Artey Bypass,*" Elsvier Science Inc., 1997 by the Society of Thoracic Surgeons.

Japanese Article "*Heart Retractor*"

Japanese Journal of Thoracic Surgery, vol. 42, no. 2, 1989.

Kazama, S. et al., "*Fabric Heart Retractor for Coronary Artery Bypass Operations,*" The Annals of Thoracic Surgery, 55:1582–3, 1993.

Kolessov, M.D., "*Mammary Artery–Coronary Artery Anastomosis as Method of Treatment for Angina Pectoris,*" Thoracic and Cardiovascular Surgery, vol. 54, no. 4, Oct., 1967, pp. 535–544.

Konishi, T. MD, et al., "*Hybrid–Type Stabilizer for Off–Pump Direct Coronary Artery Bypass Grafting,*" Annals of Thoracic Surgery 66:961–2, 1998.

Kresh, et al., "*Heart–Mechanical Assist Device Interaction,*" Trans. Am. Soc. Artif. Intern. Organs, vol. XXXII, 1986, pp. 437–443.

Lavergne, et al., "*Transcatheter Radio Frequency Ablation of A Trial Tissue Using A Suction Catheter,*" PACE, vol. 12, Jan. 1989, Part II, pp. 177–186.

Lonn, M.D., et al. "*Coronary Artery Operation Supported by the Hemopump: An Experimental Study on Pigs,*" The Annals of Thoracic Surgery, vol. 58, no. 1, Jul. 1994, pp. 516–523.

Matsuura, A. MD, et al., "*A New Device for Exposing the Cricumflex Coronary Artery*" The Annals of Thoracic Surgery, 59:1249–50, 1995, pp. 1249–1250.

McGee, et al., "*Extended Clinical Support with an Implantable Left Ventricular Assist Device,*" Trans. Am Soc. Artif. Intern. Organs, vol. XXXV, 1989, pp. 614–616.

McKeown, P.P. et al., "*A Modified Sternal Retractor for Exposure of the Internal Mammary Artery,*" Ann. Thorac. Surg. 32 (1981) 619.

Oschsner, JL, et al., "*Surgical Management of Diseased Intracavitary Coronary Arteries,*" The Annals of Thoracic Surgery, vol. 38, No. 4, Jul., pp. 356–62, Oct. 1984.

Parsonnet, V. MD, et al., "*Graduated probes for Coronary Bypass Surgery,*" The Journal of Thoracic and Cardiovascular Surgery, vol. 68, No. 3, 424–26 (Sept. 1974).

Parsonnet, V. MD, et al., "*Self–Retaining Epicardial Retractor for Aortocoronary Bypass Surgery,*" The Journal of Thoracic and Cardiovascular Surgery, 629–30 1979.

Perrault, L. et al., "*Snaring of the Target Vessel in Less Invasive Bypass Operations Does Not Cause Endothelial Dysfunction,*" The Society of Thoracic Surgeons, pp. 751–755, 1997.

Pfister, et al., "*Coronary Artery Bypass Without Cardiopulmonary Bypass,*" The Annals of Thoracic Surgery, vol. 54, no. 6, Dec. 1992, pp. 1085–1092.

Phillips, Steven J., M.D., "*A Versatile Retractor for Use in Harvesting the Internal Mammary Artery and Peforming Standard Cardiac Operations,*" J. Thorac. Cardiovasc. Surg. (1989; 97:633–5).

Pilling Surgical Instruments, A Rusch International Company Brochure.

Pittman, John, M.D., et al., "*Improved Visualization of the Internal Mammary Artery with a New Retractor System,*" Ann. Thorac. Surg., 1989; 48:869–70.

Riahi, et al., "*A Simple Technique and Device to Provide a Bloodless Operative Field in Coronary Artery Surgery Without Cross–Clamping the Aorta,*" The Journal of Thoracic and Cardiovascular Surgery, vol. 66, no. 6., Dec. 1973, pp. 974–78.

Richenbacher, M.D., et al., "*Current Status of Cardiac Surgery: A 40–Year Review,*" Journal of American College of Cardiology, vol. 14, no. 3, pp. 535–544.

Robicsek, F., "*Aortic Spoon–Jaw Clamp for Aorta–Saphenous Vein Anastomosis,*" Journal of Cardiac Surgery, 10:583–585, 1995.

Robinson, et al., "*A Minimally Invasive Surgical Method for Coronary Revascularization—Preliminary Experience in Five Patients,*" Circulation, Oct. 15, 1995, vol. 92, no. 8, 1–176.

Rousou, J. et al., "*Cardiac Retractor for Coronary Bypass Operations,*" The Society of Thoracic Surgeons, pp. 52:877–78, 1991.

Roux, D. MD. et al., "*New Helper Instrument in Cardiac Surgery,*" The Annals of Thoracic Surgery, 48: 595–6, 1989.

Roux, D., M.D. et al., "*Internal Mammary Artery Dissection: A Three Dimensional Sternal Retractor,*" J. Cardiovasc. Surg., 1989; 30:996–7.

Ruzevich et al. "*Long–Term Follow–up Survivors of Postcardiotomy Circulatory Support,*" Trans Am. Soc. Artif. Intern. Organs, vol. XXXIV, 1988, pp. 116–124.

Scholz, et al. "*Transfemoral Placement of the Left Ventricular Assist Device "Hemopump" During Mechanical Resuscitation,*" Thoracic and Cardiovascular Surgeon, vol. 38 (1990) pp. 69–72.

Stevens, et al., "*Closed Chest Coronary Artery Bypass With Cardioplegic Arrest in the Dog,*" $67^{th}$ Scientific Session, 238, I–251.

Trapp and R. Bisarya, "*To Use or Not to Use the Pump Oxygenator in Coronary Bypass Operatios,*" The Annals of Thoracic Surgery, vol. 19, no. 1, Jan. 1975, pp. 108–109.

Trapp, et al., "*Placement of Coronary Artery Bypass Graft without Pump Oxygenator,*" Journal of the Society of Thoracic Surgeons and The Southern Thoracic Surgeons Assn. vol. 19, no. 1, Jan. 1975.

USSC Cardiovascular Thora–Lift J, United States Surgical Corporation, Norwalk, Connecticut, Product Brochure.

Vigano, M., "*Tecnica Operatoria,*" Minerva Cardioangiologica, vol. 23–N. 6–7 (1975).

Vincent, J.G., "*A Compact Single Post Internal Mammary Artery Dissection Retractor,*" Eur. J. Cardio–Thor. Surg. 3 (1989) 276–277.

Westaby, S. et al., "*Less invasive Coronary Surgery: Consensus From the Oxford Meeting,*" The Annals of Thoracic Surgery, 62:924–31, 1996.

Zumbro, et al., *AA Prospective Evaluation of the Pulsatile Assist Device,* @ The Annals of Thoracic Surgery, vol. 28, no. 2, Aug., 1979, pp. 269–273.

\* cited by examiner

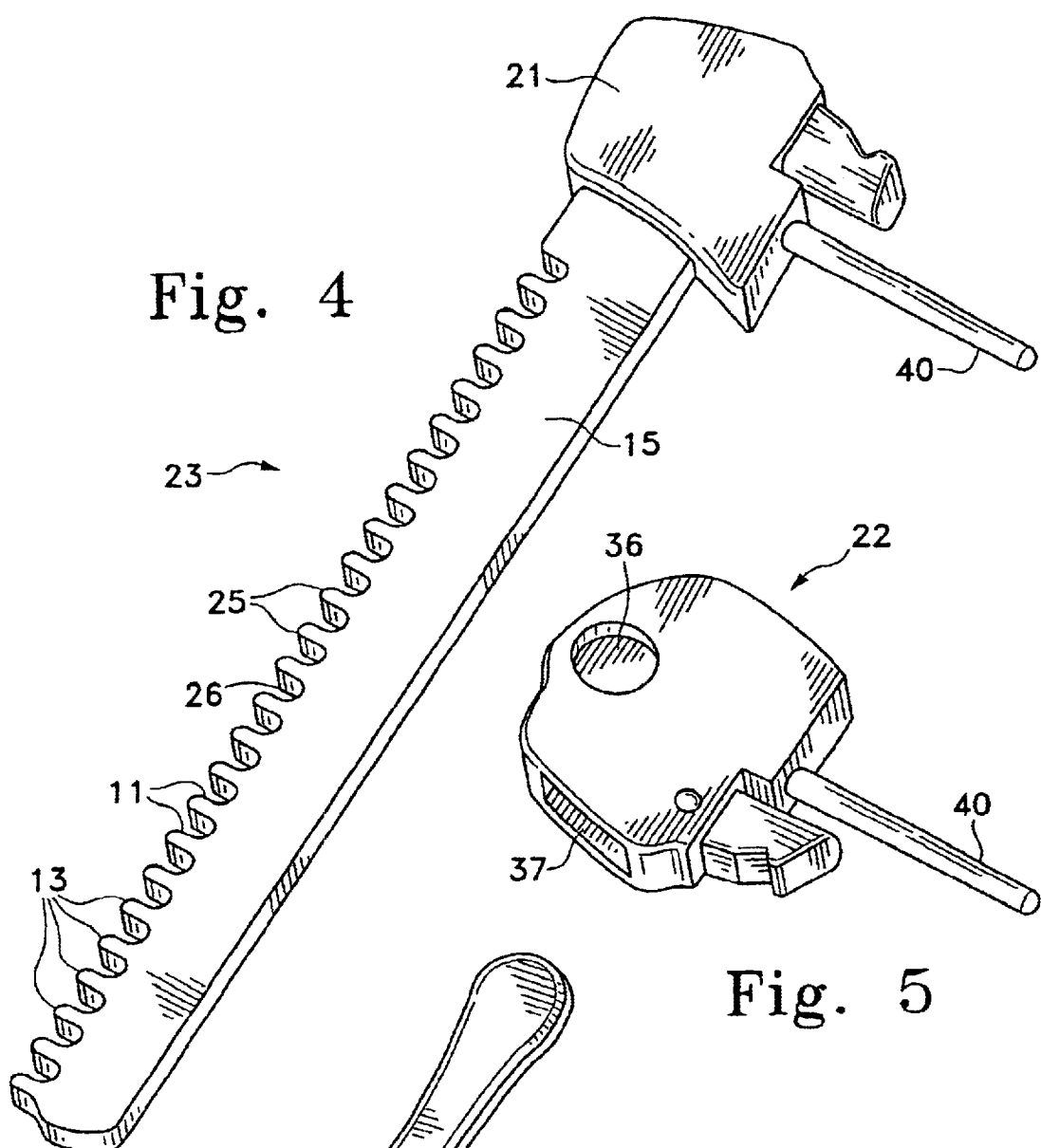
Fig. 4
Fig. 5
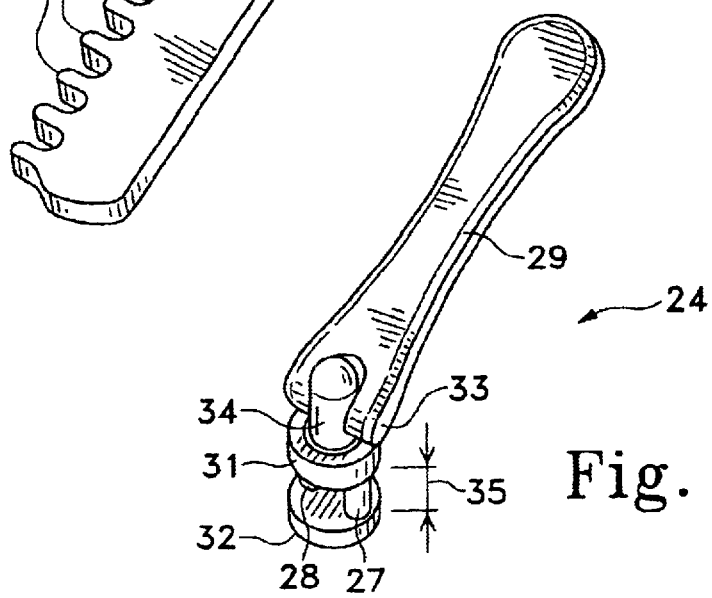
Fig. 6

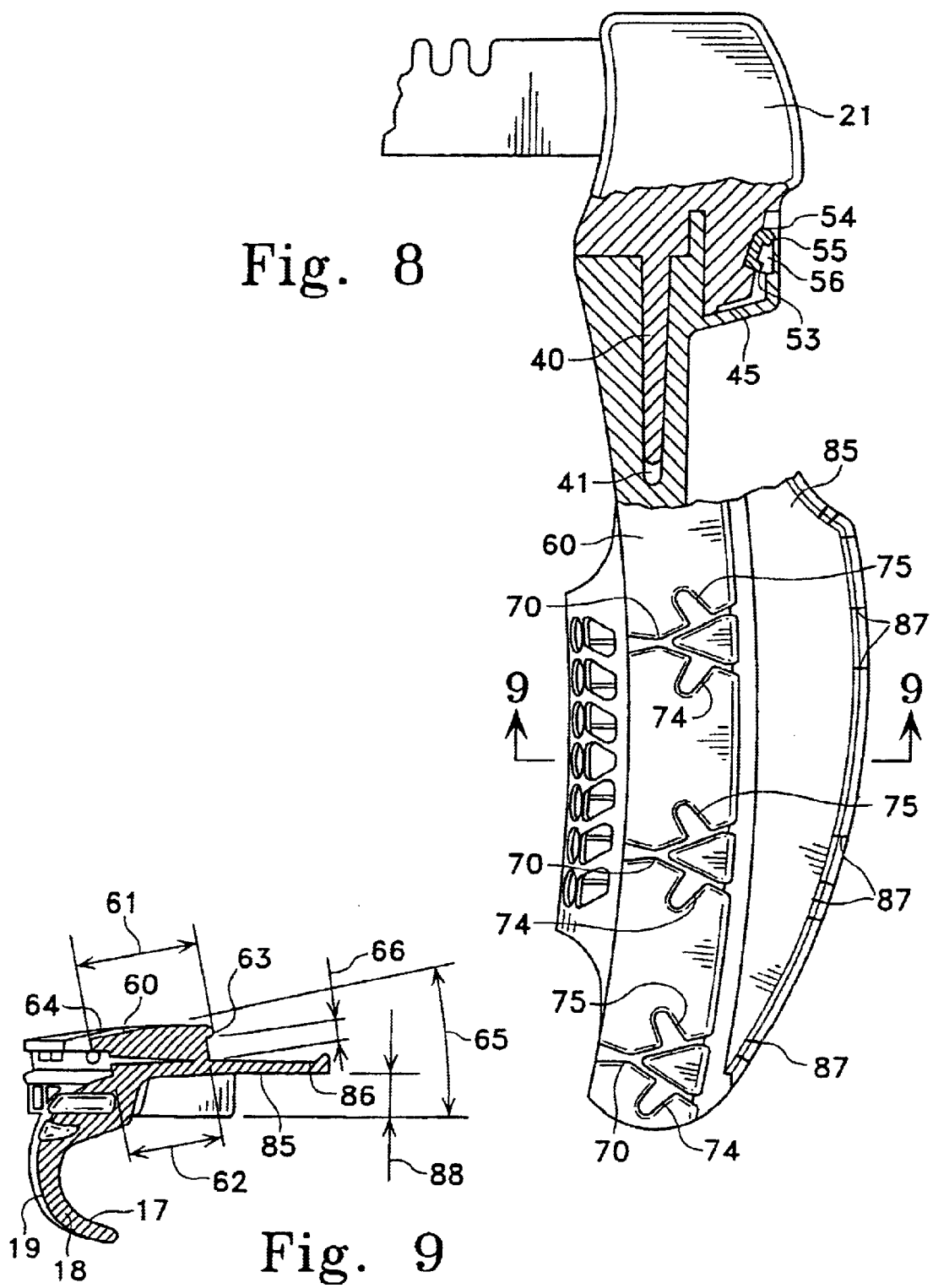

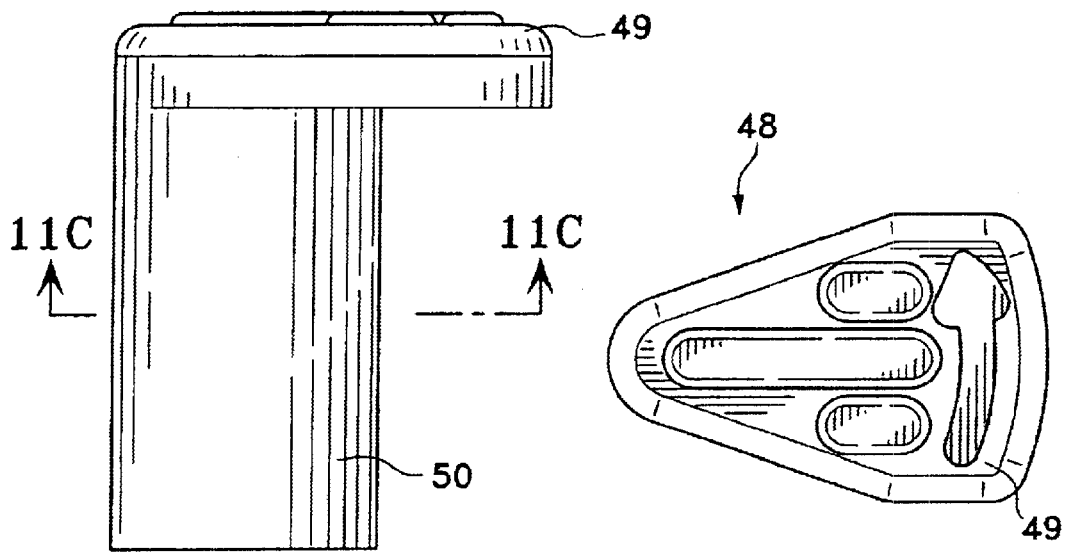
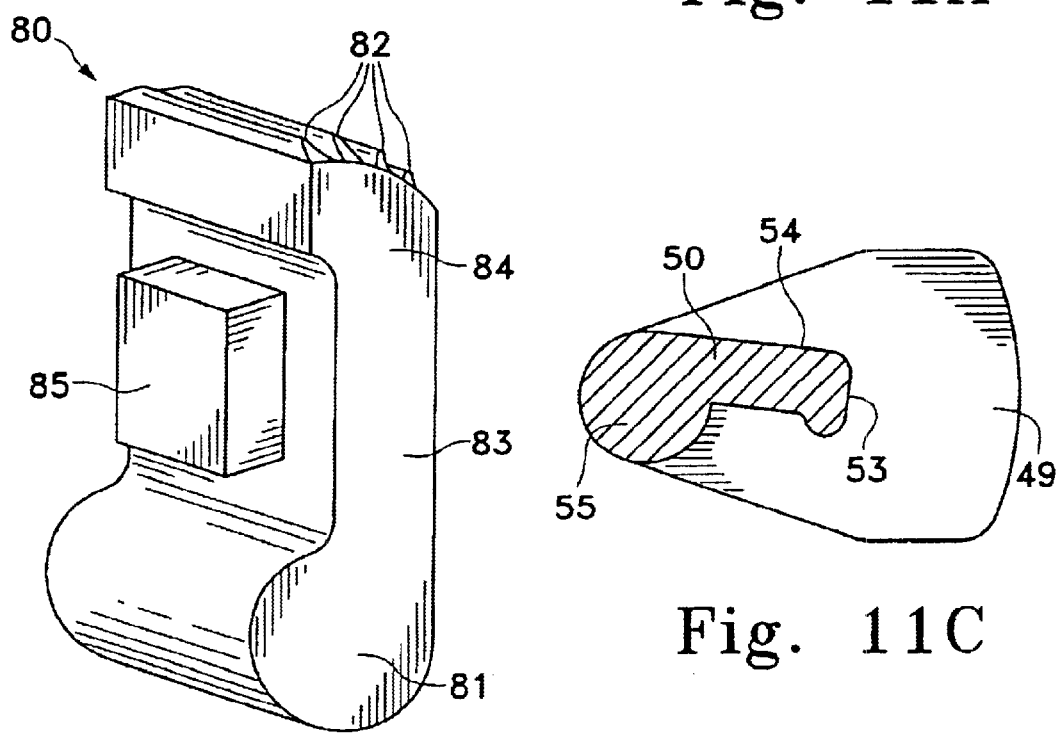

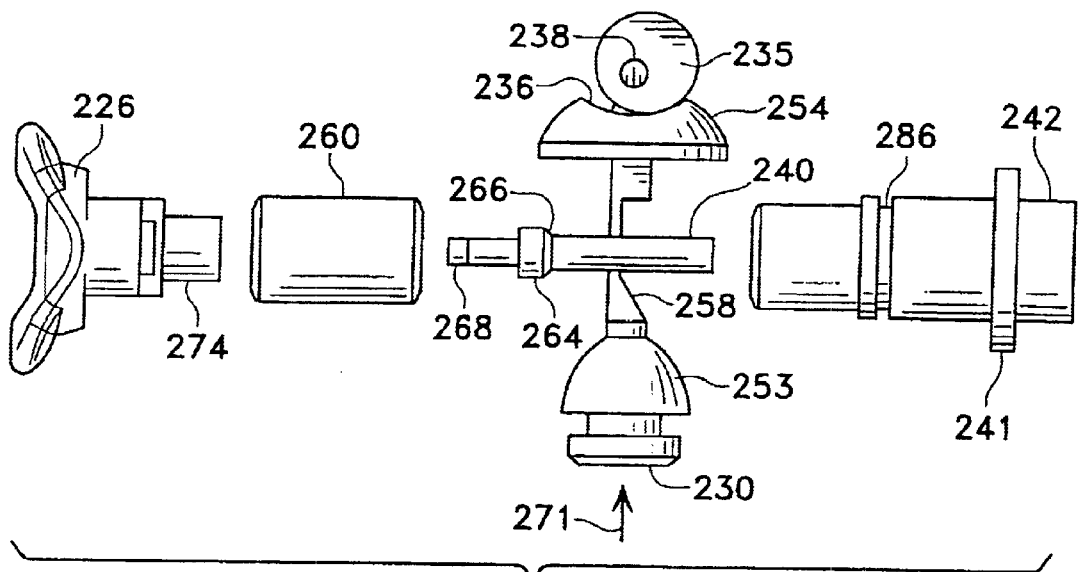
Fig. 26
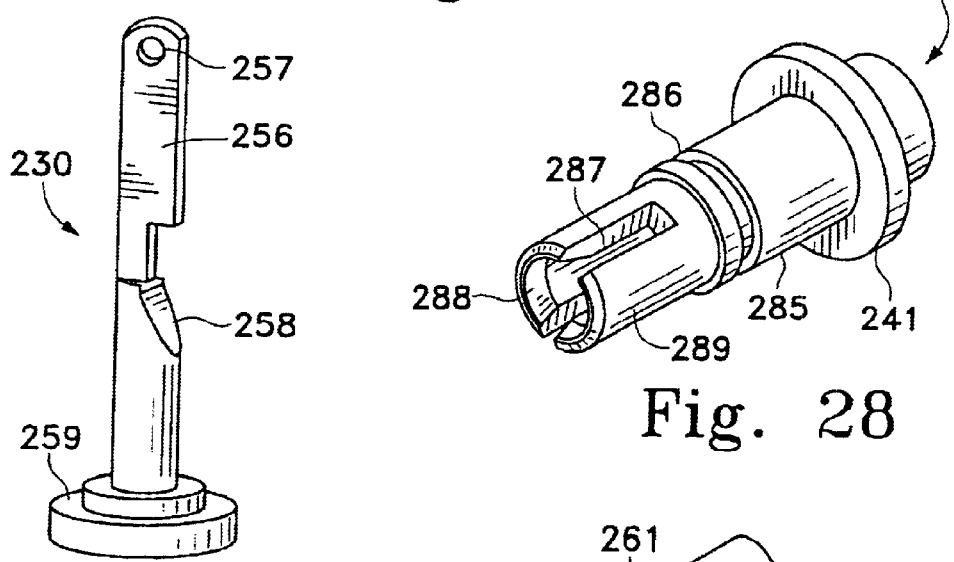
Fig. 27
Fig. 28
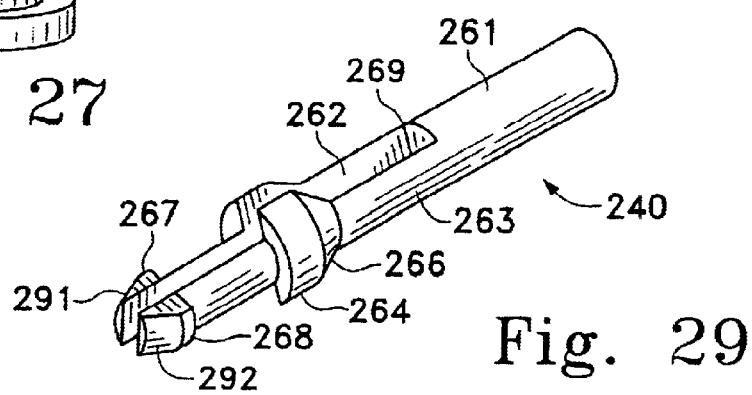
Fig. 29

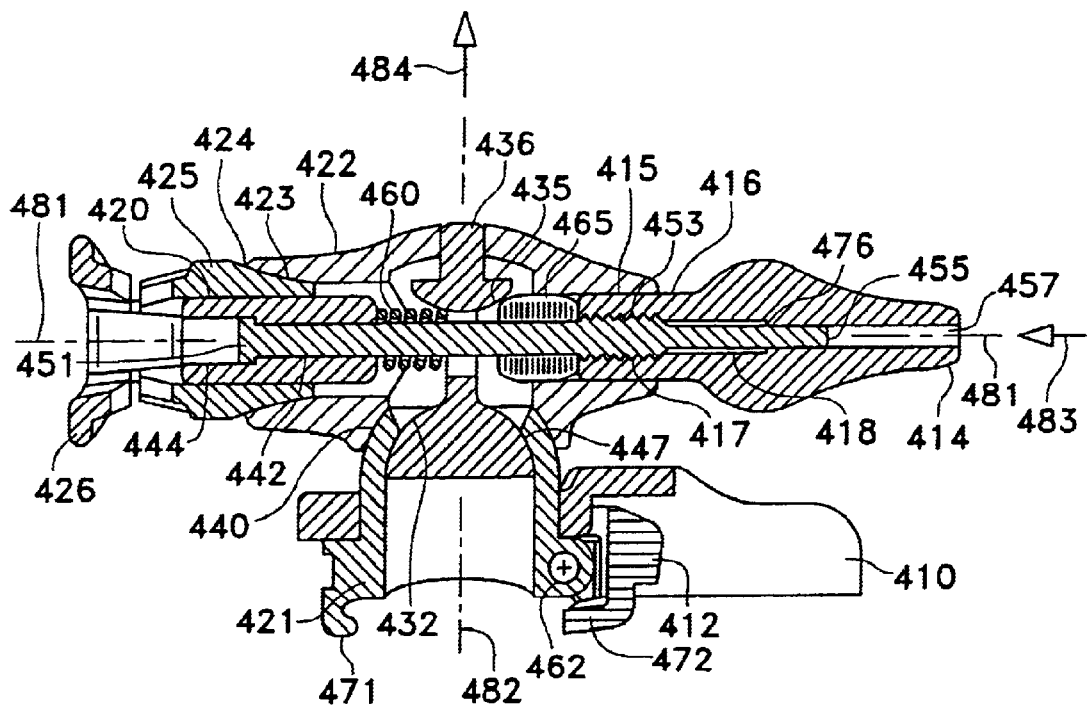
Fig. 36
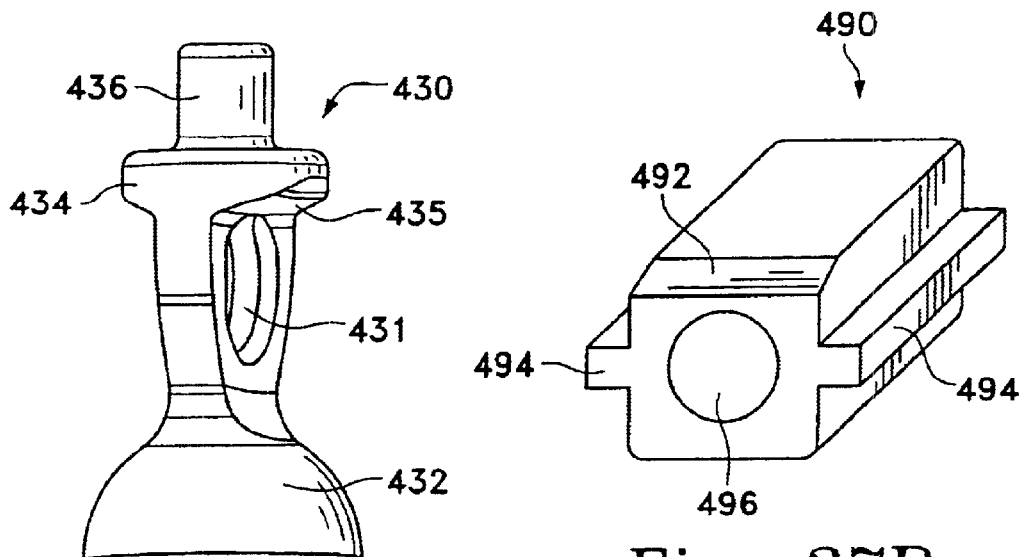
Fig. 37A
Fig. 37B

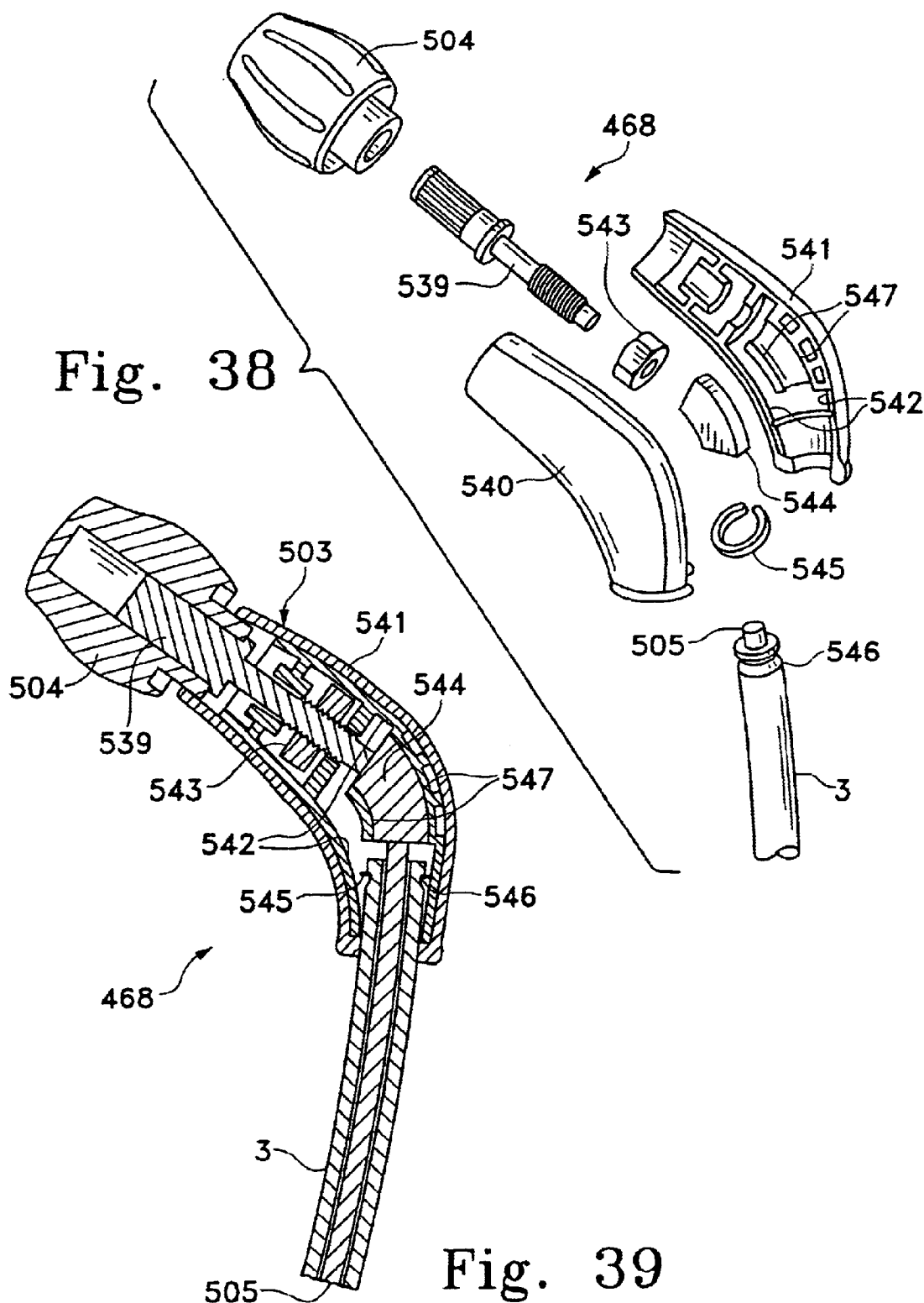

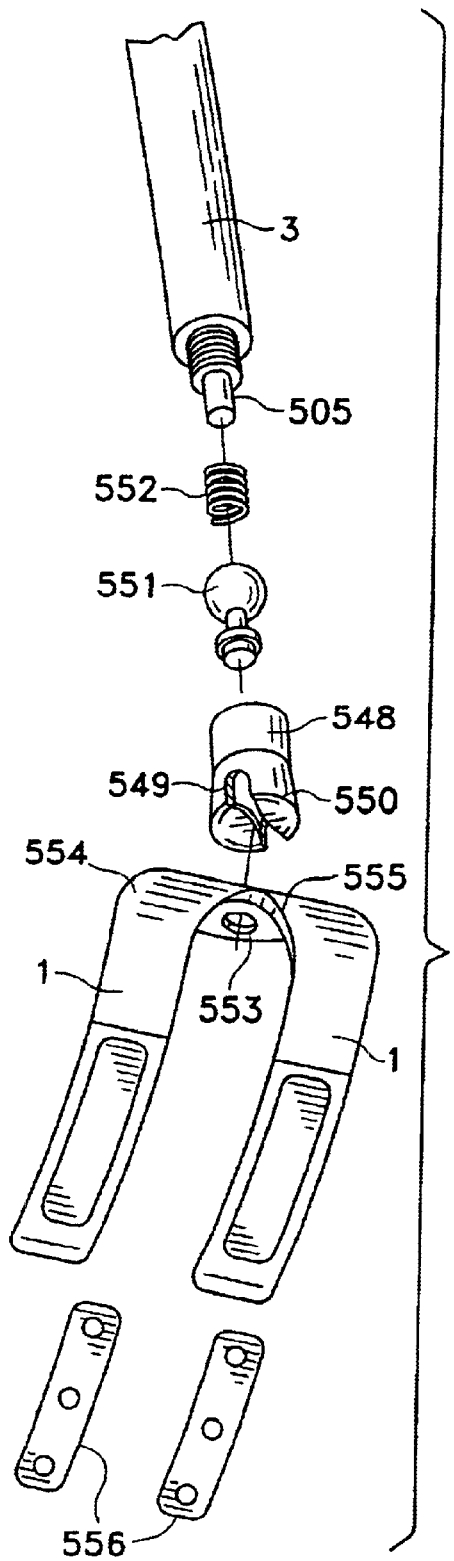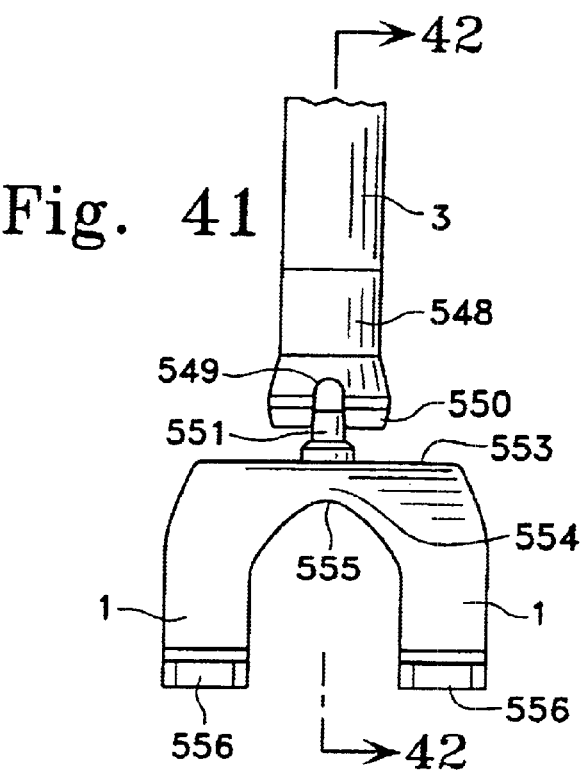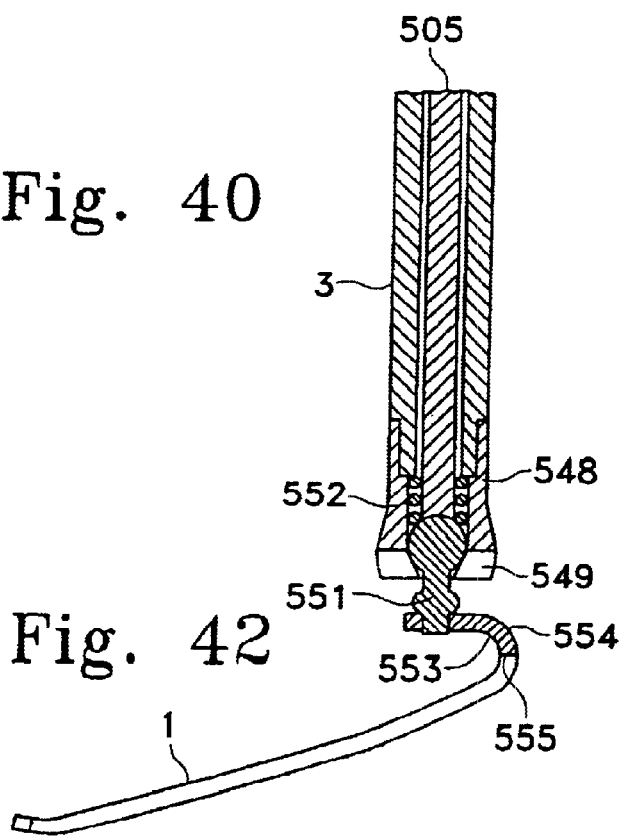
Fig. 40
Fig. 41
Fig. 42

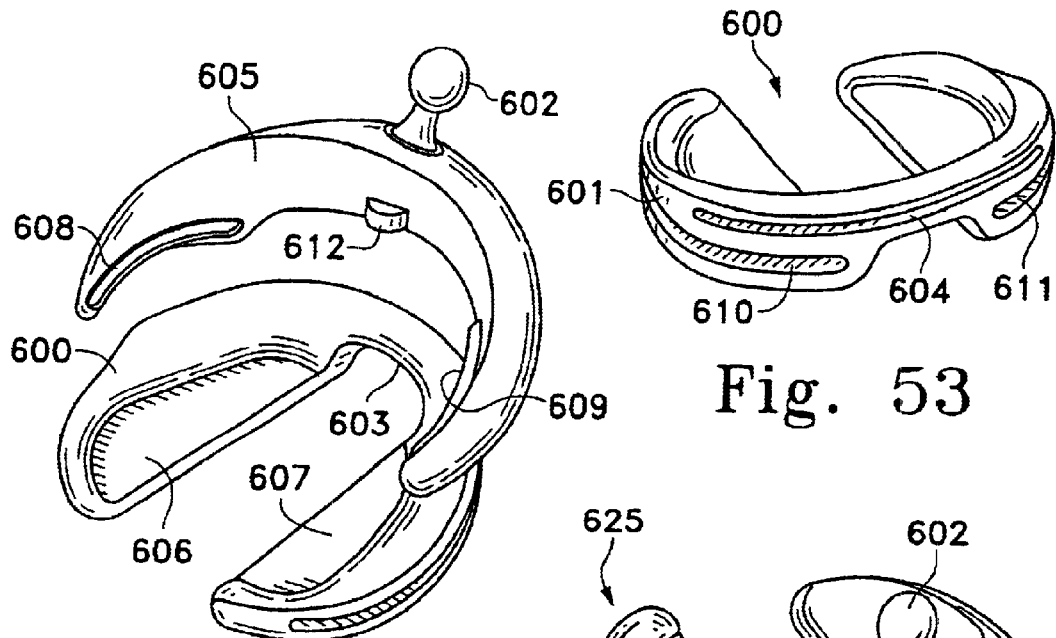
Fig. 52
Fig. 53
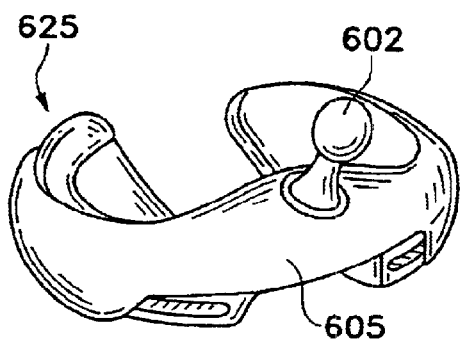
Fig. 54B
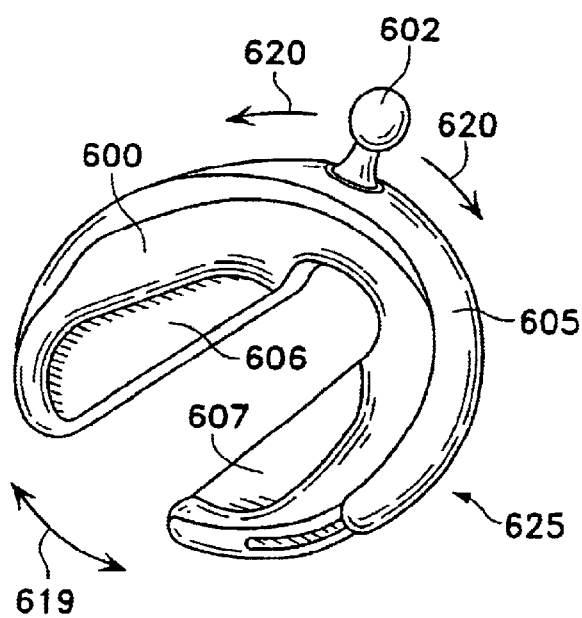
Fig. 54A
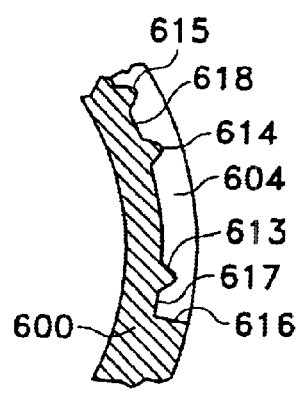
Fig. 55

SURGICAL INSTRUMENTS FOR ACCESSING AND STABILIZING A LOCALIZED PORTION OF A BEATING HEART

This application is a 35 USC 371 of PCTUS00/12239 filed May 4, 2000, which is a continuation in part of U.S. application Ser. No. 09/305,803, filed May 4, 1999, now U.S. Pat. No. 6,231,506; and a continuation in part of U.S. application Ser. No. 09/305,810, filed May 4, 1999, now U.S. Pat. No. 6,331,158; and a continuation in part of U.S. application Ser. No. 09/305,811, filed May 4, 1999, now U.S. Pat. No. 6,283,912; and a continuation in part of U.S. application Ser. No. 09/305,813, filed May 4, 1999, now U.S. Pat. No. 6,290,644; and a continuation in part of U.S. application Ser. No. 09/372,661, filed May 4, 1999, now abandoned; which is a continuation in part of U.S. application Ser. No. 09/305,810, filed May 4, 1999, now U.S. Pat. No. 6,331,158.

FIELD OF THE INVENTION

The present invention relates generally to surgical instruments, and more particularly to a surgical instrument mount apparatus and surgical retractor system useful for positioning and securing a variety of instruments including tissue stabilizer devices for use during coronary artery bypass graft surgery.

BACKGROUND OF THE INVENTION

Diseases of the cardiovascular system affect millions of people each year and are a leading cause of death throughout the world. The cost to society from such diseases is enormous both in terms of the number of lives lost as well as in terms of the costs associated with treating patients through traditional surgical techniques. A particularly prevalent form of cardiovascular disease is a reduction in the blood supply leading to the heart caused by atherosclerosis or other condition that creates a restriction in blood flow at a critical point in the cardiovascular system that supplies blood to the heart.

Treatment of such a blockage or restriction in the blood flow leading to the heart is, in many cases, treated by a surgical procedure known as a coronary artery bypass graft (CABG) procedure, more commonly known as a "heart bypass" operation. In the CABG procedure, the surgeon "bypasses" the obstruction to restore normal blood flow to the heart either by attaching an available source vessel to the obstructed target coronary artery or by removing a portion of a vein or artery from another part of the body, to use as a graft, and installing the graft between a point on a source vessel and a point on a target artery.

To restore the flow of blood to the heart, the CABG procedure requires that a fluid connection be established between two vessels. This procedure is known as an "anastomosis." Typically, a source vessel, such as a source artery with an unobstructed blood flow, i.e., the left internal mammary artery (LIMA), or a bypass-graft having one to end sewn to an unobstructed blood source such as the aorta, is sewn to a target occluded coronary artery, such as the left anterior descending (LAD) artery or other vessel that provides blood flow to the muscles of the heart.

Although the CABG procedure has become relatively common, the procedure itself is lengthy and traumatic and can damage the heart, the cardiovascular system, the central nervous system, and the blood supply itself. In a conventional CABG procedure, the surgeon makes an incision down the center of the chest, cuts through the sternum, performs several other procedures necessary to attach the patient to a heart-lung bypass machine, cuts off the blood flow to the heart and then stops the heart from beating in order to complete the bypass. The most lengthy and traumatic surgical procedures are necessary, in part, to connect the patient to a cardiopulmonary bypass (CPB) machine to continue the circulation of oxygenated blood to the rest of the body while the bypass is completed.

In recent years, a growing number of surgeons have begun performing CABG procedures using surgical techniques especially developed so that the CABG procedure could be performed while the heart is still beating. In such procedures, there is no need for any form of cardiopulmonary bypass, no need to perform the extensive surgical procedures necessary to connect the patient to a cardiopulmonary bypass machine, and no need to stop the heart. As a result, these beating heart procedures are much less invasive and the entire procedure can typically be achieved through a small number, typically one or two, comparatively small incisions in the chest.

Despite the advantages, the beating-heart CABG procedure is not universally to practiced, at least in part, because of the difficulty in performing the necessary surgical procedures using conventional surgical instruments. For example, it has been difficult for the surgeon to access the required areas of the heart requiring revascularization. In addition, the various surgical steps that are required to be performed on the heart itself are more difficult to perform because the heart muscle continues to move and contract to pump blood throughout the duration of the procedure.

The specific portion of the surgical procedure that creates the anastomosis in the beating-heart CABG procedure is particularly difficult. Completion of the anastomosis requires placing a series of sutures through extremely small vessels on the surface of the heart while the heart muscle continues to beat. Moreover, the sutures must be carefully placed to ensure that the source vessel or graft is firmly attached and will not leak when blood flow through the vessel is established. In cases where the target coronary artery is temporarily obstructed, for example, to improve the surgeon's visibility and avoid excessive blood loss, it is also important that the anastomosis procedure be performed rapidly to avoid ischemic damage to the heart.

Further adding to the difficulty of the procedure is the fact that the working space and visual access are often quite limited. The surgeon may be working through a small incision in the chest, for example, or may be viewing the procedure on a video monitor if the site of the surgery is viewed via surgical scope. The vessel, and particularly the arteriotomy to which a source vessel is to be anastomosed, may also be very difficult for the surgeon to see as it may be obscured more or less by layers of fat or other tissue.

The beating-heart CABG procedure could be greatly improved if the heart could be accessed and stabilized during the procedure such that the motion of the heart, particularly at the site of the anastomosis, is minimized even though the heart continues to beat and supply blood to the body. The beating-heart CABG procedure could be-further improved if the target vessel, and specifically the arteriotomy was presented to the surgeon in a way that allows sutures to be easily placed.

In view of the foregoing, it would be desirable to have improved devices for accessing and effectively stabilizing the beating heart at the site of the anastomosis. It would be desirable to have a retractor system that provides unobstructed and organized access to the areas of the heart requiring revascularization. It would be further desirable to have a low-profile, a traumatic stabilizing device that stabilizes the beating heart at the site of the anastomosis and provides a favorable presentation of the target vessel and the arteriotomy. It would be further desirable to provide a mount for the stabilizing device, or other instruments, that allows the stabilizing device to be easily maneuvered to the desired position and orientation, fixedly secured until the procedure is completed, and then easily removed from the site of the anastomosis.

SUMMARY OF THE INVENTION

The present invention will be generally described for use in performing CABG surgery, but the invention is not limited thereto, and is contemplated to be useful for other surgical procedures requiring surgical instruments to be positioned and secured through an incision into a patient.

The present invention involves various aspects of an instrument mount useful for positioning and securing surgical instruments, for example, during a CA procedure on a beating heart. One aspect of the present invention involves a low-profile, flexible, right-angle instrument mount for maneuvering and securing a wide array of surgical instruments.

One aspect of the present invention involves an instrument mount apparatus for positioning a surgical instrument comprising a mount body having a base portion moveably coupled at a first articulating joint and a side portion moveably coupled at a second articulating joint, the first and second articulating joints being freely moveable when in an unlocked condition and substantially immovable when in a locked condition which may be accomplished through manipulation of a single actuator.

The actuator may include a base post assembled thorough the base portion and the mount body arid interconnected at a first end to a cam operatively interfacing a contact surface on the mount body, and a tie pin having a slotted portion which receives the base post. Operation of the cam draws the base post toward the cam and into a locked position. A ramped portion of the base post drives the tie pin into the locked position.

A grip member may be included, which forms an opening with the side portion for receiving a surgical instrument. The tie pin may be connected, at a first end, to the grip member, preferably by a pair of flexible prongs. Movement of the tie pin to the locked position draws and locks the grip member against the side portion and also locks the second articulating joint.

The tie pin may further be releasably connected to a release button at a second end, such that pressing of the release button extends the tie pin and grip member to allow removal of the grip member to exchange surgical instruments.

Preferably, the first articulating joint is at an angle relative to the second articulating joint. The angle between the first and second articulating joints is typically less than about 130 degrees, more typically less than 120 degrees. In a preferred embodiment, the angle is between about 100 degrees and about 45 degrees, most preferably about 90 degrees.

The articulating joints may be any mechanical configuration which provides the desired degrees of freedom for maneuvering a surgical instrument. Preferably, the first articulating joint comprises a ball-type joint or a ball and socket joint. The ball and socket joint may comprise a ball-shaped member extending from the base portion and a cooperating socket formed within the mount body. The second articulating joint may preferably comprise a ball and socket joint or a rotational joint. When the second articulating joint is configured as a rotational joint, it may comprise a frustoconical member extending from the side portion and a cooperating frustoconical cavity within the mount body.

The side portion and the base portion may include a number of other features or structures connected thereto for a variety of purposes which take advantage of the movement of the side portion relative to the base portion provided by the articulating joints. For example, the side portion may further include a grip member. The side portion and the grip member may be positioned to form an opening therebetween for receiving a surgical instrument. The grip member may have an unlocked condition relative to the side portion wherein the opening allows relatively free movement of the surgical instrument and a locked condition wherein the grip member and the side portion are forced together to lock the instrument against relative movement.

The base portion may be adapted to cooperatively engage a rail member. The rail member may generally have a T-shaped cross-section. In a preferred embodiment, the rail has a top portion and a bottom portion, the bottom portion having a narrowed region adjacent the top portion forming first and second tabs on the top portion and the base portion further comprises first and second hooks adapted to engage the first and second tabs. Preferably at least one of said hooks is moveable relative to the other to allow the base portion to lock onto and release from the first and second tabs. The rail is preferably fixed or otherwise associated with a sternal or rib retractor.

Another aspect of the present invention involves an instrument mount apparatus for positioning and securing a surgical instrument which includes a mount body having a base portion moveably coupled at a first articulating joint and a side portion moveably coupled at a second articulating joint. A post preferably extends through the first articulating joint along a first axis and has a first end portion engaging the base portion. A pin preferably extends through the second articulating joint along a second axis and has an end portion engaging the side portion and a threaded portion. A knob is may be provided having an internal bore for receiving at least a portion of the pin, the internal bore having threads adapted to engage the threaded portion of the pin. The knob may preferably have a thrust surface associated therewith adapted to engage and move the post as the knob traverses over the threaded portion of the pin in response to rotation of the knob.

Again, the articulating joints may be any mechanical configuration which provides the desired degrees of freedom for maneuvering a surgical instrument. Preferably, the first articulating joint comprises a ball-type joint or a ball and socket joint. The ball and socket joint may comprise a ball-shaped member extending from the base portion and a cooperating socket formed within the mount body. The second articulating joint may to preferably comprise a ball and socket joint or a rotational joint. When the second articulating joint is configured as a rotational joint, it may comprise a frustoconical member extending from the side portion and a cooperating frustoconical cavity within the mount body.

The post may preferably further comprises a cam surface positioned to mate with the thrust surface, whereby rotation of the knob along the threaded portion causes translation of the thrust surface in a direction along the second axis, the thrust surface engaging the cam surface to move the post in a direction generally along the first axis. The knob may include a first end adapted to be grasped by a user and a housing end adapted to be received within the mount body. The thrust surface may be located on the housing end of the knob. In another configuration, the thrust surface may be provided on a lift member which is slidable along the second axis. The lift member may have a first end having the thrust surface and a second end. The housing end of the knob is preferably positioned to engage the second end of the lift member such that when the knob is traversed along the second axis, it engages the lift member which causes the thrust surface to engage the cam surface thus causing the post to move along the first axis.

When the post is urged in a first direction along the first axis, the first articulating joint preferably becomes locked. When the first articulating joint is a ball and socket joint formed between a ball extending from the base portion and a socket formed within the mount body, the ball and socket become locked by operation of the first end of the post which engages the base portion and forces the two together as the post is urged upwards. When the post moves in the opposite direction, the articulating joint returns to a condition which allows relatively free articulation. A second end of the post is may be constrained within a top opening provided in the mount body. Preferably, the second end is slidable within the top opening generally along the first axis.

These and other features of the present invention will become more fully apparent from the following description and appended claims.

BRIEF DESCRIPTION OF THE DRAWINGS

FIG. 4 is a perspective view illustrating an exemplar bar assembly.

FIG. 5 is a perspective view illustrating a moveable housing associated with the retractor drive.

FIG. 6 is a perspective view illustrating a retractor drive handle assembly.

FIG. 8 is a top view in partial cross-section illustrating the platform blade and retractor drive assembly in an engaged position.

FIG. 9 is a cross-sectional view taken along line 9—9 shown in FIG. 8.

FIGS. 11A, 11B, and 11C illustrate a preferred platform blade latch. FIGS. 11A and 11B are top and front plan views, respectively. FIG. 11C is a cross-sectional view 10 taken along line 11C—11C as shown in FIG. 11B.

FIG. 12 is a perspective view showing a preferred suture lock.

FIG. 26 is an exploded assembly view showing selected components of a 15 preferred closing mechanism.

FIG. 27 is a perspective view illustrating a preferred instrument mount cam post.

FIG. 28 is a perspective view illustrating a preferred instrument mount release button.

FIG. 29 is a perspective view illustrating a preferred instrument mount follower post.

FIG. 36 is a cross-sectional view taken along line 36—36 as shown in FIG. 33.

FIG. 37A is a perspective view of the preferred base post for the instrument mount assembly shown in FIGS. 33–36.

FIG. 37B is a perspective view of an alternative embodiment of a lifter.

FIGS. 38 and 39 are exploded perspective and cross-sectional views respectively of a handle mechanism of a preferred tissue stabilizer.

FIG. 40 is an exploded perspective view of a contact member of the stabilizer shown in FIGS. 38 and 39.

FIG. 41 is a rear plan view of the contact member of FIGS. 38, 39 and 40.

FIG. 42 is a cross-sectional view of the contact member of FIG. 41 taken along line 42—42.

FIG. 52 is a front perspective exploded view of a stabilizer base assembly having an adjustable ball/post position.

FIG. 53 is a rear perspective view of the stabilizer base of FIG. 52.

FIGS. 54A and 54B are front and rear perspective views of the stabilizer base assembly of FIG. 52.

FIG. 55 is a partial cross-sectional view through a portion of the rear guide slot of the stabilizer base of FIG. 52.

DETAILED DESCRIPTION

Figure 1:
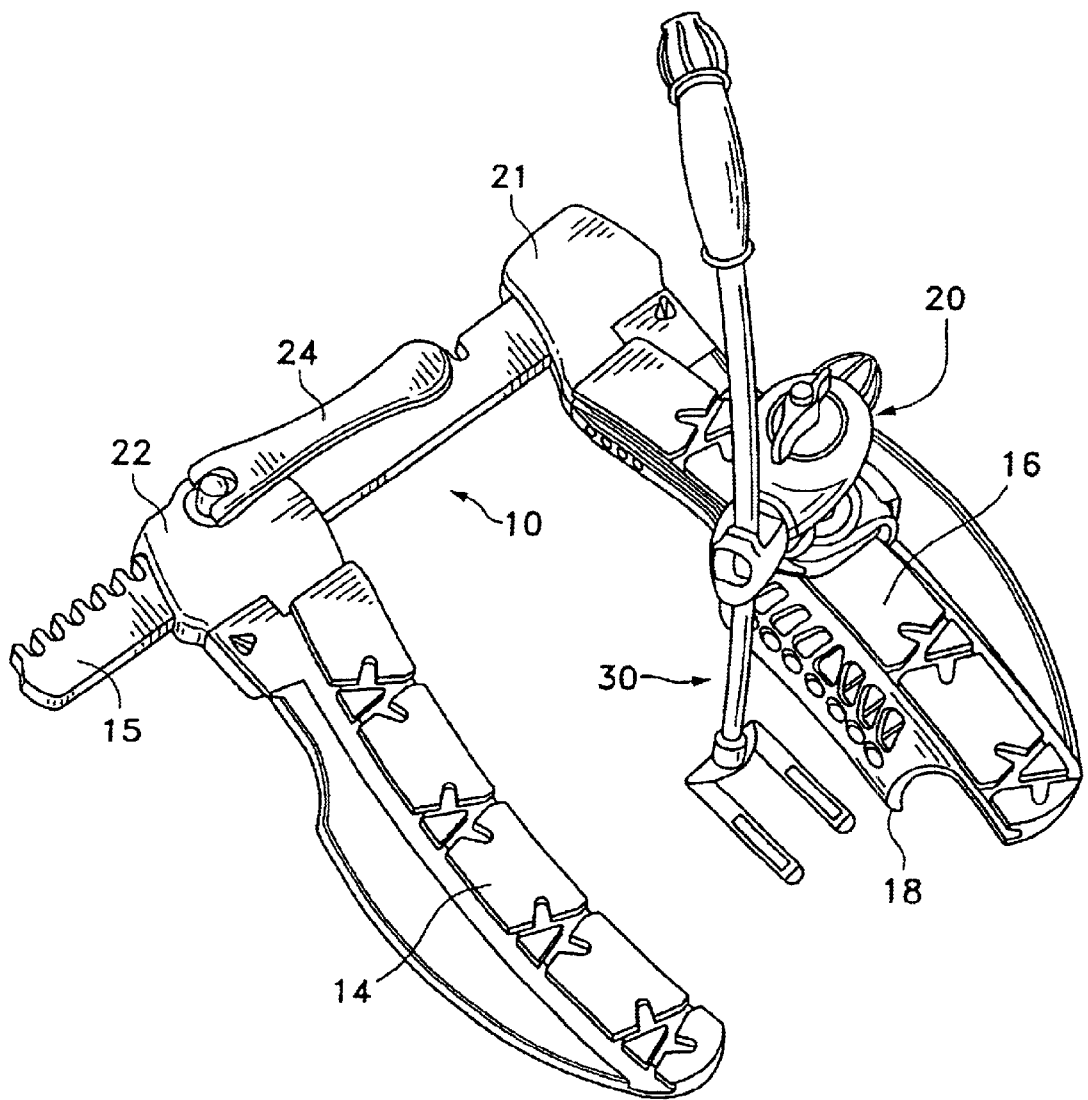
FIG. 1 is a perspective view illustrating a cardiac surger system according to the principles of the present invention.

The present invention involves surgical instruments for accessing and stabilizing the heart and methods for their use. The present invention may involve a retractor system or assembly for accessing the heart. The present invention may also include a mount that allows various instruments to be easily positioned within the surgical working space, locked or secured into a desired position for the duration of a particular surgical procedure, and then easily and safely removed from the working space. According to a preferred embodiment the instrument may be a device to facilitate stabilization of the heart during coronary surgery.

Although the instruments and methods of the present invention may have application in both conventional stopped-heart and beating heart procedures, they are preferably used to access and stabilize the beating heart during a minimally invasive coronary artery bypass graft (CABG) operation which has been specially developed to facilitate completion of an anastomosis, typically between a target artery and a bypass graft or source artery, without requiring cardiac arrest such as cardioplegia or fibrillation and without cardiopulmonary bypass (CPB). Further although the instruments for accessing and stabilizing the beating heart can be applied in a number of different surgical contexts involving various incisions and surgical approaches to the heart as are known in the art, the instruments and devices described herein are most advantageously employed in a CABG procedure wherein the heart is accessed through only one or two minimally invasive incisions in the chest.

Although the particular source vessel and target artery of the anastomosis are determined clinically, a common minimally invasive bypass procedure on the beating heart includes an anastomosis which forms a connection between the left internal mammary artery (LIMA) as the source artery, and the left anterior descending artery (LAD) as the target artery. To complete the anastomosis, the surgeon must dissect a portion of the LIMA by separating it from the internal chest cavity. Once dissection of the LIMA is achieved, the surgeon may attach the dissected LIMA to the target coronary artery, i.e., the LAD by way of creating an anastomosis.

In this example, the present invention may involve a number of discrete components that facilitate access to the anastomosis site, allow various instruments or devices to be maneuvered and secured in place, and provide stabilization of the heart. The retractor of the present invention may be used to provide access to the anastomosis site of the target artery on the heart itself. The various stabilizer embodiments of the present invention may be used to stabilize the beating heart during at least the portion of the procedure during which the surgeon completes the anastomosis of the LIMA to the LAD. The mount of the present invention may be used to facilitate convenient manipulation of the stabilizer, and other instruments or devices, to their desired position and allows the devices to be secured in that desired position. Although the LIMA to LAD anastomosis is provided as one example, it is readily appreciated that the techniques and instruments described herein may be applied to other procedures depending on the clinical diagnosis and the patient's anatomy.

Although each component of the present invention may be used separately with great benefit, the components are preferably used in unison to provide a surgical system which provides an unobstructed and organized surgical field, exceptional instrument maneuverability and access to the heart facilitating total revascularization of the heart if required, and effective vessel stabilization during the anastomosis procedure. Although the present invention will have application whether access to the heart is achieved by way of a full-sternotomy, mini-sternotomy, para-sternotomy, thoracotomy or other known to approach, the exemplar embodiments described below will be generally described with reference to a coronary artery bypass procedure using a mid-sternal approach.

Referring to the figures wherein like numerals indicate like elements, an exemplar surgical system for performing a mid-sternal surgical procedure on the beating heart is illustrated in FIG. 1 and includes retractor assembly 10, mount assembly 20 and stabilizer assembly 30.

Retractor assembly 10 generally includes a pair of opposing blades adapted to engage opposite sides of a sternal incision, or other incision, and a drive mechanism constructed to force the blades, and thus the sternum apart. Using the drive mechanism, the sternum may be spread to the desired opening, thus providing the desired access and direct visualization of the thoracic cavity. If desired, the heart may be positioned or oriented to best present the target vessels for anastomosis. This positioning may be established, for example, through the strategic placement and tensioning of sutures in the pericardial sac, by appropriately placing the patient in the Trendelenburg position, or by using a heart positioned in the form or a strap or pad or the like.

Once the target vessel is in the desired position, at least one component of stabilizer assembly 30 is brought into contact with the beating heart adjacent the target site of the anastomosis. The surgeon then applies a stabilizing force to the beating heart via the stabilizer assembly 30 which may then be fixed in place, preferably to the retractor assembly 10 by way of mount assembly 20. The stabilizing force supplied by the stabilizer assembly substantially eliminates movement of the heart in the area of the anastomosis so that the surgeon may accurately and efficiently perform the required anastomosis (or other surgical procedure). After the anastomosis has been completed, the stabilizing force is released and the contacting component of stabilizer assembly 30 is removed from the anastomotic site.

Each of the principal components, the preferred surgical system, and their methods of use are separately described in detail below. A preferred retractor according to the principles of the present invention is described below with reference to Figures 212. A preferred stabilizer or instrument mount according to the principles of the present invention is described below with reference to FIGS. 13–32. Preferred stabilizer embodiments according to the principles of the present invention are described below with respect to FIGS. 33–44. A preferred surgical system and methods for performing a coronary artery bypass on a beating heart according to the principles of the present invention is described below with respect to FIG. 45.

The Retractor

According to the principles of the present invention, the retractor generally involves a drive mechanism and a pair of opposing blades adapted for insertion into an incision and for engaging opposite sides of the incision. The drive mechanism functions in some manner to urge the opposing blades apart, thus forcing opposite sides of the incision open to allow surgical access through the incision. For purposes of performing a coronary artery bypass, the incision may be any suitable incision which provides the desired access to the thoracic cavity and more specifically a desired area of the heart. For purposes of example only, the retractor of the present invention will be described with respect to a midsternal incision, however skilled artisans will recognize that many aspects of the invention are equally applicable to other surgical approaches to the heart, for example, by way of a thoracotomy, or other suitable access approach.

When the heart is accessed by way of an incision through all or a portion of the sternum, the opposing blades are adapted to be inserted into and engage opposite sides of a sternal incision such that the severed sternum may be forced apart by the action of the opposing blades to create a working space for operating on the heart. Typically, the drive mechanism is constructed to spread the opposing blades apart in a generally parallel fashion, however, the parting motion may also have a significant curvilinear or angular component as well.

In one embodiment, the blades may be permanently, integrally, or inseparably formed with a drive mechanism. Preferably however, at least a portion of the blades are separable from the drive mechanism. That is, at least some of the features and functions associated with the retractor blades are allocated to a structural component which is separate, separable, or otherwise detachable from the drive mechanism. The separate component and the drive mechanism may be manufactured independently and then subsequently assembled at the factory or, more preferably, at the point of use.

A retractor construction having a separable component allows the features and functions of the drive mechanism to remain separate from the remainder of the retractor assembly and vice versa. This allows a greatly simplified or depopulated drive mechanism and allows the separable component to have a much more sophisticated construction with increased features and functionality. Accordingly, the simplified drive mechanism, which is typically required to be made from a hardened steel, is easier and more economical to manufacture and easier to maintain, clean and sterilize post surgically. Moreover, the separate component can be economically made from materials or processes that allow for the intricate structural features which provide superior functionality.

In a preferred embodiment, the drive mechanism is constructed to be re sterilized and reused a relatively large number of times, and the feature-rich separate component is constructed to be disposable, i.e. discarded after a single surgical use. Thus, the depopulated drive mechanism, which will be used over and over, can afford to be constructed to be quite robust with a view to materials and manufacturing processes that will support the rigors of such extended surgical service. The separable component, free from the typical functional requirements of the drive mechanism and the service requirements of extended surgical re-use, may preferably be constructed from any number of engineering materials to produce an economical component having the desired features and which may be discarded after a single use if desired.

Figure 2:
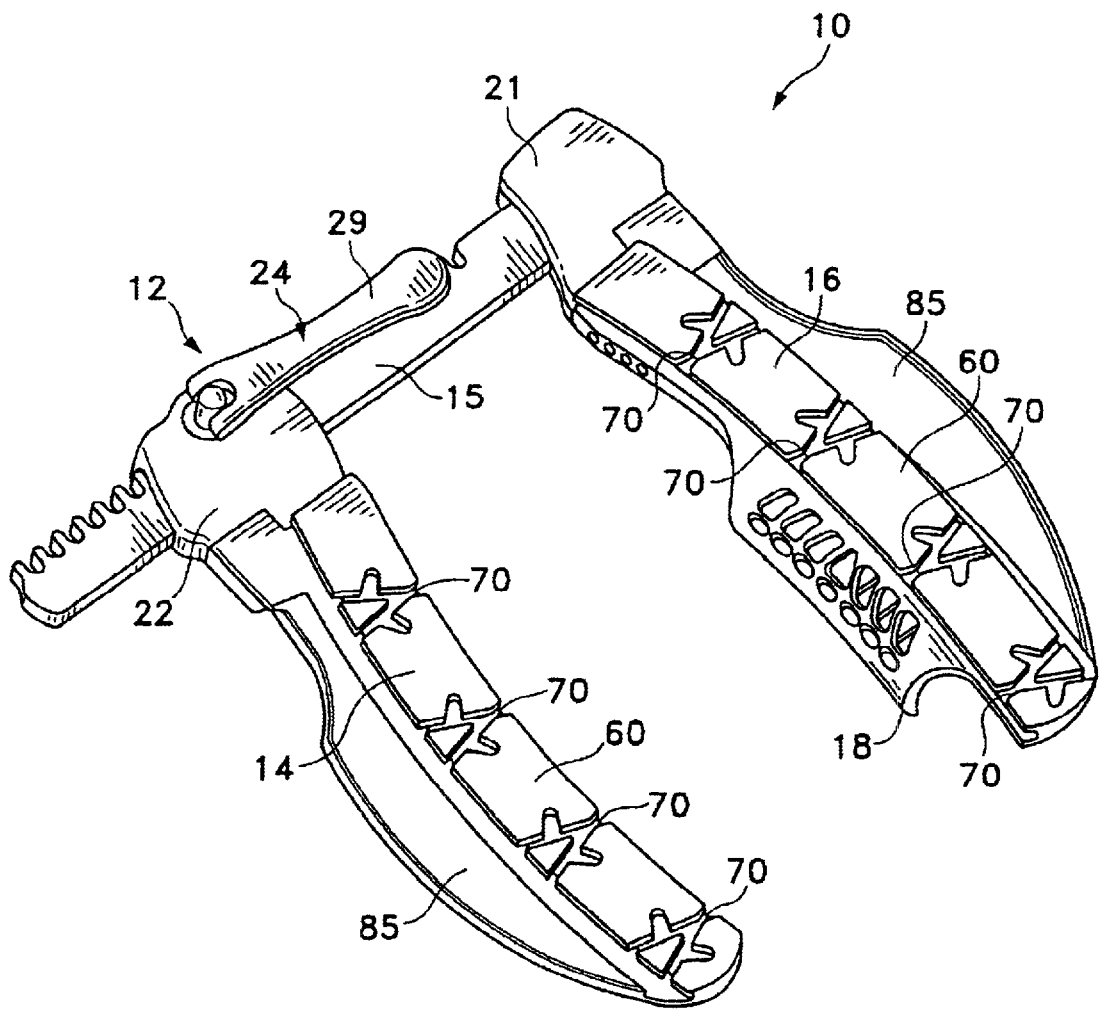
FIG. 2 is a perspective view illustrating a retractor assembly according to the principles of the present invention.

In a preferred embodiment, retractor assembly 10 comprises a drive 12 and first and second platform blades 14 and 16 detachably connected to drive 12, as illustrated in FIG. 2. Preferably first platform blade 14 and second platform blade 16 each have one or more channels or engaging members 18 adapted to engage opposite sides of an access incision. Activation of drive 12 forces apart first and second platform blades 14 and 16 thereby causing engaging members 18 to correspondingly force the incision open to provide access to the desired surgical site.

In the example of a sternal approach to the heart, engaging members 18 are adapted to engage each side of the incised sternum to reliably hold and engage the sternum as the sternum is forced open to expose the thoracic cavity and ultimately the heart. As best seen in FIG. 9, which illustrates a cross-section of second platform blade 16, engaging member 18 is generally in the form of a channel or the like, preferably having a U-shape, curved shape, or other shape suitable for engaging the incised sternum.

Preferably, engaging member 18 generally has a concave interior profile 17 for engaging and holding the sternum and a corresponding convex exterior profile 19 that is relatively smooth so as not to interfere with other surgical instruments, snag sutures or create other such difficulties. The engaging members 18 are preferably constructed to have sufficient strength to withstand the loads required to spread the sternum yet maintain a suitably low profile to facilitate easy insertion into the access incision and to require as little space within the working incision as possible.

It may be desirable to provide engaging members 18 with features to reduce trauma to the incision site, increase the traction against the sides of the incision, or both. A thin pad or layer of non-slip or a traumatic material (not shown) may be fixed, by way of an adhesive or other suitable fastening technique, to the interior profile 17 if desired to reduce slippage and trauma to the severed sternum or surrounding tissue. Alternatively, the desired features may be integrally fabricated into engaging members 18. For example, when platform blades 14 and 16 are injection molded components, traction features such as raised bumps, ribs, indentations, or the like can be molded integral into engaging members 18.

Figure 3:
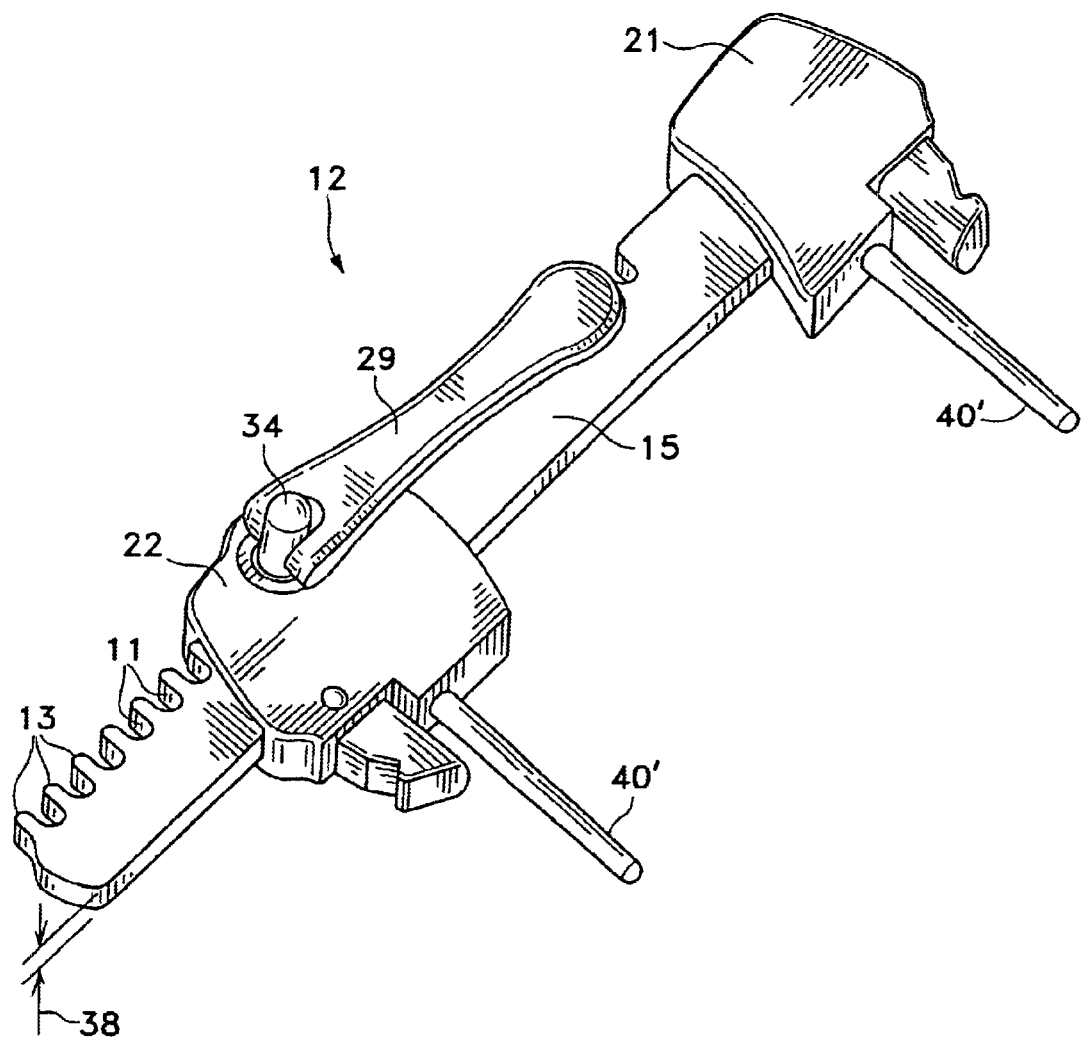
FIG. 3 is a perspective view illustrating a preferred retractor drive assembly.

Referring to FIGS. 2–6, drive 12 is preferably constructed to force the platform blades apart in generally opposite directions. Any type of drive mechanism which provides the desired separating action of the blades may be suitable. A common, substantially straight-line parting motion may be provided by a ratchet or rack arrangement as is generally known in the art. FIG. 3 illustrates a preferred drive 12 which involves a bar 15, moveable housing 22 and handle assembly 24 which facilitates movement of moveable housing 22 relative to bar 15. A first end of first blade 14 may be operably attached to moveable housing 22 and second blade 16 to bar 15.

In a preferred embodiment, bar 15 is a substantially rigid bar having a stationary or fixed housing 21 assembled thereto and thus forming bar assembly 23. Fixed housing 21 may be fastened to one end of bar 15 using one or more mechanical fasteners, an interference fit, suitable adhesive or bonding compounds, welding, or any other suitable fastening technique. A first end of second blade 16 is preferably operably attached to fixed housing 21. As with moveable housing 22, fixed housing 21 may be of any configuration which provides for the structural attachment of first and second platform blades 14 and 16.

Bar 15 preferably includes a number of teeth 13 evenly spaced along at least a portion of its length. Teeth 13 may have substantially parallel side portions 11 and may have radiused tops 25. The exterior edges of teeth 13 may be broken or radiused or have a chamfer 26 as shown. Handle assembly 24 preferably includes a means for engaging teeth 13 so as to drive moveable housing 22 relative to bar 15 to any desired position under load where it remains so positioned against the load without need for any applied input or holding force. The means for engaging teeth 13 could be any suitable gear, ratchet, cog or like mechanism. Bar 15 may also be adapted and used for receiving an instrument mount, such as those described in detail below.

In a preferred embodiment, moveable housing 22 is driven using one or more drive pins which may successively engage teeth 13 in a cogging manner. Handle assembly 24 includes drive handle 29 connected to first and second cylindrical drive bearings 31 and 32. Drive bearing 31 preferably has a raised boss 34 extending from one end to which drive handle 29 may be pivotally connected by way of pin 33. At the opposite end, drive bearing 31 has first drive pin 27 and second drive pin 28 extending therefrom and terminating at second drive bearing 32. First and second drive bearings 31 and 32 are spaced apart a distance 35 which is selected to be slightly greater than the thickness 38 of bar 15 such that a portion of bar 15 may be received between first and second drive bearings 31 and 32. The outside diameters of drive bearings 31 and 32 are selected so as to fit within guide holes provided in moveable housing 22. For example, the outside diameter of second drive bearing 32 is sized to accurately rotate within guide hole 36.

Moveable housing 22 has a bore 37 extending therethrough for receiving bar 15. Bore 37 generally has a shape corresponding to the dimensions of the cross-section of the potion of the bar 15 which is to pass through bore 36. With handle assembly 24 properly positioned within the guide holes provided in moveable housing 22, it may be assembled to bar 15 by placing the end of bar 15 within bore 36 and turning handle 29 such that first and second drive pins 27 and 28 become engaged with teeth 13. Once assembled in this manner, moveable housing 22 may be forced one way or the other along the length of bar 15 by turning handle 29, and thus drive bearings 31 and 32, to cause first and second drive pins 27 and 28 to progressively engage teeth 13 along bar 15.

As mentioned above, first and second platform blades 14 and 16 may be removably assembled to moveable housing 22 and fixed housing 21, respectively. Platform blades 14 and 16 may be attached in any suitable fashion including, for example, threaded connections or other mating features on the platform blades and housings themselves, ordinary or specialized mechanical fasteners, and cam or latching mechanisms adapted to secure the platform blades to the housings. In a preferred embodiment, both moveable housing 22 and fixed housing 21 are constructed with features that engage, secure and support first and second platform blades 14 and 16 in an operable position on drive 12, thus providing an assembled retractor 10 which is ready for surgical use.

Figure 7:
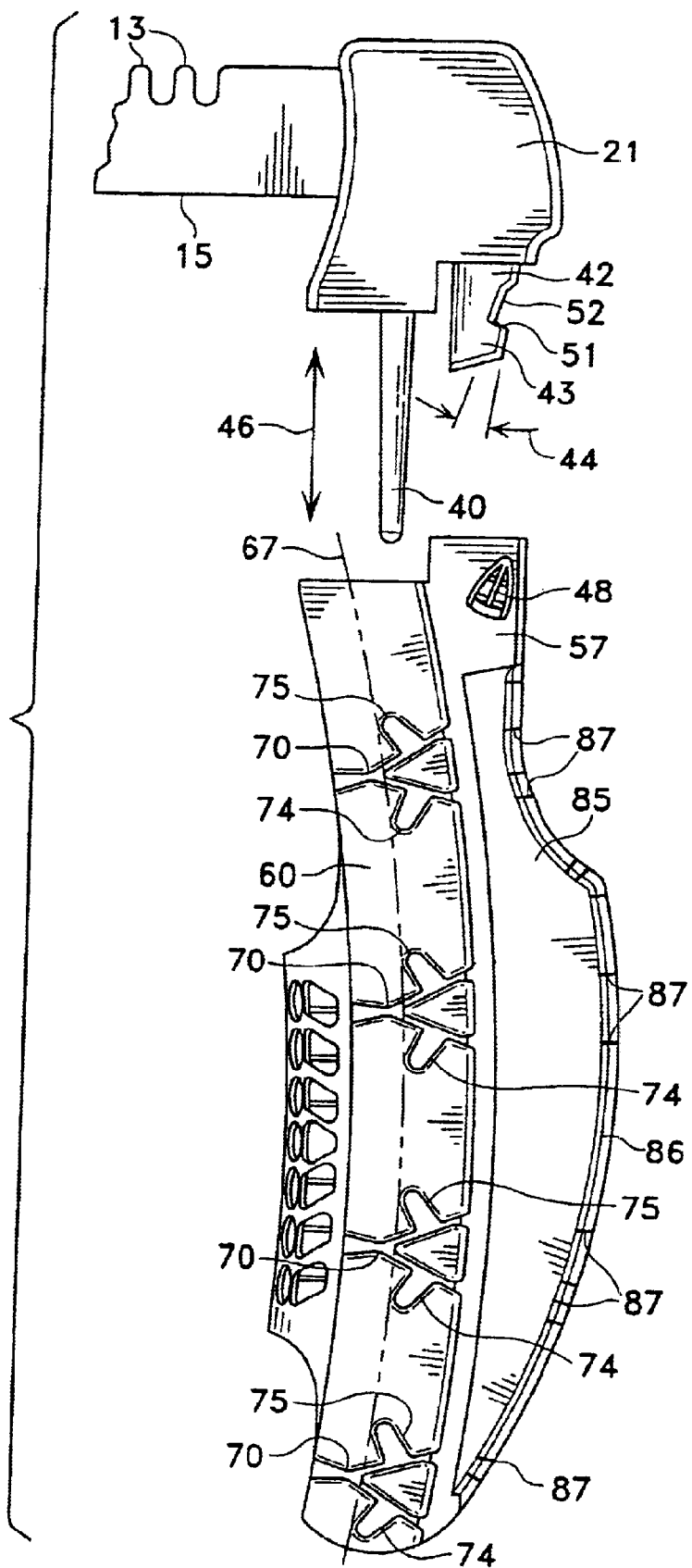
FIG. 7 is a top plan view illustrating a preferred platform blade and retractor drive assembly in an unengaged position.

Referring to FIGS. 7 and 8, second platform blade 16 is shown before and after assembly onto fixed housing 21. Preferably, at least one of the platform blade 16 or the fixed housing 21 has an extending protuberance, post or like feature which can be receivably engaged by the other of the platform blade or housing. In a preferred embodiment, fixed housing 21 is preferably constructed to have a latch post 42 adapted to be received within latch post cavity 45 provided in platform blade 16. Latch post 42 may have a hole, notch, protuberance, or other feature formed therein which may be engaged in any convenient manner by the platform blade 16 so that platform blade 16 becomes releasably locked in place for use.

In a preferred embodiment, latch post 16 has a notch which defines latch surface 51 and stop surface 52. Platform blade 16 has a latch member 48, best seen in FIGS. 11A–11A, having a latch body 50 constructed with surfaces 53 and 54 for engaging latch surface 51 and stop surface 52 respectively. Generally transverse to latch post cavity 45, platform blade 16 has a latch body cavity 56 having an opening towards upper surface 57 of platform blade 16 for receiving latch body 50 of latch 48.

Latch 48 is preferably constructed to engage and disengage latch post 42 by manual rotation of latch knob 49. Latch body 50 includes cylindrical portion 55 which provides for controlled rotation within latch body cavity 56. Latch body 50 may be biased towards the engaged position shown in FIG. 8 by way of any suitable spring element. Preferably, latch post 42 is provided with an angled tip 43 having a lead-in angle 44 which allows angled tip 43 to slide against second engaging surface 54 as latch post 42 begins to be received within latch post cavity 45. As latch post 42 is advanced further within latch post cavity 45, angled tip 43 causes latch 48 to rotate out of the way about cylindrical portion 55. Near the end of the advancement of latch post 42 within latch post cavity 45, the angled tip is advanced beyond latch body 50, and latch 48 (which is biased towards an engaged position) rotates into the engaged position with second engaging surface 54 biased against stop surface 52.

With latch 48 and latch body 50 snapped into the engaged position, any separating force encountered between platform blade 16 and fixed housing 21 is resisted by action of first engaging surface 53 against latch surface 51. With this configuration, the reaction force at first engaging surface 53 is advantageously borne by latch body 50 primarily in compression. Thus, since the loading is primarily compressive in nature a high strength material is not required, and latch 48 can be made from standard engineering polymers, for example, such as polycarbonate.

When it is desired to remove platform blade 16 from drive 12, the operator simply turns latch knob 49, causing latch body 50 to be placed in a disengaged position relative to latch post 42. With latch 48 disengaged, latch post 42 of fixed housing 21 is free to be removed from latch post cavity 45 of platform blade 16. As is apparent from the Figures, a mirror image of the latch assembly described with reference to platform blade 16 and fixed housing 21 is provided to releasably attach platform blade 14 to moveable housing 22.

When the retractor assembly is used to gain access to the thoracic cavity, a good deal of force must be generated to create the desired opening. For example, a separating force in excess of 100 pounds may be required to be generated at each engaging member 18 to achieve the desired separation of a particular sternum. Such loads must be carried by the engaging members and transmitted to drive 12 by way of platform blades 14 and 16. Since platform blades are preferably made from a suitable engineering polymer (for example, a glass filled thermoplastic polyurethane resin), it may be desirable to provide a reinforcing member for each of platform blades 14 and 16 to ensure that platform blades 14 and 16 will not break or otherwise rendered inoperable as a result of the loads encountered during use.

Although the reinforcing members may be a permanent or removable members within the platform blades themselves, the reinforcing members are preferably one or more substantially rigid members extending from each of the fixed housing 21 and the moveable housing 22. In a preferred embodiment, fixed and moveable housings 21 and 22 have a pin extending therefrom which may be received within a mating cavity within first and second platform blades 14 and 16. The pin operates to spread the load developed in the mechanism over a larger internal area within the platform blades 14 and 16 and reduces the effective beam length of unreinforced platform blade material subjected to the operating loads. The pin may be straight pin 40 illustrated in FIG. 3. More preferably, fixed and moveable housings 21 and 22 have tapered pins 40 and platform blades 14 and 16 have mating tapered cavities 41 for receiving tapered pins 40. The tapered construction tends to allow the user to easily align pin 40 with cavity 41 and allows the pins 40 to fit relatively snugly within cavities 41 without significant binding during insertion that could otherwise occur between elongate pins and mating cavities which are designed to be very close fitting.

To provide sufficient load bearing reinforcement, the reinforcing pins 40 are preferably constructed of a substantially rigid material, such as steel, and are preferably at least about 0.75 inches long, more preferably at least about 1.125 inches long, and most preferably between about 1.25 inches to about 2.25 inches long. In a preferred embodiment, reinforcing pins 40 are made from AISI 420 stainless steel having a length of about 1.5 inches, an outside diameter near the housing of about 0.25 inches, and a 2 degree taper angle decreasing towards the free end of the reinforcing pins 40.

In the preferred embodiments just discussed, platform blade 16 can be removed from drive 12 with a substantially straight-line relative motion as indicated by arrow 46. This engagement action not only provides for simple and intuitive assembly in the operating room, but also represents a significant safety feature. Under certain rare circumstances, for example where the drive through neglect or misuse has become sufficiently damaged during use that it is unable to close and disengage from the sternum, an extremely dangerous situation can be created for the patient. In such exigent circumstances, the configuration described above may allow the drive to be separated from the in situ platform blades by releasing the latches and applying a sufficient amount of force in the direction indicated by arrow 46. Once the drive has been removed, the detached platform blades may be easily removed from the patient.

In addition to engaging members 18, detachable platform blades 14 and 16 may incorporate a wide variety of additional features which enhance the performance of the retractor system. For example, one or both of platform blades 14 and 16 may have mounting features to which various instruments used during the procedure can be secured. In the case where a stabilizer is to be secured to a retractor for operating on a beating heart, it is critical to minimize or substantially eliminate the amount of flex and motion attributable to each component and each connection between each component, from the component engaging the beating heart to the component which provides the sternal attachment. To this end, the engaging features 18 which engage the sternum are preferably part of a unitary platform blade structure which also includes mounting features to which a stabilizer and other instruments can be mounted. Since the mounting features and the sternal engaging features are part of the same component, and therefore there is no mechanical connection between the two, the stability of an attached instrument against the forces of a beating heart is greatly improved.

In a preferred embodiment, each of first and second platform blades 14 and 16 include mount features in the form of rails. The rails allow one or more instruments to be positioned at any desired location along the operable length of the rail. Preferably, the rails are oriented in a direction generally perpendicular to the direction of separation, in this case perpendicular to bar 15. The rails may be a recessed feature within the body of platform blades 14 and 16. More preferably, the mounting rails extend upwardly from the body of platform blades 14 and 16.

Referring to FIGS. 7–9, right platform blade 16 has rail 60 extending over at least a portion of the length of platform blade 16. Rail 60 may have a top portion and a bottom portion having a narrowed region adjacent said top portion. In one embodiment, rail 60 preferably has a T-shaped cross-section. The T-shaped configuration has a top portion 61 and a narrowed portion 62, thus forming mounting tabs 63 and 64 which can be gripped by a number of appropriately constructed mounts.

The rail may be straight, curved, or a combination of straight and curved portions. Preferably, at least a portion of the T-shaped rail is curved in a manner which more closely follows the profile of the access or incision site (as seen for example, see FIG. 45). In a curved rail configuration, instruments extending perpendicular to a generally central axis 67 of rail 60 will naturally point more towards a central area between the platform blades 14 and 16, and thus may require less positional adjustment or manipulation from their normal, natural or beginning position. In addition, all or a portion of top portion 61, and more specifically mounting tabs 63 and 64, may be tilted or angled inwardly at an angle 65 as shown.

Platform blade 16 may be also be provided with a number of suture holders or stays which can be used to organize or capture various sutures used in the course of a particular surgery. Since certain sutures are placed near the beginning of a CABG procedure, such as pericardial sutures used to position the heart, the placement of the suture stays in a manner which does not interfere with subsequent procedures and instruments is an important aspect of the present invention. Preferably, the suture stays are positioned such that placing and manipulating the sutures or the various instruments and instrument mounts employed during surgery can be accomplished without interfering with each other. Preferably, the location of the suture stays position the sutures below the level of the mounting tab 63 and 64 so that a mating instrument mount may traverse the entire operable length of rail 60 without interfering with the sutures.

Rail 60 may have one or more grooves, channels, slots or passageways for receiving a suture. In addition, a suture lock may be provided in the rail or elsewhere on platform blade 16 so that the suture may be fixed in place. To accommodate the use of pericardial sutures, which are often subjected to a significant amount of tension when used to position the heart, the suture locks must be adapted to hold the suture material even while under a significant amount of tensile loading.

In a preferred arrangement for organizing and locking sutures, and in particular tensioned pericardial sutures, rail 60 has at least one open slot or passageway formed therein for receiving the free end portions of a surgically placed suture. The passageways preferably extend across rail 60 and have a depth which allows the suture to lay at an elevation sufficiently below mounting tabs 63 and 64 so as not to interfere with an instrument mount sliding along rail 60. In a preferred embodiment the passageways extend through at least a portion of narrowed portion 62. Thus, the height 66 of narrowed portion 62 may be selected not only to provide sufficient space for a desired instrument mount to attach, but also to ensure that mounting tabs 63 and 64 are sufficiently raised above the surrounding features of platform blade 16 so that an instrument mount may be positioned and repositioned along rail 60 without disturbing or disrupting the sutures within the various passageways.

Figure 10:
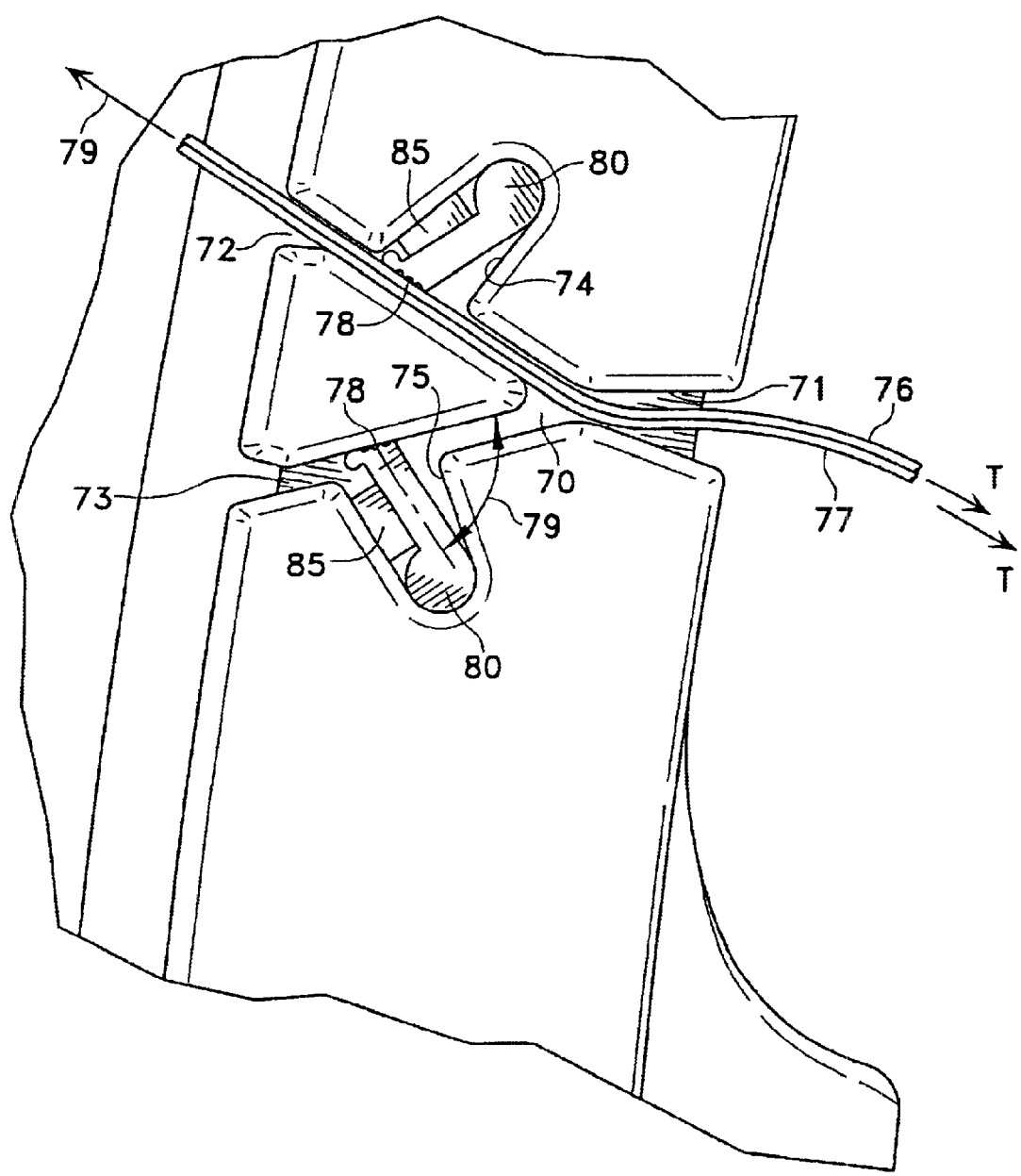
FIG. 10 is a partial top view illustrating a preferred suture stay arrangement associated with a platform blade.

The passageways may be a single channel for receiving both free ends of a surgically placed suture or each end may have a separate channel. In a preferred embodiment rail 60 has a number of bifurcated channels 70 at predetermined intervals along its length. Referring to FIG. 10, bifurcated channel 70 has a single entrance channel 71 which bifurcates into first and second exit channels 72 and 73. Entrance channel 71 and either one of exit channel 72 or 73 can be used in the same manner as a single channel, with both free ends 76 and 77 being routed together. Alternatively, both suture ends may be received within entrance channel 71 and then separated, one end within exit channel 72 and one end within exit channel 73.

A means for clamping the suture against movement within the suture channels may be provided on any of entrance channel 71 or exit channels 72 or 73. Preferably, suture locks are provided on each exit channel 72 and 73. This allows the surgeon to positively identify and unlock a desired suture end for further tension adjustments or other manipulation without unlocking or loosening the other end of the suture. In addition, placing each suture end 76 and 77 in separate exit channels 72 and 73, each with a dedicated suture lock, increases the maximum amount of tension that can be applied to a given suture. Exit channels 72 and 73 may have recesses 74 and 75, respectively associated therewith for receiving a suture lock adapted to secure the suture material within the channels.

A preferred suture lock 80 is illustrated in FIGS. 10 and 12. Suture lock 80 has a relatively rigid body 83 having a fixed or pivot end 81 which allows body 83 to pivot within the mating profile of recess 74 or 75. Pivoting the body 83 about pivot end 81 selectively engages and disengages free end 84 against the wall 78 of exit channel 72 or 1073. Alternatively, suture lock 80 may be made from a more flexible material which, by nature of the elastic properties of the material, tends to flex about its fixed end instead of rotate. In a preferred embodiment, fixed or pivot end 81 is substantially cylindrical and recesses 74 and 75 have mating cylindrical surfaces.

Preferably, the suture lock is angled relative to the wall 78 so that it is self-locking in one direction. That is, the suture ends 76 or 77 (or both) operate on the free end 84 in such a way as to force it towards wall 78, and thus against the suture material, in proportion to the tension, T encountered by suture ends 76 or 77. Thus, within practical limits, the higher the tension the harder free end 84 will press or bite against the sutures placed therein. Conversely, when the suture ends are pulled in the direction indicated by arrow 79, the suture forces tend to pivot body 83 about pivot 81 such that free end 84 is rotated away from wall 84 allowing the suture to move relatively freely. Preferably, angle 79 between body 83 and wall 78 is nominally about 1 degree to about 30 degrees, more preferably about 5 degrees to about 15 degrees, most preferably about 10 degrees. Of course, angle 79 is greater as body 83 pivots to accept a suture placed within the suture channel.

Suture lock 80 may be biased towards the locked position, preferably using a small spring between the suture lock and the recess 75. In a preferred embodiment, a piece of resilient closed cell foam 85 is fixed to body 83 to provide the desired biasing effect. Free end 84 may optionally have a number of teeth or ridges 82 to ensure acceptable traction against the suture material.

Platform blades 14 and 16 may also be provided with soft tissue retainers to help control and retain the incised tissue and fat in the immediate vicinity of the blades. Referring to FIGS. 8 and 9, platform blade 16 includes integrally attached tissue retainer 85. Tissue retainer 85 is generally at a small distance 88 above the top of the engaging members 18. Tissue retainer 85 may be made from a flexible material, such as an elastomer, preferably a polyurethane elastomer having a durometer in the range of about 45 to about 75 Shore D, more preferably about 55 Shore D. In a preferred embodiment tissue retainer 85 is injection molded over the platform blade to form a permanent and inseparable assembly. Tissue retainer 85 may have a raised outer lip 86 and optionally having a plurality of slots 87 formed therein to receive and organize any loose suture ends. Tissue retainer 85 ensures that the tissue surrounding the access incision does not interfere with the operation of rail 60 or the suture holders and also provides a convenient location for attaching surgical drapes of the like without interfering with the operation of the retractor assembly.

Although some of the features of the present invention have been described, for illustration only, with respect to only one of the platform blades 14 and 16, it should be apparent that both platform blades 14 and 16 may have similar or identical features. Although not necessarily so, first platform blade 14 and second platform blade 16 are preferably substantially mirror images of each other.

The retractor assembly just described, provides a simplified drive mechanism for use in conjunction with mufti-featured platform blades. In addition, a number of different platform blades may be provided for use with a single drive, for instance, tailored to different sized anatomy or the specifics of different surgical procedures. Thus, a number of platform blade configurations can be provided to an operating room and, based upon pertinent prevailing clinical factors, the proper configuration can be selected, mounted to drive 12, and used as described above to provide access to a desired location. Also, with the modular configuration new features and advancements can be rapidly incorporated into the platform blades and immediately introduced for use with existing simplified drives already in place in the operating rooms.

The platform blades themselves represent a surgical platform that allows instruments to be mounted and stabilized in virtually any position, even over already placed and secured sutures from the surgical site accessed by the retractor assembly. Described below are preferred instrument mounts for use in conjunction with rail 60 to secure a beating heart stabilizer or other instruments such as heart positioners, saline or medical air blowers, suction devices, surgical clamps, or vessel occluders.

The Instrument Mount

Figure 13:
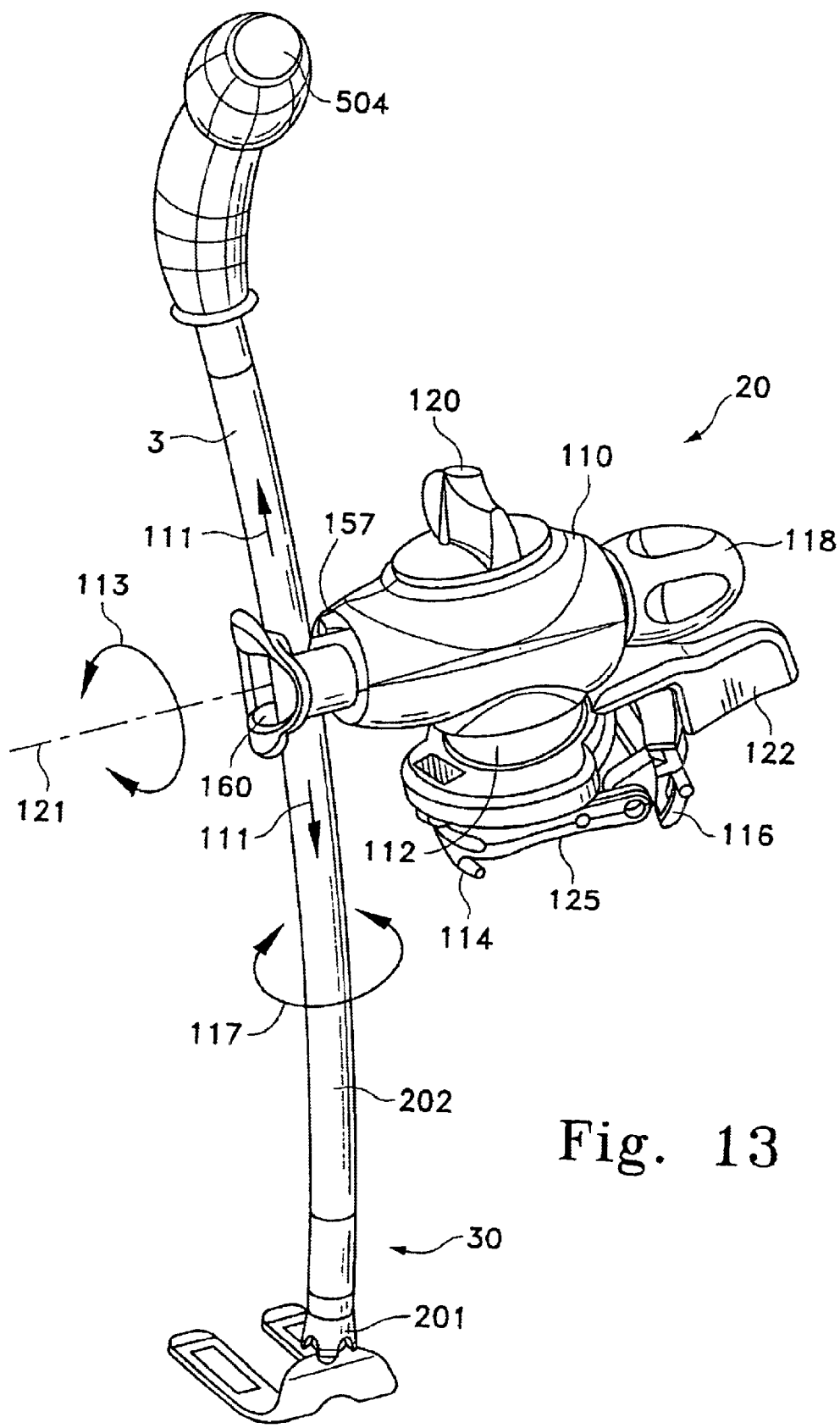
FIG. 13 is a perspective view illustrating an instrument mount assembly according to the principles of the present invention.

Referring to FIG. 13, a preferred instrument mount assembly 20 is shown for mounting an instrument, such as stabilizer assembly 30, to an instrument mounting rail such as described above with respect to rail 60 of platform blades 14 and 16. Mount assembly 20 includes mount base 115 having features to secure mount assembly 20 at a desired position on an appropriately configured mating rail or other suitable structure and includes a stem locking mechanism for controlling and securing an instrument delivery stem in a desired position and orientation.

One important aspect of instrument mount assembly 20 is to provide the necessary degrees of freedom to allow the instrument to be easily maneuvered to whatever position may be required by a particular procedure. As discussed above, an additional aspect with respect to stabilizing the beating heart is to eliminate or minimize the flex or motion attributable to the various components and connections of instrument mount assembly 20. As will be discussed in more detail below, instrument mount assembly 20 is uniquely suited for use in stabilizing the beating heart because it allows sufficient degrees of freedom to easily manipulate the position of an instrument secured thereto, allows the degrees of freedom to be frozen or locked in place and, once locked in place, does not significantly flex or allow movement at any of the articulating or mechanical joints or connections.

Instrument mount assembly 20 provides a number of different controllable articulating joints that, when in a released condition, allows motion in one or more predetermined directions or about one or more degrees of freedom. Although instrument mount assembly 20 may be used to secure any mounting delivery stem configuration from straight substantially rigid shafts to curved substantially rigid tubes to malleable delivery systems to multi-link or segmented ball and socket type delivery stems which are relatively flexible until themselves locked in some manner at each joint along the delivery stem length, it is most advantageously constructed to provide the joints or connections required to position an instrument having a straight, substantially rigid shaft or a curved, substantially rigid tubular member.

In a preferred embodiment, instrument mount assembly 20 has three releasable joints or connections for controlling the location and position of the instrument mount assembly and instrument attached thereto. The mount base may be positioned at a desired location along an appropriate rail and secured by rail grips 114 and 116. The position and orientation of the instrument is then determined by ball joint (or ball and socket joint) 112 between mount base 125 and mount body 110, a rotational joint 157 between mount body 110 and stem hub assembly 160, and a stem clamping mechanism within stem hub assembly 160 which may allow translation, rotation, or both of delivery stem 3 relative to stem hub assembly 160.

Ball joint 112 is preferably of the ball and socket type having 3 rotational degrees of freedom. Rotational joint 157 allows rotation of stem hub assembly 160 about axis 121 as indicated by arrow 113. The stem clamping mechanism allows translation of instrument delivery stem 3 as indicated by arrows 111 as well as rotation about the delivery stem itself as indicated by arrow 117. As will be discussed later, a further ball joint-type connection 201 may be employed between delivery stem 3 and the particular end-effector of the instrument.

Instrument mount assembly 20, having the particular joints and connections identified above, allows all the required areas of the heart to be conveniently and intuitively accessed by a stabilizer connected to one end of a substantially rigid shaft or, more preferably, a curved, substantially rigid tubular member as shown in FIG. 13, for example. Certainly, instrument mount assembly 20 could be provided with more or less degrees of freedom for maneuvering a particular instrument. For example, to add additional degrees of freedom rotational joint 157 could be replaced with a ball joint and to eliminate degrees of freedom delivery stem 3 could be keyed within stem hub assembly 160 or ball joint 112 could be replaced with a rotation only joint. However, it should be noted that excessive degrees of freedom may tend to make instrument adjustment increasingly difficult and cumbersome to control while too few degrees of freedom may not allow the instrument to be easily placed in the desired position or orientation.

In one embodiment, the various joints and connections are locked into a desired position by way of a series of knobs. The degrees freedom provided by ball joint 112 is locked by activation of top mount knob 120. Both rotational joint 157 and the stem clamping mechanism of stem hub assembly 160 is locked in place by the activation of side mount knob 118. Base 125 is locked in position on the rail by activation of mount lever 122. Ball joint 201, as will be discussed in greater detail below, may be locked in position by activation of knob 504. This particular sequence of knobs used to lock down the degrees of freedom associated with instrument mount assembly 20 tends to allow the user greater precision in positioning the instrument because degrees of freedom unnecessary to a particular desired maneuver of the instrument can be locked down. Most commonly, mount body 110 is placed at a desired angle or orientation and then fixed in place by locking ball joint 112, leaving final adjustment to take place using rotational joint 157 and the delivery stem movement allowed by the stem clamping mechanism of stem hub assembly 160.

Figure 14:
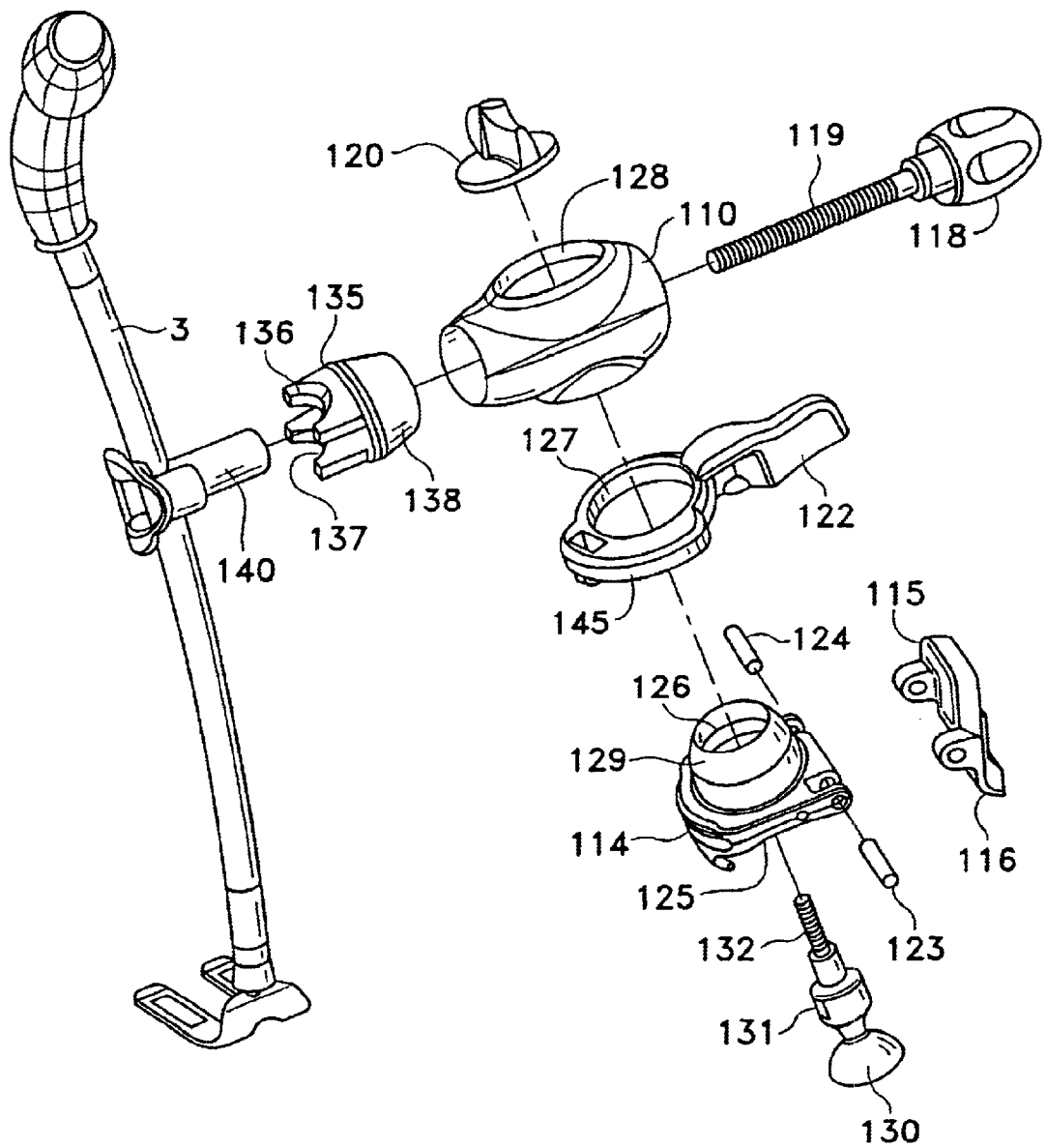
FIG. 14 is an exploded assembly illustration of the instrument mount assembly of FIG. 13.
Figure 20:
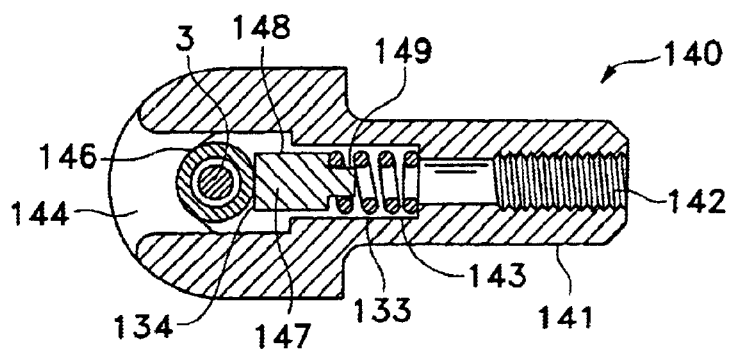
FIG. 20 is a cross-sectional view taken through a horizontal plane of the instrument stem grip of FIG. 19.

FIGS. 14–20 show in greater detail the various mechanisms which lock and release the joints or connections associated with instrument mount assembly 20. FIGS. 20 14 shows an exploded assembly illustration of instrument mount assembly 20. Instrument mount assembly 20, and more specifically mount base 125 to which all the other components are ultimately secured, is preferably constructed to engage and lock in position on a rail or other suitable feature.

Preferably, instrument mount assembly 20 has a fixed rail grip 114 adapted to engage mounting tab 64 of rail 60 and a moveable rail grip 116 adapted to engage mounting tab 63 of rail 60. Rail grips 114 and 116 may generally have hook-like features for gripping mounting tabs 63 and 64. Rail grip 114 is part of mount base 125 and moveable rail grip 116 is part of articulating hinge member 115, which is pivotally attached to mount base 125 by way of hinge pins 123 and 124, or other suitable fastener. Articulation of hinge member 115 and rail grip 116 in clamping manner towards rail grip 114 on mount base 125 effectively clamps mount base 125 onto rail 60 at mounting tabs 63 and 64.

Hinge member 115 may be articulated using any suitable mechanism capable of pivoting hinge member 115 to a closed position and holding it there. In a preferred embodiment, best illustrated in FIGS. 15A–17, hinge member 115 includes follower surface 155 which may be acted upon by any suitable cam device to drive hinge member 115 about hinge pins 123 and 124, thus urging rail grip 116 towards rail grip 114.

In a preferred embodiment, hinge member 115 is articulated by action of cam 145 having cam surface 152 which acts upon follower surface 155. Cam 145 has a center, C about which cam 145 rotates. Preferably, cam 145 has bore 127, having its central axis coincident with center, C. Mount base 125 may have a cam guide 153 around which bore 127 rides for smooth rotation of cam 45 about center, C. Cam surface 152 has a varying radius, illustrated by exemplar radial lines R1, R2, R3, R4, and R5. Thus as cam surface 152 is rotated past follower surface 155, from example from R1 to R2, it pushes the follower surface a greater distance away from center, C, thus causing hinge member 115 to pivot about hinge pins 123 and 124, thus causing rail grip 116 to move closer to rail grip 114.

The varying radius of cam surface 152 may be configured to place hinge member 115, and thus rail grip 116 in a variety of positions. A first portion of cam surface 1525 may be configured such that follower surface 155 biased against cam surface 152 is placed in an position characterized in that rail grip 116 is sufficiently spaced apart relative to rail grip 114 to allow assembly onto a rail or other structure. A second portion of cam surface 152 has an increasing radius such that rotation of cam 145 moves rail grip 116 towards rail grip 114 to an intermediate position. In the intermediate position, rail grip to 116 has been moved close enough to rail grip 114 so that it becomes captured on a rail but remains loose enough to slide along the rail. A third portion of cam surface 152 has an increasing radius such that the rotation of cam 145 moves rail grip 116 further towards rail grip 114 to a completely locked position wherein relative motion between rail grips 114, 116 and the rail is essentially no longer possible.

Cam 145 is generally provided with a handle or lever 122 to allow the user to easily turn cam 145 relative to mount base 125. Cam 145 may be captured onto mount base 125 by operation of retaining hook 150 on cam 145 which rides within exterior groove 151 on mount base 125 on one side, and projection 154 which is engaged below undercut 156 generally opposite to retaining hook 150. Projection 154 also serves to work against undercut 156 to return hinge member 115 to the open position as cam 145 is rotated in the opposite (open) direction. Hinge member 115 preferably has first and second end stops 158 and 159 between which the motion of projection 154 (and thus the rotation of cam 145) is limited. Cam 145 may also have a protective extended portion or cover 163 which shields the area of groove 151 when assembled over mount base 125.

Figure 15A:
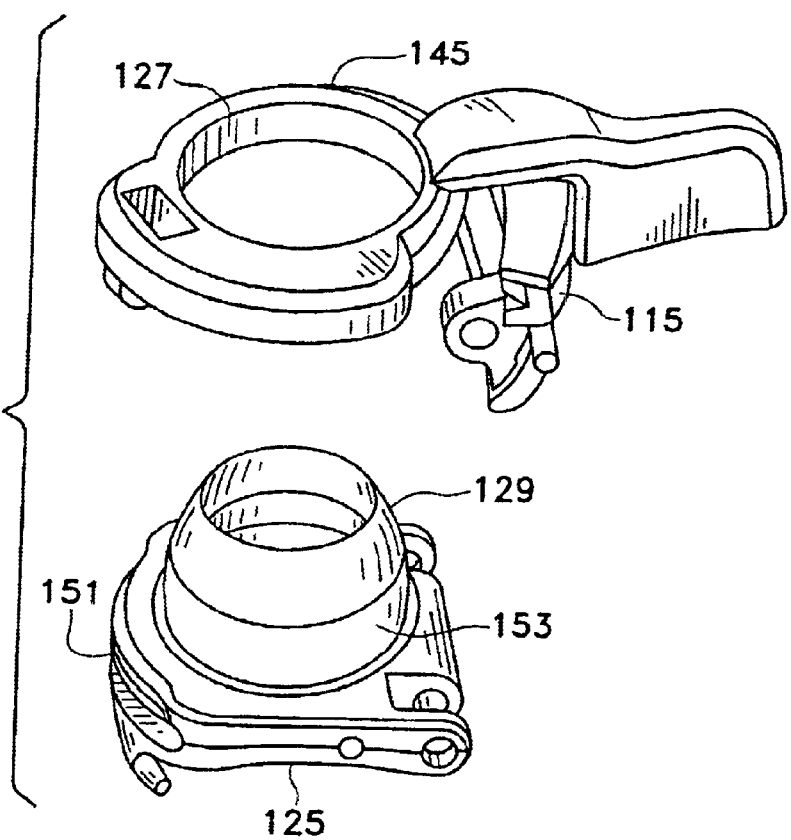
FIGS. 15A and 15B are perspective views illustrating the assembly of the mount cam to the mount base.
Figure 15B:
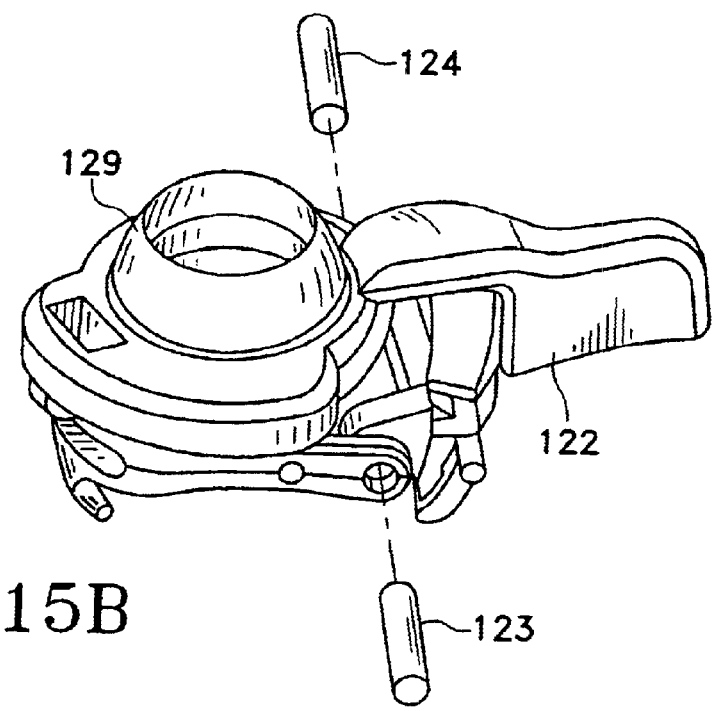
Figure 16A:
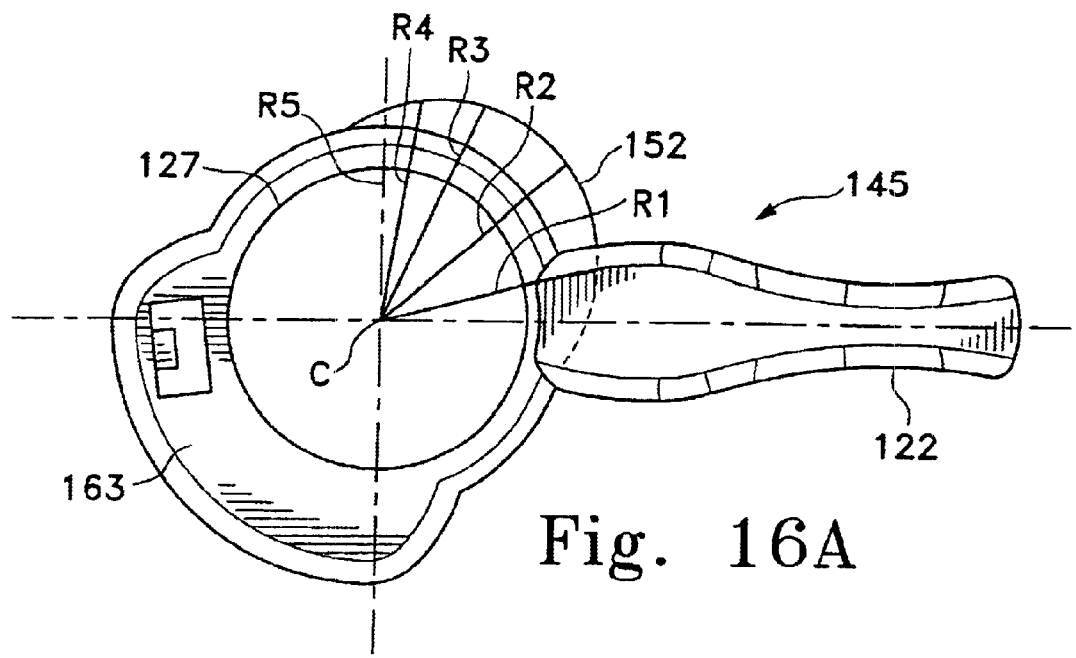
FIGS. 16A and 16B are top and front plan views, respectively, illustrating a preferred mount cam.
Figure 16B:
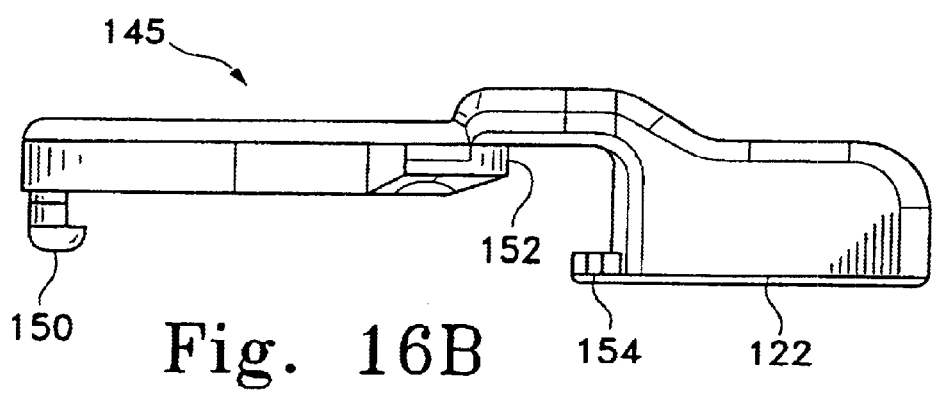
Figure 17:
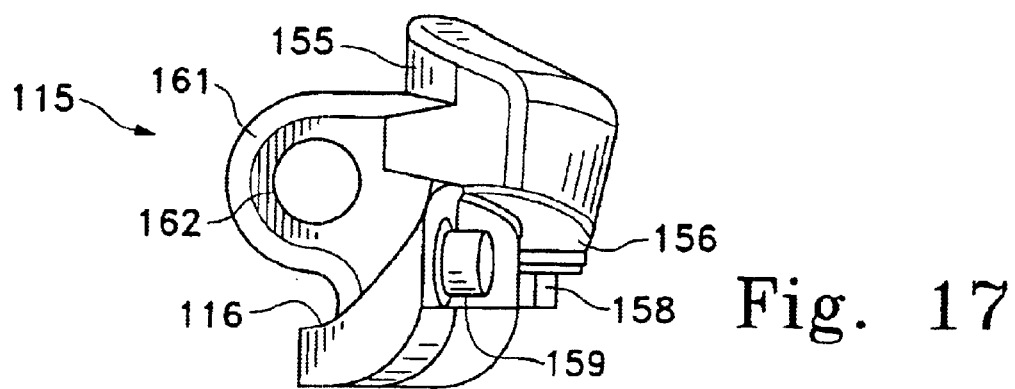
FIG. 17 is a front plan view illustrating a preferred mount hinge.
Figure 18:
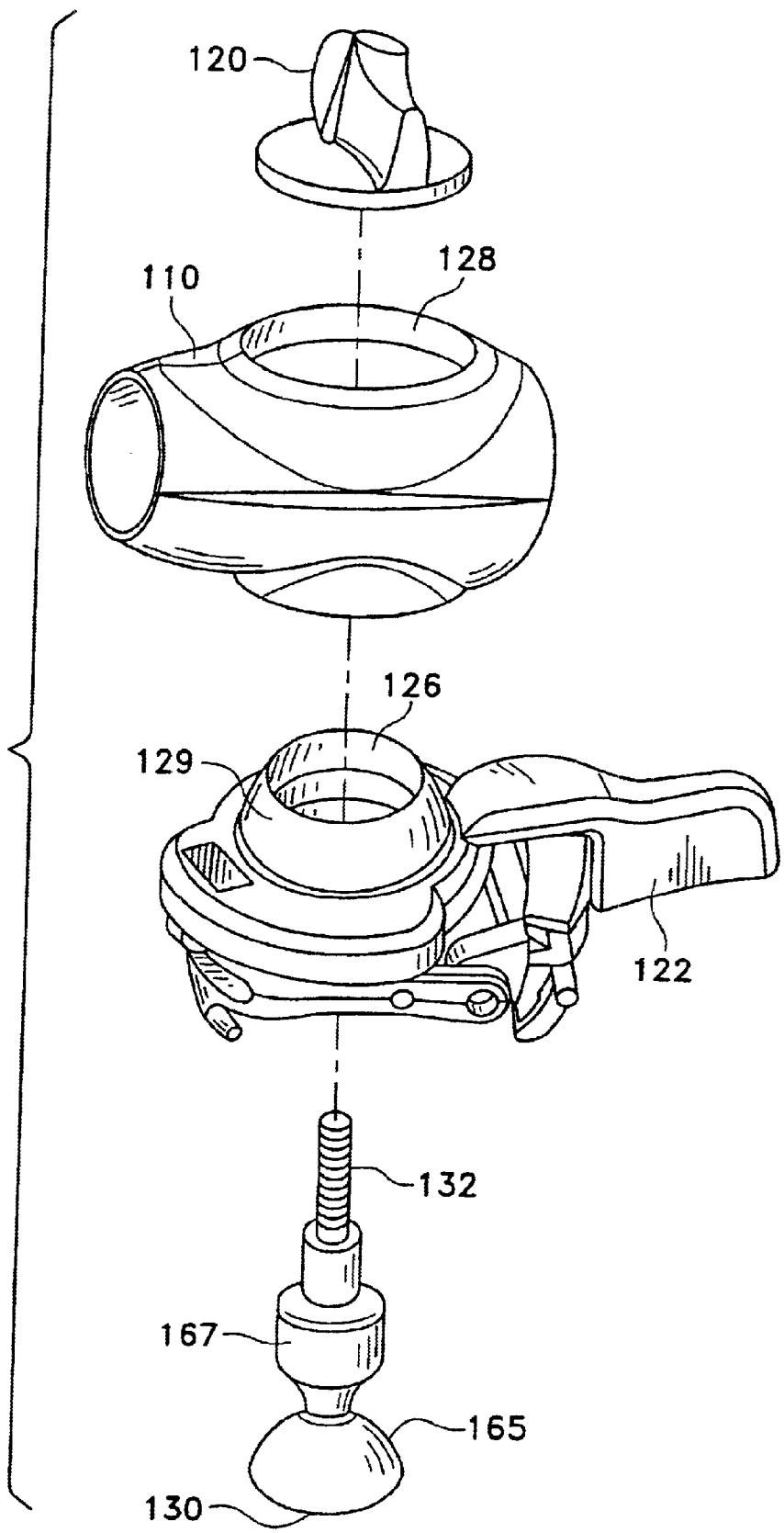
FIG. 18 is an exploded view illustrating the assembly of the mount body to the mount base.

The assembly of cam 145 and hinge member 115 to mount base 125 is illustrated in FIGS. 15A and 15B. Cam 145 is placed in position relative to hinge member 115 with projection 154 in place below undercut 156. In roughly that position, cam 145 and hinge member 115 are brought over mount base 125 until bore 127 is properly seated over cam guide 153 and retaining hook 150 is positioned within groove 151. Pins 123 and 124 are then pressed in place through holes provided in both mount base 125 and hinge member 115.

Ball joint 112 is generally created between ball 129 provided at the top of mount base 125 and a socket or mating cavity within mount body 110 adapted to receive at least a portion of ball 129. Preferably ball 129 includes a generally spherical portion, although other curved shapes providing the desired degrees of freedom may also be suitable. Base post 130 extends vertically upward through bore 126 of mount base 125 and vertical passageway 128 of mount body 110 until enlarged end portion 130 become biased against mount base 125. Top mount knob 120 may then be threaded onto threaded shaft 132 whereby mount base 125 and mount body 110, with ball 129 received within mount base 125, becomes captured between top mount knob 120 and enlarged end portion 130. Continued tightening of top mount knob 120 over threaded shaft 132 forces ball 129 harder against mount body 110 until the friction between mating surfaces on ball 129 and mount body 110 become so great as to effectively resist any relative movement, thus locking ball joint 112.

Figure 19:
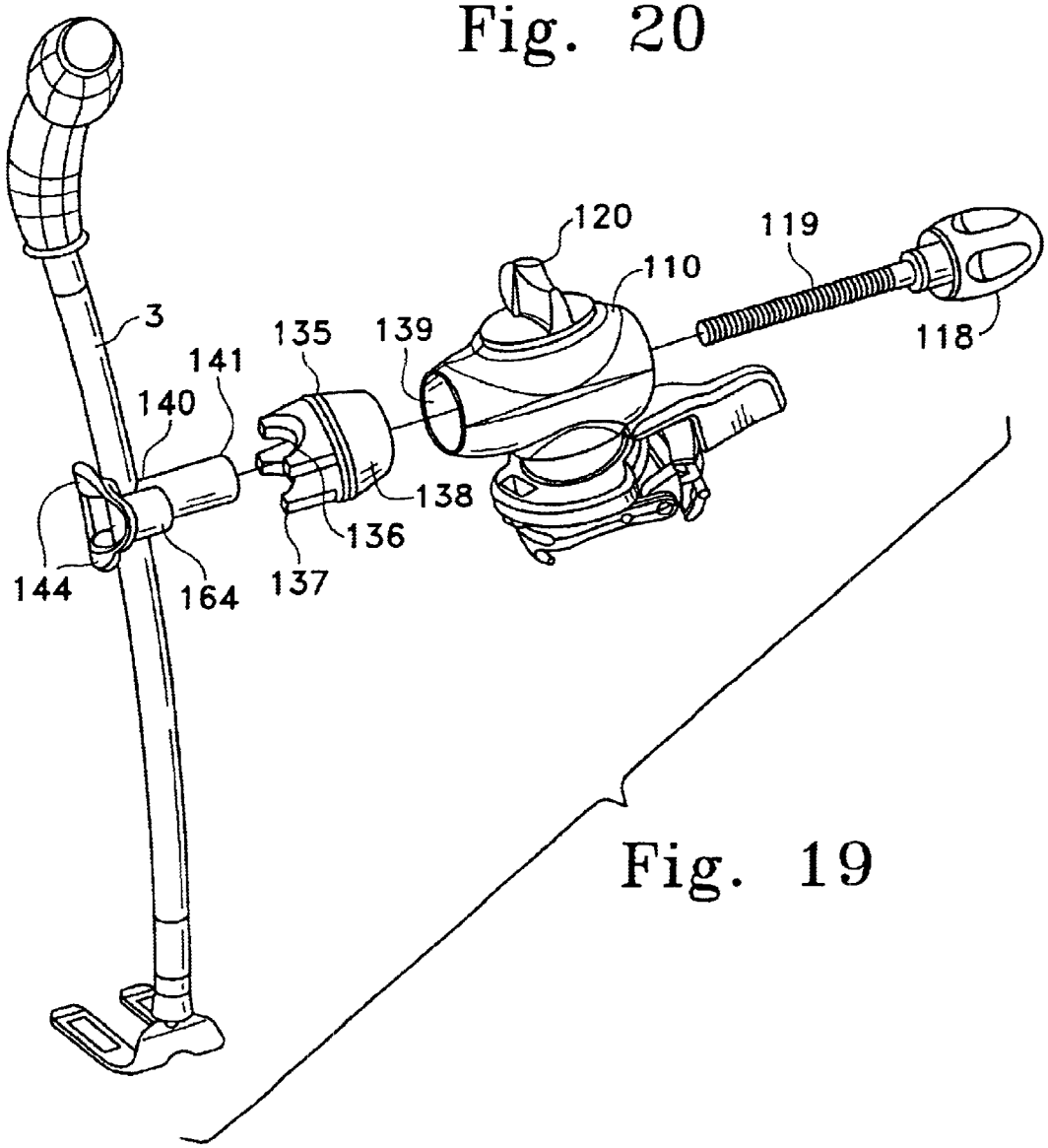
FIG. 19 is an exploded view illustrating the assembly of the instrument clamp to the mount body.

The assembly of rotational joint 157 and stem hub assembly 160 are shown in FIG. 19. Rotational joint 157 is in the form of a conical clutch formed between frustoconical surface 138 of clutch member 135 and mating frustoconical surface 139 in mount body 110. Stem hub assembly 160 is generally formed as upper and lower stem locks 136 and 137 are advanced over stem grip 140 and against instrument delivery stem 3 which is positioned between stem locks 136 and 137 and outer stem guide 144. As clutch member 135 is received over the outside diameter of grip housing 141 of stem grip 140 tang 164 becomes engaged between upper stem lock 136 and lower stem lock 137 thereby preventing relative rotation between clutch member 135 and stem grip 140.

Side mount knob 118 having threaded shaft 119 extends through mount body 110 (and consequently through transverse bore 131 in central portion 167 of base post 130), clutch member 135 and into interior threads 142 within grip housing 141 of stem grip 140. Tightening of side mount knob 118 clamps the assembly together. Thus, translation and rotation of instrument delivery stem 3 is prevented as stem grip 140 and clutch member 135 are forced together to clamp or trap instrument delivery stem 3 between stem locks 136 and 137 and outer stem guide 144. Also, relative rotation between frustoconical surface 138 of clutch member 135 and mating frustoconical surface 139 in mount body 110 is prevented as clutch member 135 is forced against mount body 110. One or both of frustoconical surface 138 and mating frustoconical surface 139 may include a number of teeth, ridges, or other features to prevent rotation when clutch member 135 is forced against mount body 110.

So that the delivery stem does not become too loose as side mount knob 118 is loosened, a minimum amount of friction between instrument delivery stem 3 and the clamping surfaces 146 of outer stem guide 144 is preferably maintained by providing a biasing load against delivery stem 3. Referring to FIG. 20, stem biasing member 147 is provided within stem grip 140 to maintain a biasing load against delivery stem 3. Stem biasing member 147 has a first portion 148 which slides within counterbore 143 in stem grip 140. Stem biasing member 147 may optionally have a second portion 149 having external dimensions sized to be received within the inside diameter of compression spring 133. Compression spring 133 urges end 134 of stem biasing member 147 against delivery stem 3 to force delivery stem 3 against clamping surfaces 146. The amount of force is selected to allow instrument delivery stem 3 to be easily positioned by hand but would generally not allow instrument delivery stem 3 to slide relative to stem grip 140 under only its own weight.

Figure 21:
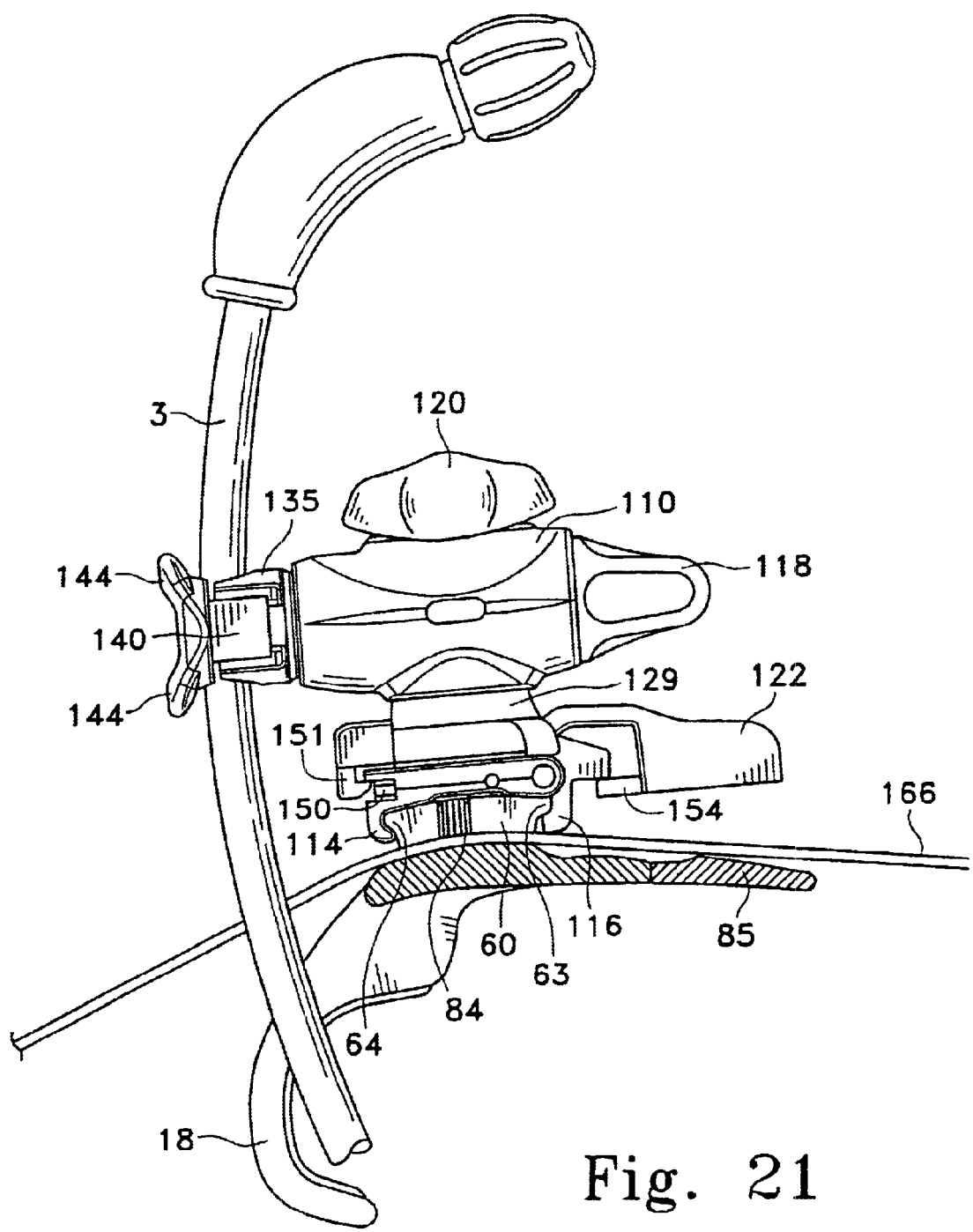
FIG. 21 is a front plan view showing an assembled instrument mount operably positioned on a platform blade according to the principles of the present invention.
Figure 22A:
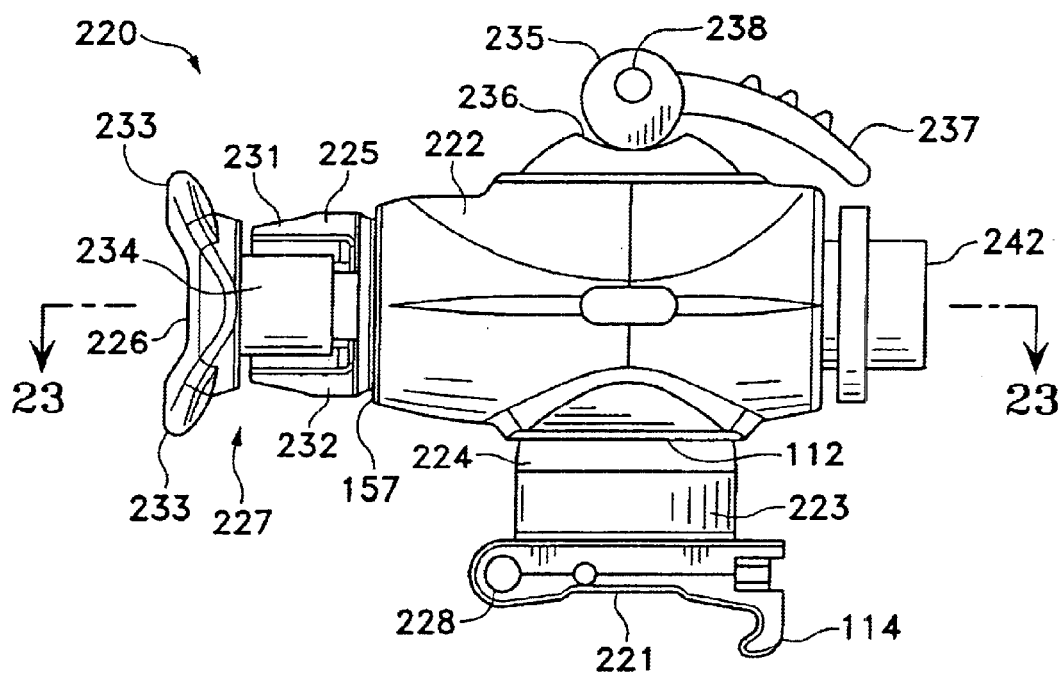
FIGS. 22A and 22B are front and top plan views, respectively, of an alternate instrument mount assembly according to the principles of the present invention.
Figure 22B:
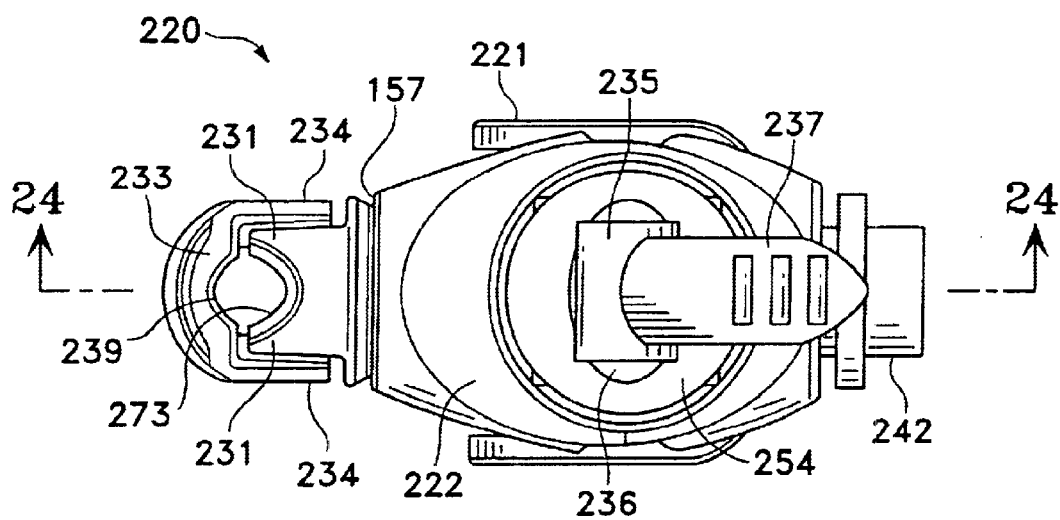
Figure 23:
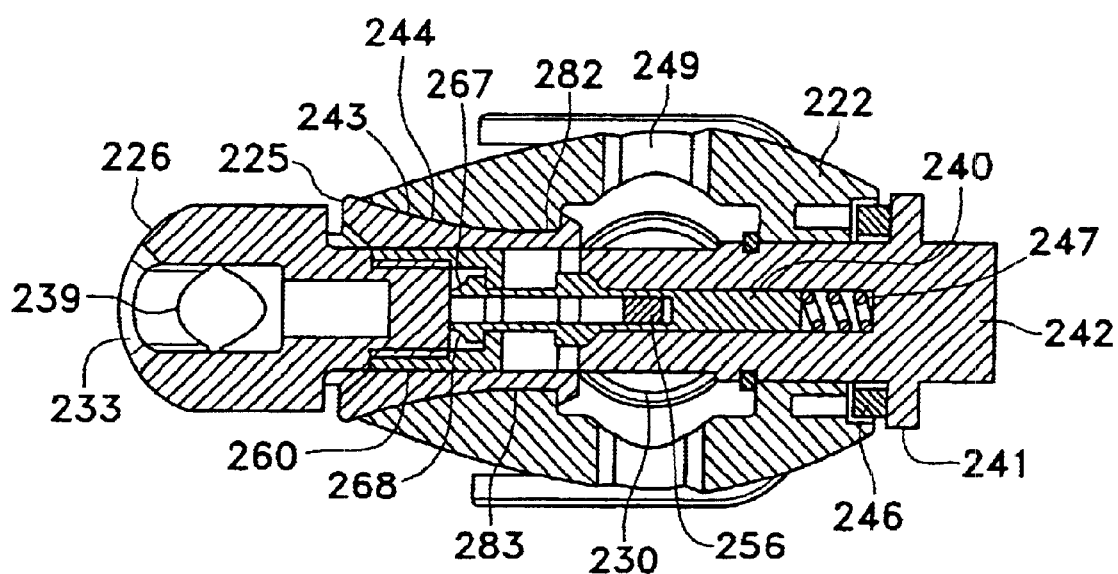
FIG. 23 is a cross-sectional view taken along line 23—23 as shown in FIG. 21.

Referring to FIG. 21 a preferred instrument mount assembly 20 is shown fixed to a preferred platform blade 16 having rail 60. As discussed above, rail 60 has mounting tabs 63 and 64 over which rail grips 114 and 116 may be secured. Instrument mount assembly 20 can be positioned, maneuvered, and removed virtually anywhere along rail 60 without disturbing suture 166 locked in place by free end 84 of suture lock 80 below the operating features of instrument mount assembly 20 within any one of the suture channels provided in platform blade 16. In addition, rail 60 is placed in close proximity to engaging member 18 and thus close to the surgical opening into the patient providing a more direct access to the heart by an instrument mounted to instrument mount assembly 20. Since the rail 60 moves in unison with platform blade 16, this relationship between rail 60 and engaging member 18 is maintained no matter how much or how little platform blades 14 and 16 have been spread to create the desired surgical opening.

FIGS. 22A–32 illustrate a preferred embodiment of an alternative instrument mount assembly 220. Preferably, the degrees of freedom available for maneuvering instrument mount 220 is substantially the same as that of instrument mount assembly 20. Instrument mount assembly 220 preferably has ball joint 112 between mount base 221 and mount body 222, a rotational joint 157 between mount body 222, and a stem hub assembly 227 which allows rotation and translation of an instrument delivery stem held between stem grip 226 and clutch member 226 of stem hub assembly 227. Instrument mount assembly 220, however, has a different mechanism for controlling or locking the various joints and connections and may also provide a means for releasing and removing the delivery stem from the bulk of the remainder of instrument mount assembly 220.

As just mentioned, the joints and connections themselves are quite similar between instrument mount assemblies 20 and 220. As before, ball joint 112 is a ball and socket configuration created between generally spherical ball 224 provided at the top of mount base 221 and a mating cavity within mount body 222 adapted to receive and slide against at least a portion of ball 224. Rotational joint 157 may be in the form of a conical clutch formed between frustoconical surface 243 of clutch member 225 and mating frustoconical surface 244 in mount body 222. An instrument delivery stem may be clamped in place within stem hub assembly 227 by forcing together stem grip 226 and clutch member 225 thus closing clamp surface 239 of outer stem guide 233 towards V-shaped channels 273 on stem locks 231 and 232.

Instead of locking the joints and connections by way of multiple knobs as described above with respect to instrument mount assembly 20, instrument mount assembly 220 preferably uses a mechanism which releases each of ball joint 112, rotational joint 157, and the stem clamping mechanism of stem hub assembly 227 by activation of a single knob, lever, or other suitable manual interface. Generally speaking, this is accomplished by utilizing the clamping motion required to lock one or more of the joints or connections along a first axis to also lock the remainder of the joints or connections along remaining axes.

In a preferred embodiment, ball 224 of mount base 221 is locked in place relative to housing 222 by operation of base post 230. Base post 230 is assembled through mount base 221 and mount body 222 from the bottom until bottom flange 259 (see FIG. 27) is resisted against mount base 221. At the top of base post 230 is upper link portion 256 having pivot hole 257. Cam 235 is attached through pivot hole 257 at off-center link pivot 238 using a pin or other suitable fastener and is supported by contact surface 236 associated with mount body 222. Contact surface 236 may be an integral feature of mount body 222 or may be in a separate mount body cover 254 which may be selected to have superior wear characteristics.

Figure 24:
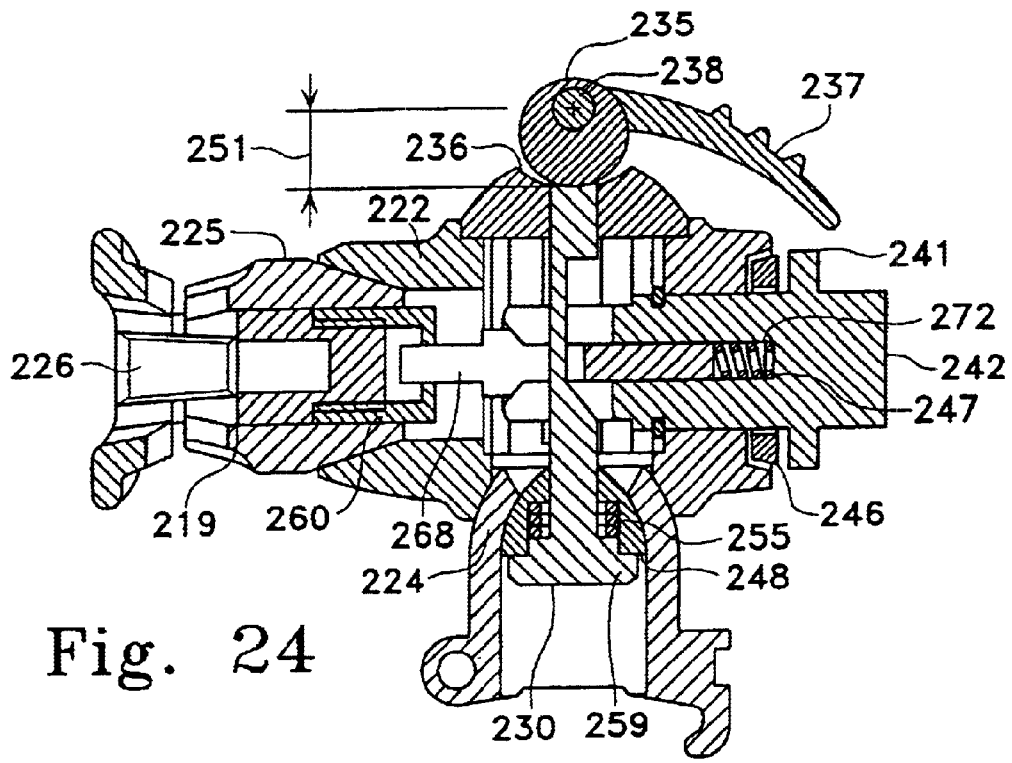
FIG. 24 is an offset cross-sectional view taken along line 24—24 as shown in FIG. 22 illustrating the mount assembly of FIGS. 21 and 22 in the closed position.

With cam 235 in a closed position, as shown in FIG. 24, link pivot 238 is drawn to its maximum distance 251 (or slightly less than the maximum if the cam is constructed to rotate over center) from contact surface 236 thus increasing the clamping force between mount body 222 and ball 224 as the assembly is clamped between cam 235 on the top and bottom flange 259 on the bottom. With cam 235 in the closed position, ball joint 112 is effectively locked.

Figure 25:
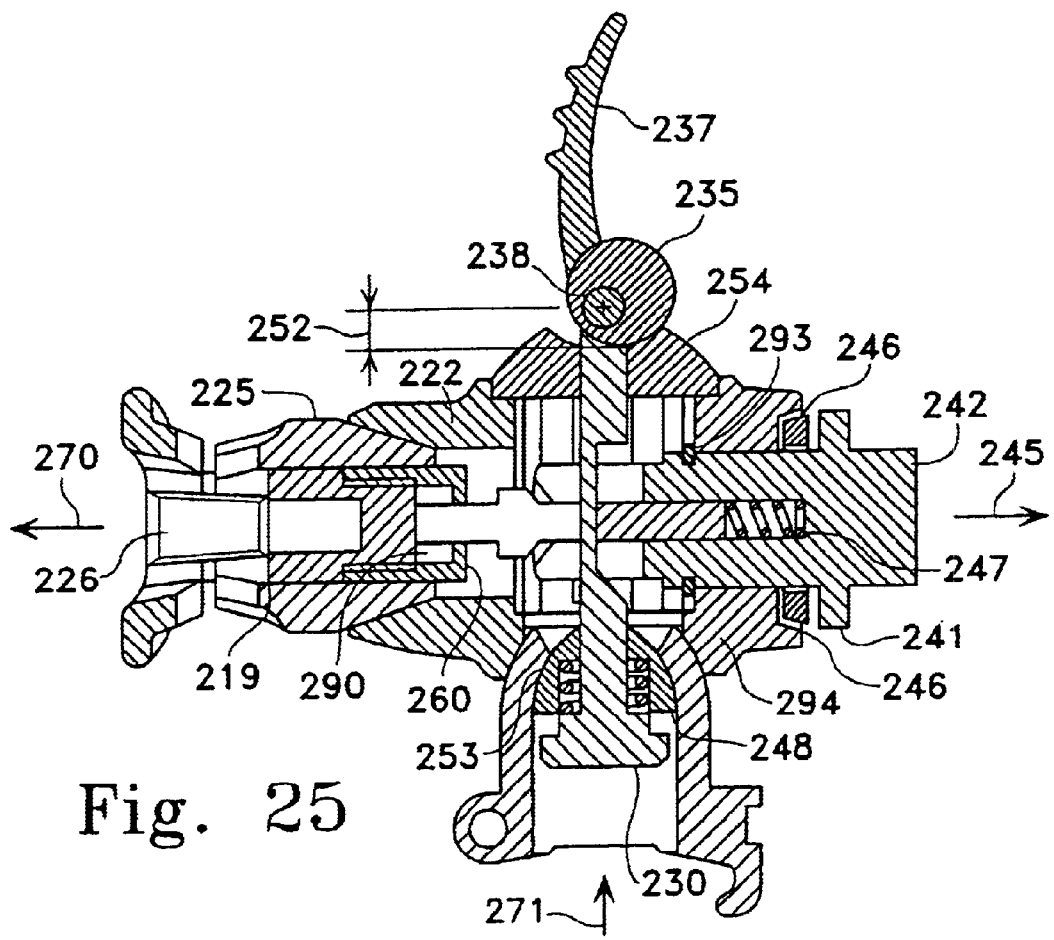
FIG. 25 is an offset cross-sectional view illustrating the mount assembly of FIGS. 21 and 22 in the open position.
Figure 30:
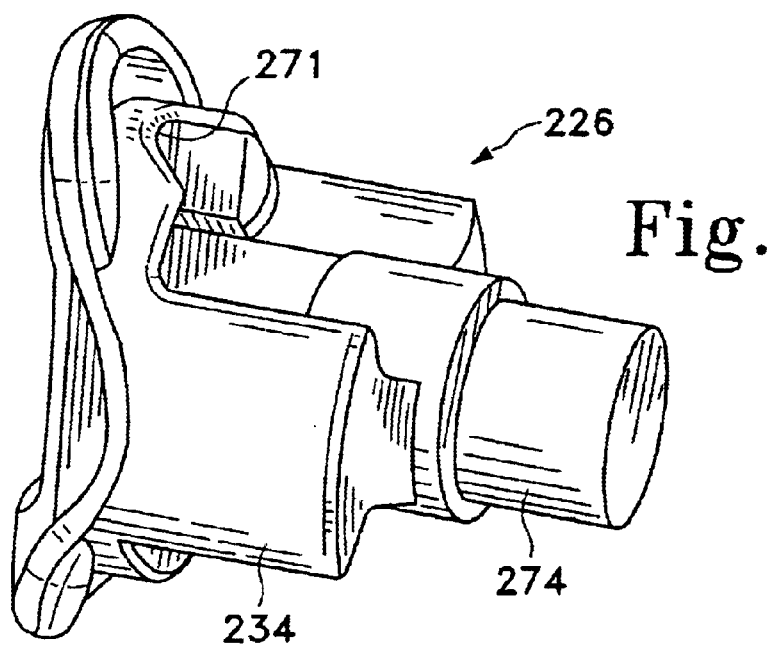
FIG. 30 is a perspective view of a preferred instrument mount stem clamp.
Figure 32:
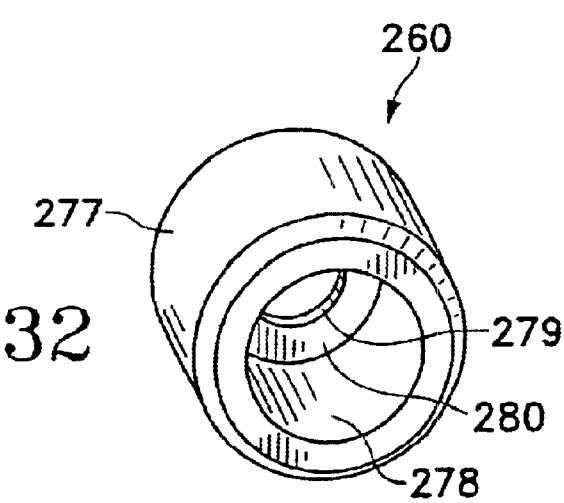
FIG. 32 is a perspective view of a threaded collar associated with the instrument mount stem clamp.
Figure 31:
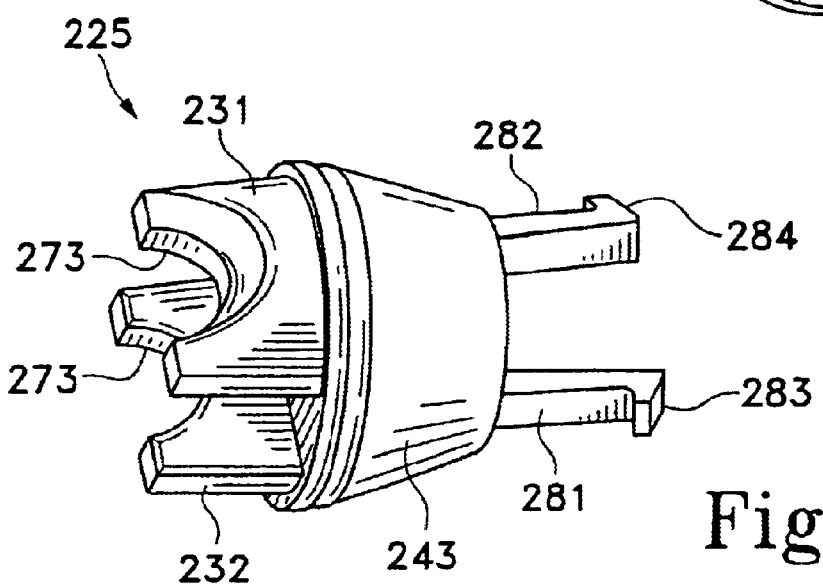
FIG. 31 is a perspective view of a preferred instrument mount conical clutch.
Figure 33:
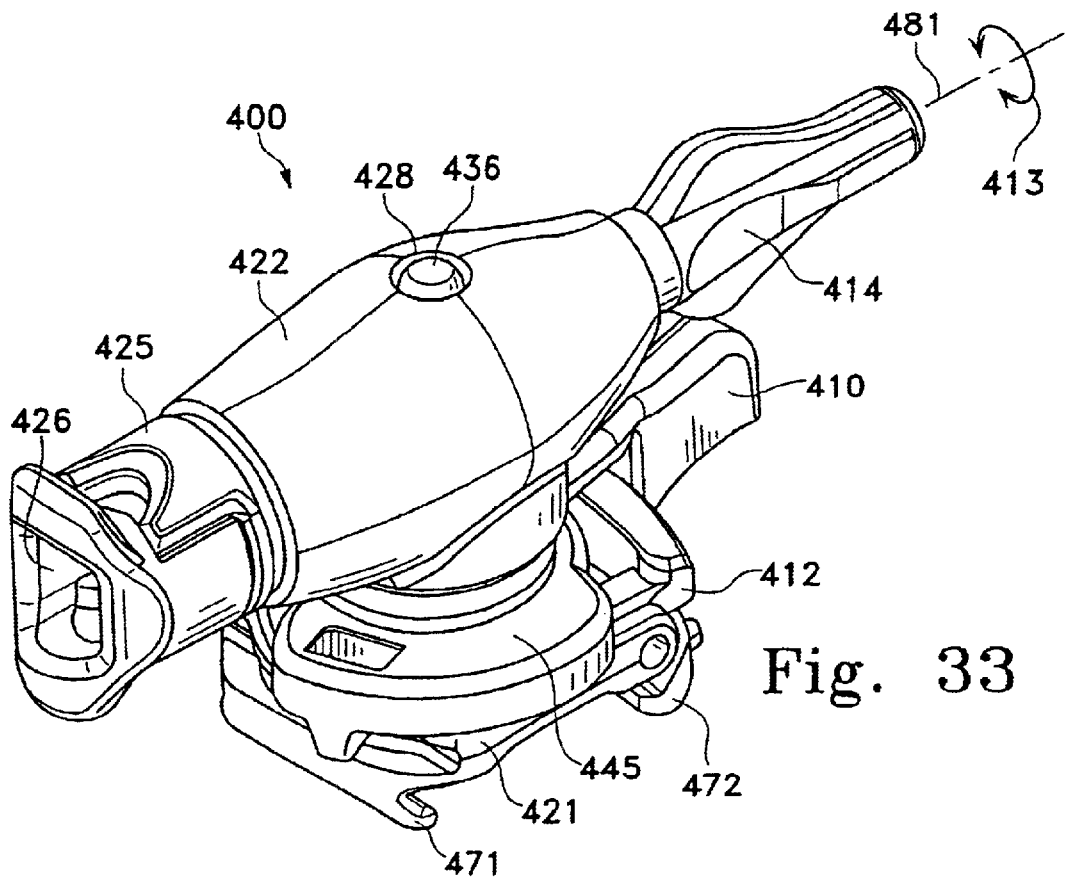
FIG. 33 is a perspective view illustrating an alternative instrument mount assembly having a single knob locking mechanism according to the principles of the present invention.
Figure 34:
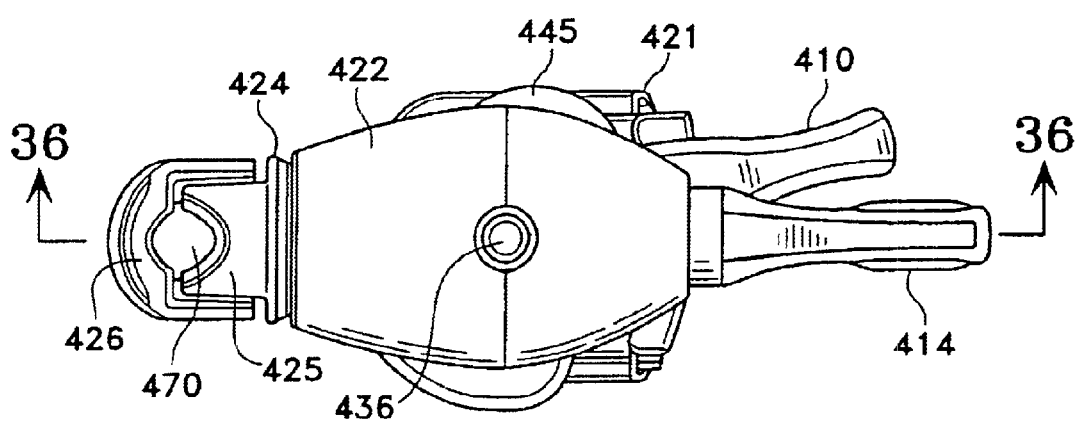
FIG. 34 is a top plan view of the instrument mount assembly of FIG. 33.
Figure 35:
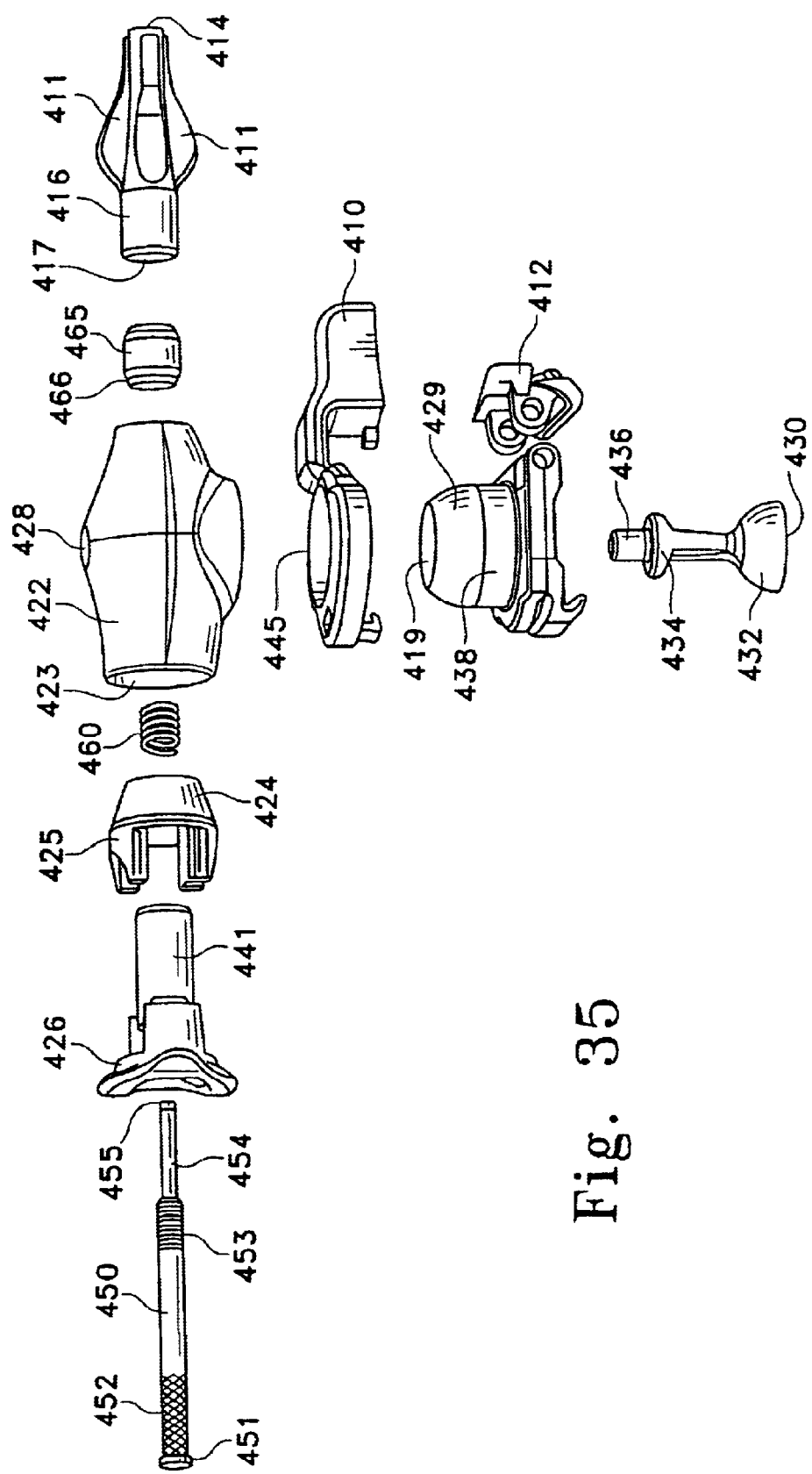
FIG. 35 is an exploded perspective view of the instrument mount assembly of FIG. 33.

By rotating cam 235, by way of handle 237, to an open position as illustrated in FIG. 25, link pivot 238 is withdrawn to a position closer to contact surface 236 at a distance 252, thus reducing or relaxing the clamping forces between mount body 222 and 096 ball 224 of mount base 221. With cam 235 in the open position, the friction at ball 224 is reduced to a level that allows the user to easily manipulate mount body 222 relative to mount base 221.

Mount base 221 may have an insert 253 secured in the bottom thereof against which bottom flange 259 is caused to seat as upper link portion 256 is drawn upwards by operation of cam 235. Preferably, insert 253 includes recess 255 for receiving compression spring 248 captured about base post 230. Compression spring 248 operates between insert 253, and thus mount base 221, and bottom flange 259 to bias base post 230 towards the unlocked position.

That same motion of base post 230, created by operation of cam 235, is preferably also used to lock both rotational joint 157 and the instrument stem clamping mechanism of stem hub assembly 227. Instead of using a threaded shaft to clamp instrument mount assembly along this axis as did the previous embodiment, instrument mount assembly 220 preferably utilizes tie pin 240 which is driven in the direction of arrow 245 causing stem grip 226 and clutch member 225 to be forced together to clamp an instrument delivery stem placed therein and also causing frustoconical surface 243 of clutch member 225 to forced against frustoconical surface 244 in mount body 222.

Tie pin 240 preferably has a generally cylindrical back portion 261 and a front portion which is connected in some manner to stem grip 226. Preferably, the front portion includes forward extending first and second flexible prongs 262 and 263. Cylindrical back portion 261 is slidably received within blind hole 272 of release button 242 and is preferably biased in the unlocked direction indicated by arrow 270 by compression spring 247 positioned within blind hole 272 behind tie pin 240.

Tie pin 240 is preferably driven in the direction of arrow 245 by the movement of base post 230 which is assembled in the space between first and second prongs 262 and 263 of tie pin 240. Preferably, base post 230 has an angled cam or ramp 258 that engages back wall 269 at the base of first and second prongs 262 and 263. As base post 230 is drawn upwards in the direction of arrow 271 by cam 235 from the open position of FIG. 25 to the closed position of FIG. 24, ramp 258 progressively forces back wall 269, and thus tie pin 240, in the direction of indicated by arrow 245.

Tie pin 240, connected at its front end to stem grip 226, locks an instrument delivery stem in place and locks rotational joint 157 in the same manner as did threaded shaft 119 of instrument mount assembly 20. In sum, tie pin 240 urges stem grip 226 towards clutch member 225 and mount body 222. The movement of stem grip 226, having tang 236 engaged between upper and lower stem locks 231 and 232 of clutch member 225, closes together in a clamping fashion surfaces 239 on stem grip 226 and V-shaped channels 273 on clutch member 225. At the same time, stem grip 226 pushes against clutch member 225 to force frustoconical surface 243 against mating frustoconical surface 244 with sufficient force to frictionally lock the surfaces together, thus preventing relative motion therebetween.

The operation of cam 235 has been described as generally moving between an open position, in which the various joints and connections of instrument mount assembly 220 are free to be easily manipulated about their respective degrees of freedom, and a closed position in which the joints and connections resist any relative movement and are thus effectively locked in position. However, the outer cam profile of cam 235 operating against contact surface $2^36$ may be given a profile that has one or more intermediate positions such that link pivot 238 is placed at an intermediate distance from contact surface 236. In an intermediate position, the joints and connections maybe in a stiffened or partially locked state which allows some positional and orientational manipulation with somewhat higher operator forces that the completely released condition. In addition, the action of base post 230 may be such that ball joint 112 becomes fully locked before tie pin 240 has completely locked the remaining degrees of freedom. Thus, cam 235 may have a completely released position where manipulation about all degrees of freedom is easily accomplished, an intermediate position in which only ball joint 112 is fully locked and the remaining degrees of freedom are unlocked or may be partially locked, and final closed position in which all degrees of freedom are locked.

Instrument mount assembly 220 may optionally be provided with a release mechanism allowing stem grip 226, and thus the instrument delivery stem slidably assembled therein, to be released from instrument mount assembly 220 preferably by activation of release button 242. This allows instruments associated with instrument mount assembly 15 220 to be quickly and conveniently removed and replaced or exchanged.

In a preferred embodiment, first and second prongs 262 and 263 of tie pin 240 have first and second projections 267 and 268 which releasably attach tie pin 240 to stem grip 226. Grip housing 274 of stem grip 226 is covered with a sleeve having a deep counterbore 278 and small through hole 279. The depth of counterbore 278 is longer than the exterior of grip housing 274 so as to form internal space 290 (see FIG. 25) when assembled. First and second prongs 262 and 263 can be flexed to position projections 267 and 268 relatively close together for insertion through hole 279 where projections 267 and 268 can then expand apart locking projections 267 and 268 behind surface 280.

Preferably, projections 267 and 268 have lead-ins 291 and 292 which urged projections 267 and 268 together as they are advanced through hole 279 so that stem grip 226 can simply be aligned with lead-ins 292 and 292 and then snapped into place without any further action. Alignment of hole 279 is generally quite simply accomplished as the cylindrical exterior surface 277 of sleeve 260 is slidably received in a substantially coaxial arrangement within center bore 219 of clutch member 225. Clutch member 225 may optionally have first and second flexures 281 and 282 having first and second retaining features 283 and 284 so that it may be snapped in place and thereafter retained within mount body 222.

As mentioned above, stem grip 226 may be released from tie pin 240. To separate tie pin 240, it is necessary to flex first and second prongs 262 and 263 together so that projections 267 and 268 will again be positioned to fit through hole 280. This may be accomplished by providing a raised portion 264 having a ramp 266 on tie pin 240. A sliding member may be advanced up tie pin 240 and over ramp 266 and raised portion 264 thus flexing prongs 262 and 263 inwards. Preferably, the sliding member is a tip portion 289 of release button 242. Tie pin 240 is slidably received within blind hole 272 of release button 242. The internal diameter of blind hole 272 is small enough so that when it is advanced over ramp 266 and/or raised portion 264, prongs 262 and 263 are flexed inwards. Preferably, the entrance to blind hole 272 has an internal chamfer 288 so that ramp 266 is smoothly engaged as release button 242 is advanced.

Release button 242 preferably has a generally cylindrical body 285 which is slidably received within mating bore 294 (see FIG. 25) of mount body 222. Release button 242 is retained in place, and its sliding travel limited, by release button flange 241 on one end and spring clip or e-clip 293 assembled within e-clip groove 286 on the other end. Spring material 246, such as a wave spring washer or foam material, may be disposed between release button flange 241 and mount body 222 to bias release button 242 outwards. Transverse to blind hole 272 tip portion 289 also has a clearance slot 287 through which base post 230 passes.

For clarity only, FIGS. 22A–25 have illustrated instrument mount assembly 220 without hinge member 115 and cam 145 attached. However, hinge member 115 having rail grip 116 is preferably pivotally mounted, with cam 145 in place, by way of pins or the like at hinge mount 228 as described above with reference to instrument mount assembly 20. As discussed above, cam 145 may be rotated about cam guide 223 using base lever 122 to secure the instrument mount to a rail or other suitable structure.

FIGS. 33–37A illustrate a preferred embodiment of another alternative instrument mount assembly 400 which allows the assembly to be locked in a desired position using a single knob. Preferably, the degrees of freedom available for maneuvering instrument mount 400 is substantially the same as that of instrument mounts 220 and 20 as previously discussed. Instrument mount 400 preferably has ball joint between mount base 421 and mount body 422, a ball or a rotational joint between mount body 422 and clutch member 425, and a stem hub assembly which also allows rotation and translation of an instrument delivery stern held between stem grip 426 and clutch member 425.

Instrument mount assembly 400 preferably allows the various articulating or mechanical joints along first axis 481 and second axis 482 to be maneuvered as desired and then locked in a desired position by actuating or operating a single knob, handle, or other user interface. Such multiple-axis arrangements are beneficial in many surgical settings as it is often desirable to have instruments mounted as low as possible about an access opening into a patient while the instruments themselves must be maneuvered and secured at sharp angles relative to the access opening. For example, when securing an instrument for stabilizing the heart during a CABG procedures, the angle between first axis 481 and second axis 482 is preferably less than about 120 degrees, more preferably between about 100 degrees and about 45 degrees, and most preferably about 90 degrees. Further, the ability to lock joints along multiple axes with a single knob tends to reduce the operational complexity of the instrument mount while maintaining the ability to easily maneuver and secure instruments through an access incision within a patient. Thus, this configuration provides a low-profile, flexible, right-angle mount for maneuvering and securing a wide array of surgical instruments.

In a preferred embodiment, the ball joint between mount base 421 and mount body 422 is preferably a ball and socket configuration which may be created between generally spherical ball 429 provided at the top of mount base 421 and a mating cavity or socket 440 within mount body 422 adapted to receive and slide against at least a portion of ball 429. In a preferred embodiment, the ball and socket configuration may also include a generally spherical end 432 on base post 430 which couples with mating surface 447 in the interior of mount base 421. In this configuration, mount base 421 is controlled between spherical end 432 and socket 440 and becomes locked in place as the distance between spherical end 432 and socket 440 is reduced to a dimension which clamps that portion of mount base 421 residing therebetween.

The rotational joint between mount body 422 and clutch member 425 may be in the form of a conical clutch formed between frustoconical surface 423 within mount body 422 and mating frustoconical surface 424 on clutch member 425. An instrument delivery stem may be clamped in place within the open space 470 between stem grip 426 and clutch member 425 by urging stem grip 426 towards clutch member 425. In an alternative configuration, clutch member 425 may simply be the first link of a multi-link support member which may have a series of ball and socket links extending away from said instrument mount and terminating in an end effect or, such as a tissue stabilizer.

Instrument mount assembly 400 preferably has knob 414, the action of which to serves not only to operate upon stem grip 426 and clutch member 425 to lock the degrees of freedom along first axis 481 but also urges spherical end 432 of base post 430 towards socket 440 within mount base 421, thus locking the ball joint along axis 482. Preferably, the locking action along axis 481 is provided by pull pin 450 which has threaded section 453 which may be operably engaged by internal threads within knob 414 or any other suitable cam or mechanism configured to deliver the required axial force to pull pin 450. Pull pin 450 is preferably a generally rigid member, but may also be a section of wire or cable having an appropriate threaded end swaged or otherwise attached thereto. For example, when a multi-link support is coupled to mount body 422 as discussed above, pull pin 450 may be part of or attached to the proximal end of the cable used to lock the links of the multi-link support member.

In a preferred embodiment, pull pin 450 is secured within grip housing 441 of stem grip 426.

Preferably, pull pin 450 is secured within grip housing 441 in a manner which does not allow rotation of pull pin 450 within grip housing 441. In a preferred embodiment, pull pin 450 has knurled section 452 which has an interference fit within bore 442. Grip housing 441 has a counterbore 444 for receiving head 451 of pull pin 450. Head 450 bottoms against the end of counterbore 444 allowing grip housing 441 to be pulled against grip housing 441.

Grip housing 441 of stem grip 426 extends through central bore 420 of clutch member 425. Clutch member 425 is positioned within mount body 422 with frustoconical surface 423 adjacent or against mating frustoconical surface 424 of mount body 422. When the internal threads 418 of knob 414 are advanced along threaded section 453 of pull pin 450 by rotation of knob 414 in the appropriate direction generally indicated by arrow 413 about axis 481, head 451 pulls stem grip 426 against clutch member 425 which is in turn pulled against frustoconical surface 423 of mount body 422. As knob 414 is tightened in this manner, the frictional forces at the stem clamping joint and the conical clutch joint increase in proportion to the axial force delivered by pull pin 450 until the degrees of freedom begin to stiffen due to the increased frictional forces and eventually become functionally locked against further relative motion.

Base post 430 is generally positioned through internal bore 419 of mount base 421 such that spherical end 432 abuts mating surface 447 within mount base 421. Preferably, base post 430 (best seen in FIG. 37A) has an extension or support post 436 which is engaged within a receiving feature, such as opening 428 at the top of mount body 422. Base post 430 has a transverse bore through which pull pin 450 passes. Base post 430 also has a cam surface 435, preferably supported by or associated with upper flange 434. Cam surface 435 may be used to close the position of base post 430 relative to mount body 422 so as to lock the position of mount body 422 relative to mount base 421.

Cam surface 435 may be urged upwards generally along second axis 482 by forcing a suitable thrust surface into engagement with cam surface 435. A suitable thrust surface may be urged in the direction indicated by arrow 483 to contact cam surface 435 causing base post 430 to move upwards in the general direction indicated by arrow 484. The thrust surface is generally associated with knob 414 such that advancement or translation of knob 414 along threaded section 453 of pull pin 450 causes cam surface to move up or down in relation to the position of the mating thrust surface. The thrust surface may be integral with knob 414 or as discussed below provided on a separate element which is engaged by knob 414.

In a preferred embodiment, cam surface 435 is urged upwards by operation of lifter 465 which slides over pull pin 450, preferably over a non-threaded or smooth section of pull pin 450. Lifter 465 may have a contoured, shaped, radiused, or chamfered thrust surface 466 configured to mate with cam surface 435. Knob 414 preferably has guide housing 416 which is sized to fit within mating guide bore 415 of mount body 422. As knob 414 is tightened, and internal threaded portion 418 is urged along threaded section 453 of pull pin 450, guide housing 416 pushes lifter 465 in the direction indicated by arrow 483, thus engaging cam surface 435 with mating surface 466 causing base post 430 to move upwardly towards mount body 422 and socket 440 in the direction generally indicated by arrow 484. As with the other mechanical joints, tightening knob 414 proportionally increases the frictional forces at the socket 440/ball 429 and spherical end 432/mating surface 447 interfaces until they become functionally locked against relative motion.

To eliminate the possibility of the instrument mount assembly becoming disassembled during use, knob 414 is preferably captured on pull pin 450. In a preferred embodiment, pull pin 450 has an extension 454 having an enlarged portion 455. Knob 455 is assembled over extension 454 until enlarged portion 455 is forced past restriction 476. Once snapped in to place, enlarged portion 455 is free to travel within clearance passage 457 but remains captured by operation of restriction 476 even if knob 414 becomes completely disengaged from threaded section 453. Knob 414 preferably has a non-threaded internal bore 417 which is sized to smoothly traverse over both non threaded portions of pull pin 450 as well as threaded section 453 as may be required over the full travel of guide housing 416 and knob 414. Knob 414 preferably has one or more grip ridges 411 to facilitate convenient operation by a user, typically wearing surgical gloves.

This preferred configuration of instrument mount assembly 400 allows the mechanism to perform in a number of ways with only slight modification. For instance, the operation of pull pin 450 and lifter 465 can be configured to have the mechanical joints tighten and lock according in any desirable order or timing preference. In one embodiment, the mechanical stem lock, rotating clutch, and ball joint begin to stiffen generally at the same time. It may be desirable for lifter 465 to be made from a somewhat softer material or initially have a point or line contact with cam surface 435 such that lifter 465 deforms or crushes somewhat as the mechanism is tightened. Lifter 465 may be made from any suitable tough yet relatively soft engineering plastic such as nylon, high density polyethylene, polypropylene, or the like. This allows lifter 465 to stiffen the ball joint initially, and then as knob 414 is tightened further, lifter 465 crushes or deforms so that only modest increases in frictional forces are imparted to the ball joint while the remaining mechanical joints along pull pin 450 are allowed to tighten significantly. Further tightening of knob 414 eventually locks each of the mechanical joints of instrument mount assembly 400.

In a preferred embodiment, it is desirable for the ball joint between mount base 421 and mount body 422 to tighten slightly ahead of the remainder of the mechanical joints. This allows the user to initially manipulate mount body 422 to the desired position or orientation and begin tightening the knob to substantially stiffen or even lock the ball joint and thus mount body 422. The surgeon may then manipulate the instrument to the to desired position and orientation using the degrees of freedom available in the conical clutch and stem clamp. At that point, knob 414 can be further tightened to lock the remainder of the mechanical joints. Knob 414 can be loosened slightly to reposition the instrument if required without disturbing the ball joint. Compression spring 460 may be used to operate against upper flange 434 to pre-load base post 430 upwardly so that a minimum amount of fictional forces are maintained in the ball joint between mount base 421 and mount body 422.

To force base post 430 to clamp at an earlier point as knob 414 is tightened, the lifter may be constructed of a harder material and may have a greater contact area against cam surface 435. FIG. 37B illustrates lifter 490 having a greater contact area for engaging cam surface 435. Lifter 490 has a more extended profile, and may preferably be square or substantially square shaped. The extended profile provides the material for an enlarged surface 492 for contacting cam surface 435. Since lifter 490 is no longer symmetrical about its axis, it may be desirable to key lifter 490 relative to cam surface 435 to ensure proper alignment. Preferably, lifter 490 has one or more ribs or protrusions 494 to engage mating surfaces (not shown) within mount body 422 to ensure surface 492 will be aligned with cam surface 435 as bore 496 rides over pull pin 450.

Instrument mount 400 may be secured to any stable location such as, for example, a rib or sternal retractor or other convenient mounting location which is sufficiently stable to secure the desired instrument. As with the previous instrument mount embodiments, instrument mount 400 is configured to cooperate with a rail or like structure, preferably associated with the retractor used to create the access opening through which an instrument is to be inserted. In a preferred embodiment, hinge member 412 having rail grip 472 is preferably pivotally mounted to mount base 421 by way of pins or the like at hinge mount 462 as described above with reference to instrument mount assembly 20. Cam member 445 may be rotated about cam guide 438 using base lever 410 causing hinge member 412 to urge rail grip 472 towards rail grip 471 on mount base 421, thus facilitating instrument mount 400 to be secured to a rail or other suitable structure.

The retractor and instrument mounts described above can be used to mount and stabilize a great number of instruments for use during surgery. Preferably, the retractor and instrument mounts are used to mount a mechanical stabilizer for stabilizing at least a portion of the beating heart during CABG surgery or the like. Described below are a number of mechanical stabilizer embodiments that are particularly beneficial for stabilizing the beating heart, especially when used in conjunction with the retractors and instrument mounts described above.

Tissue Stabilizers

Once access to the heart is achieved, and the heart is positioned if necessary, a means for stabilizing the beating heart is introduced through the opening created and at least one component of the stabilizing device of the invention is brought into contact with the beating heart. The surgeon then applies a stabilizing force to the beating heart via the stabilizing means which may then be fixed in place by attachment to a fixed support. When a retractor or platform is fixed in an open position to expose the heart, the retractor platform may also provide the stable support structure to which the stabilizing means is affixed. When the position of the stabilizing means is fixed by attachment to a stable support or to the retractor platform, the stabilizing force is maintained for the duration of the procedure.

The structure of the portion of the stabilizing means which contacts the heart may include one or more contact members which exert a stabilizing force on the heart proximate to the site of the anastomosis. A pair of contact members may be plates or rectangular members which are placed on either side of the target coronary artery at the site of the anastomosis and which may have friction means or tissue spreading or compressing apparatus associated therewith. The contact members may also be provided by a platform which may be substantially planar or which may be contoured to fit conformingly on the surface of the heart. The stabilizing means may also include a delivery system or member which may have any suitable construction that allows the working end of the stabilizing means to be positioned and secured as necessary. The delivery system or member may include flexible multi-link constructions, malleable constructions or other delivery stem having several alternative embodiments to facilitate adjusting the position and orientation of the instrument at the surgical site. For example, the delivery stem may be a common shaft or alternatively, a curved tubular member, and may have an adjustable length and the axis of the delivery stem may have at least one ball joint disposed within its length such that the orientation of the delivery stem relative to another structure such as the contact members or stable support may be continuously varied. As is apparent from the description of the several embodiments, each of the individual embodiments described and illustrated herein has discrete components and features which may be readily separated from or combined with the features of any of the other several embodiments.

Referring to FIGS. 38–42, a preferred stabilizer assembly for stabilizing the beating heart is comprised of a foot or base portion 553 attached to a rigid or semi-rigid delivery stem 3, drawn here, for purposes of example only, as a curved tubular member. Base portion 553 typically has one or more contact members 1 adapted to contact the heart adjacent the site desired to be stabilized. The contact members 1 may be substantially planar, may be slightly curved to conform to the shape of the heart, or may be a nonconforming curve to establish contact between only a to portion of the contact member 1and the beating heart. The shape of the contact members may be varied depending on the clinical assessment by the surgeon, the design of the other features of the stabilizing means, or the design of other instruments used to complete the anastomosis. In some embodiments the contact members 1 may have apertures, openings or attachments to facilitate connection with sutures or other devices to achieve the requisite stabilization, occlusion of the target vessel, or exposure of the target vessel. Examples of suitable base portions and contact members can be found, for example, in co-pending U.S. patent application Ser. No. 08/931,158 filed on Sep. 16, 1997, entitled "SURGICAL INSTRUMENTS AND PROCEDURES FOR STABILIZING THE BEATING HEART DURING CORONARY ARTERY BYPASS GRAFT SURGERY," the entirety of which is herein incorporated by reference.

Referring to FIGS. 38 and 39, the proximal end of connecting delivery stem 3 has handle mechanism 468 assembled thereto which, among other things, provides the user with a means for locking an end effect or operably attached to the distal end of connecting delivery stem 3. The mechanism 468 is rotatably secured to the proximal end of the delivery stem 3 and is formed at a selected angle to the delivery stem to permit a surgeon to swivel the mechanism to a preferred position where the knob 504 is more readily accessible to allow quickly locking the delivery stem 3 in the orientation selected. In addition, the angled axis of the knob 504 relative to the delivery stem 3 reduces the tendency of the delivery stem 3 to rotate about its axis when a surgeon applies torque to the knob 504 to lock the associated locking mechanism. The knob 504 is secured to a screw 539 by suitable means such as press fitting, bonding, etc. Right and left handle covers 540, 541 comprise the handle 503 and provide the support for the handle mechanism. When assembled, the covers define generally a cylinder formed with a selected curvature. A secondary inner molding, generally indicated at 542, includes various integrally formed annular walls and shoulders for supporting and containing the knob 504 and screw 539, as well as a cooperating nut 543, and arcuate wedge 544, a stem retaining ring 545, the proximal end of the delivery stem 3, and a proximal end of the translatable push rod 505. The proximal end of the delivery stem 3 includes an annular retaining ring slot 546 which secures the proximal end of the delivery stem 3 within suitable annular walls in the corresponding end of the handle covers 540, 541 when the retaining ring 545, confined by shoulders in the inner molding 542, is snapped into the slot 546 and the covers are assembled. The nut 543 is confined by shoulders in the inner molding 542, and the arcuate wedge 544 is slidably confined by correspondingly arcuate walls 547 also formed in the inner molding.

As may be seen, rotation of the threaded screw 539 within the confined threaded nut 543, causes translation of the screw, pivoting and thus translation of the translatable wedge 544 which abuts the screw, and translation of the push rod 505 which abuts the translatable wedge. As is further described relative to FIGS. 40–42, any tightening or loosening of the screw 539, however slight, will cause a corresponding translation of the push rod 505 into or out of the delivery stem 3.

As depicted in the Figures, the delivery stem 3 and thus the push rod 505, are formed with a slight arcuate configuration, which permits additional degrees of freedom and movement and orientation of the distal end of the delivery stem 3 and thus of the heart contact member 1. Rotation of the delivery stem 3 about the axis of confinement within the stern grip 495 or 495a, moves the distal end of the delivery stem 3 through a circular path while changing the angles through which the contact member 1 can be oriented. This allows a surgeon to conveniently achieve a wider range of positions and orientations of the contact member relative to the patient's heart, while keeping the proximal end of the delivery stem 3 and handle mechanism 468 out of the way as much as possible.

FIGS. 40–42 illustrate an associated mechanism for maneuverably supporting the various embodiments of the contact member 1 and for cooperatively assisting in the quick locking of the contact member by a partial rotation of the knob 504 once the member is positioned. To this end, the distal end of the delivery stem 3 is provided with exterior threads matching interior threads in a ball/socket 548. The distal end of ball/socket 548 is provided with slots 549, whereby the remaining material comprises short extended tips 550 which, when bent in or inwardly formed, form a socket. A ball/post 551 includes a ball at one end and a post at the other. When the mechanism is assembled, the ball/post 551 is inserted into place within the ball/socket 548 with the ball in the socket and the post protruding from the ball socket. A mechanism for providing a preloaded source, such as a compression spring 552, is coupled to the ball/socket 548 abutting the ball. The spring 552 is urged by the distal end of the delivery stem 3 to exert a preloaded or constant minimum force against the ball of the ball/post 551. The post of the ball/post 551 is solidly fixed as by press fitting, welding, etc., to the contact member 1. The distal end of the push rod 505 passes through the spring 552 to abut the ball of the ball/post 551. Thus when the screw 539 is not tightened, the distal end of the push rod 505 exerts a slight pressure against the ball, however the spring 552 maintains a preloaded force against the ball sufficient to maintain the contact member 1 at any orientation set by a surgeon. When the screw 539 is tightened, the push rod 505 is forced against the ball to prevent any further movement of the contact member 1. As may be seen, the contact to member 1 can be tilted to assume many orientations since the narrow center of the post can tilt into any of the four slots 549 in the ball/socket 548. In addition, simultaneous rotation of the curved delivery stem 3 provides surgeon with an even greater variety of orientations of the contact member relative to a patient's heart.

The contact member 1 includes a preferred configuration which improves the size of the area of the heart which is visible to a surgeon while still providing the required suppression of heart movement necessary to enable the efficient construction of the anastomosis. More particularly, the pair of spaced-apart contact members 1 extend from a common base portion 553, which uniquely first extends back away from the tips of the, contact members at the point of attachment to the post, as shown at reference number 554. The spaced contact members 1 then curve downward away from the common base portion 553 and back past the post and away from the delivery stem 3. As may be seen in the FIGS. 40–42, the contact member 1 of this embodiment uniquely is attached to the post on the same surface as the surface that bears against the surface of the beating heart. Since the members 1 separate at the base portion 553 at a point 555 behind the distal end of the delivery stem 3, a surgeon has an unobstructed and thus optimum view of the heart even below the distal end of the delivery stem 3.

The contact members preferably include friction means 556 selectively secured to the bottom surfaces thereof to more securely engage a beating heart. In addition, the tips of the contact members are bent upward in the form of "ski tips" to lessen their impact when the contact members are firmly pressed against a beating heart to suppress the anastomotic site.

Although screw means 539/504/543 is illustrated herein as a locking mechanism to of the handle mechanism 468, it is to be understood that other mechanisms may be employed. For example, a cam/lever mechanism may be attached to a rod which in turn imparts a pivoting movement or translation to a suitable bell crank or pivotable member, which in turn imparts translation to push rod 505 of the delivery stem 3. Thus, locking mechanisms other than those specifically described herein may be used.

The basic configuration as just described with reference to base portion 553 provides the maneuverability necessary to access and stabilize any desired vessel on the surface of the beating heart. However, the exact manner and position in which the stabilizer may be placed relative to the vessel and the surgical techniques preferred by an individual surgeon may vary significantly. Accordingly, there is some potential that certain combinations of stabilizer positioning may interfere somewhat with the preferred surgical technique of a particular surgeon. The embodiments illustrated below with respect to FIGS. 43–45B alleviate any such problems.

Figure 43:
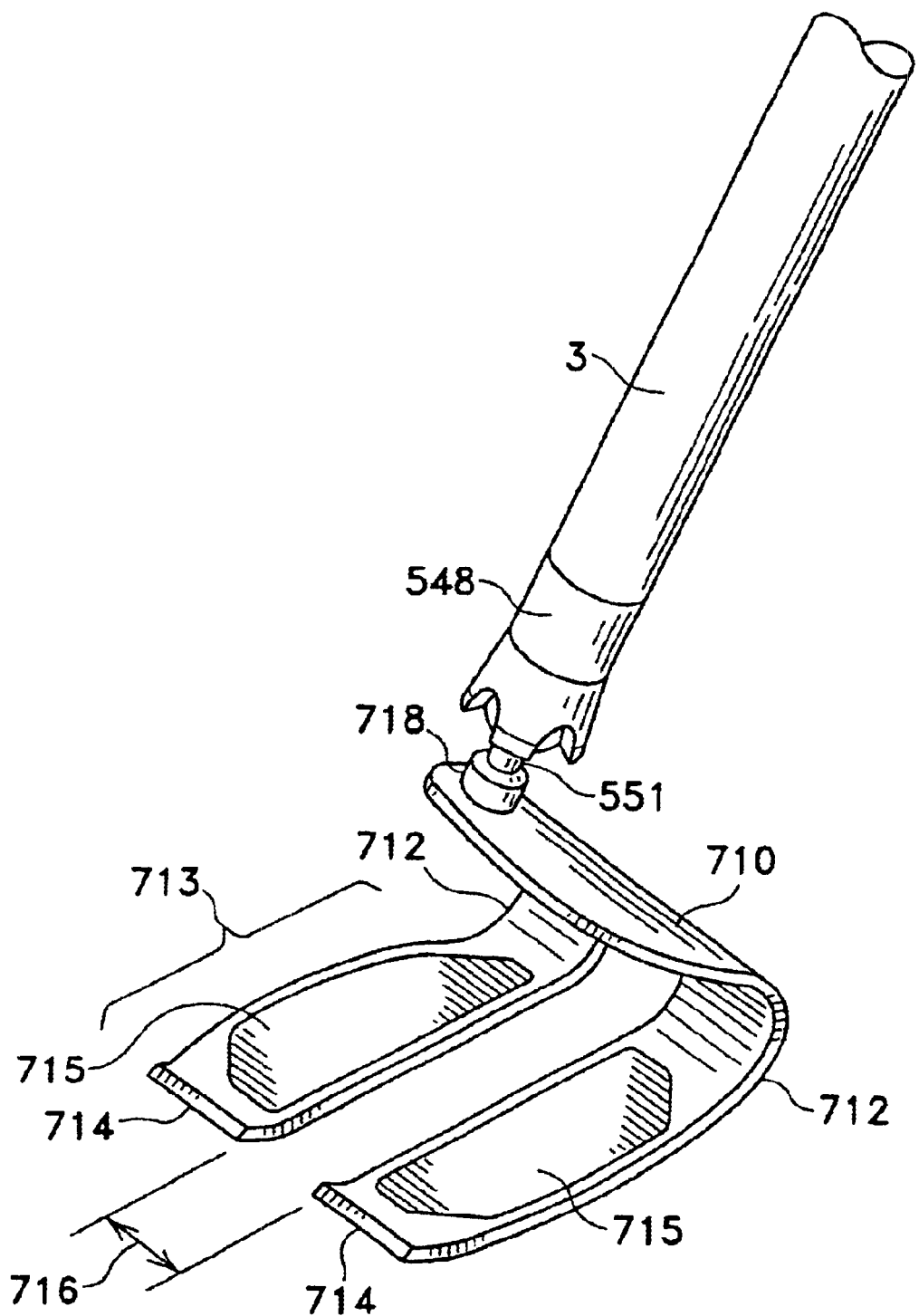
FIG. 43 is a perspective view illustrating a stabilizer base embodiment having an offset stem connection.

One useful variation, as illustrated in FIG. 43, connects connecting delivery stem 3 to the base portion of the stabilizer at a position which is generally offset from the center or off center. Base portion 710 is again typically formed of a unitary piece of sheet material and has a curved back portion in which connecting delivery stem 3 is attached to an extension of the same surface which carries the contacting members, except that the connecting point 718, to which ball/post 551 is attached is positioned away from the center and therefore away from the space between contact members 712 where the anastomosis would be performed. This configuration tends to ensure that connecting delivery stem 3 will not interfere with the surgical access to the center area of the base portion. Of course; the connection to can be offset from the central region in either direction.

In addition, base portion 710 illustrates a number of features for improving the traction and vessel presentation during a CABG procedure on a beating heart. Contact members 712 of base member 710 have portions 713 having an increased width and which are preferably substantially flat or slightly curved to conform to the heart. This configuration provides a larger area for coined regions 715, which represent indentations on the bottom surface for receiving a traction material, thus providing greater traction against the surface of the heart.

Further, base portion 710 provides a smaller open space between contact members 712. In a preferred embodiment, the spacing 716 between contact members 712 is less than about 0.350 inches, more preferably less than about 0.300 inches, and most preferably about 0.25 inches. This minimized spacing provides stabilization closer to the vessel and, in some instances, the compressive forces applied through contact members 712 actually tend to present the vessel upwards between contact members 712 in a more favorably pronounced manner. The tip portions 714 of contact members 712 are angled upwards from the surface of the heart to minimize any possible trauma to the heart during use.

As just discussed, the base portions (550 or 710) can be manipulated or oriented relative to the end of the connecting delivery stem 3 by virtue of the ball and socket joint between base portion 553 and connecting delivery stem 3. The amount of angular manipulation or travel available is somewhat limited as ball/post 551 eventually bottoms out or stops against either the bottom of slots 549 or extended tips 550. Thus, the contact members have a limited range of movement relative to connecting delivery stem 3 based upon the nominal to mounting relationship between the contact members and the ball/post. Accordingly, for some procedures, it may be desirable to have a different nominal relationship between the contact members and the ball/post to deliver stem connection.

Figure 44:
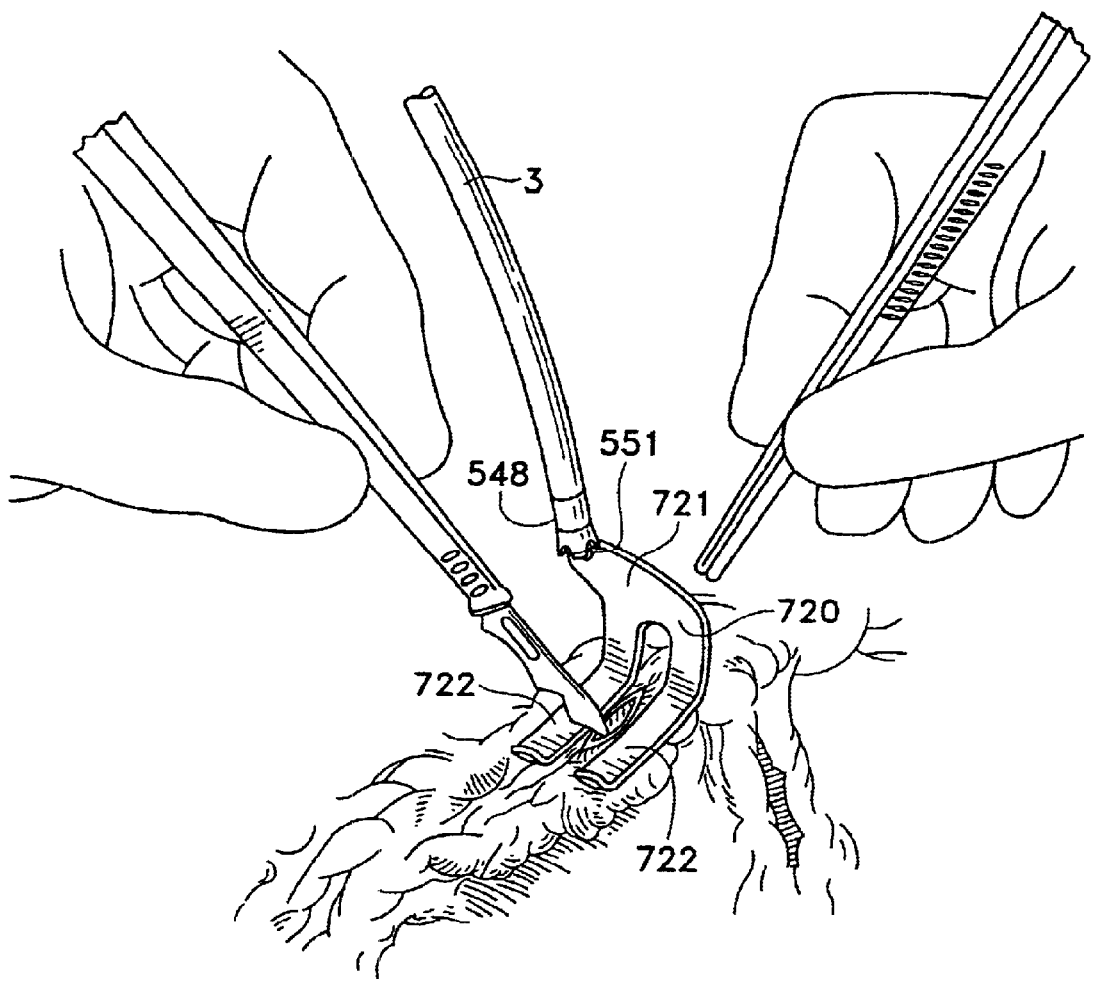
FIG. 44 is a perspective view illustrating an alternative offset stabilizer base in use over a target vessel.
Figure 45:
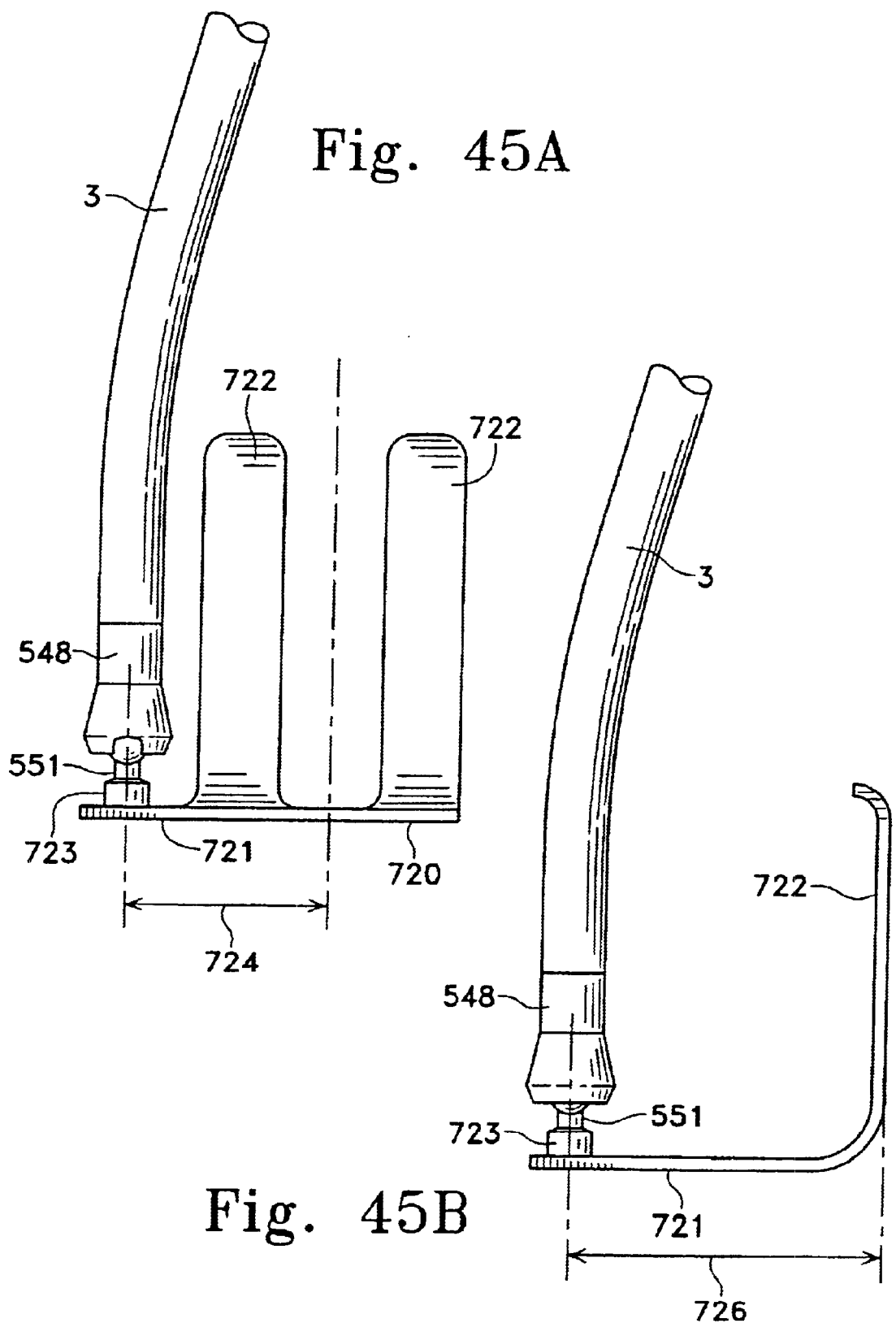
FIGS. 45A and 45B are respectively front and side plan views of the off set stabilizer base embodiment of FIG. 44.

Referring to FIGS. 44–45B, base member 720 illustrates an alternative orientation of ball/post 551. Instead of being angled away from the contact members, base member 720 has a back portion 721 which allows ball/socket 551 to be mounted generally parallel to contact members 722. Ball/post 551 preferably extend towards contact members 722 as shown, but may also extend the opposite direction away from the contact members. The connecting point 723 is preferably offset a distance 724 from the central area between the contact members 722. The connecting point 723 is also off set a greater distance 726 from the contacting place of contact members 722. In nominal position of base portion 722 relative to ball/post 551, this configuration tends to keep the connecting delivery stem 3 clear from the central portion between contact members 722. Furthermore, relative to connecting delivery stem 3, contact members 722 can be maneuvered through a range of motion different from base member 553 due to the initial orientation of ball/post 551.

Figure 46:
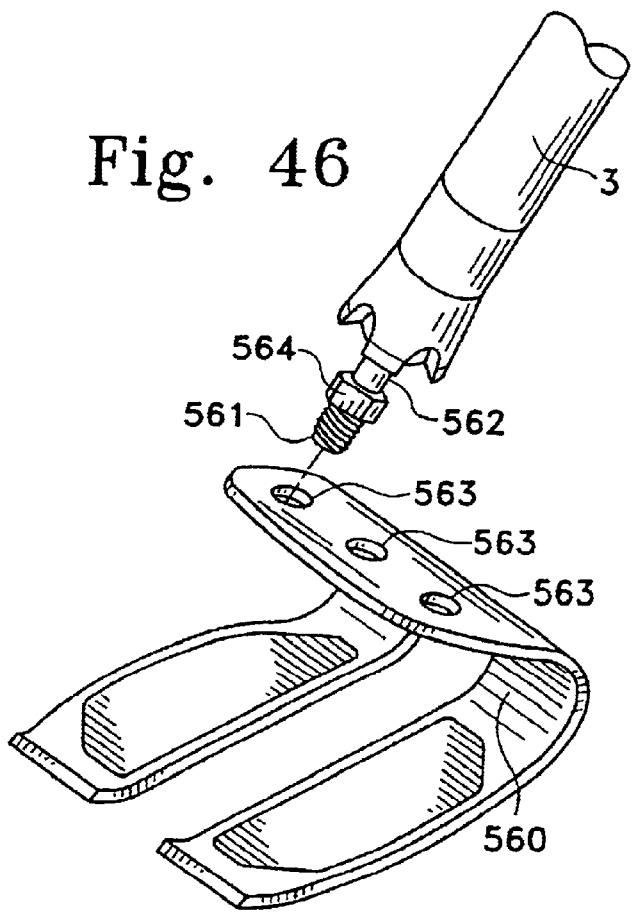
FIG. 46 is a perspective view of a tissue stabilizer having a moveable ball/post.

Because the preferred location of the attachment of the connecting delivery stem 3 to the base portion may be different from surgeon to surgeon and from procedure to procedure, it may be desirable to have the ball/post moveable to more than one location. In one embodiment shown in FIG. 46, for example, ball/post 562 has threaded end 561 which may be threaded into any desired threaded receiving hole 563 provided in stabilizer base 560. Ball post 564 is preferably provided with one or more flats 564 on the exterior thereof to facilitate tightening or loosening of the threaded connection. In the embodiment shown, stabilizer base 560 has threaded receiving holes 563 to provide center, offset right, and offset left connecting positions.

Figure 47:
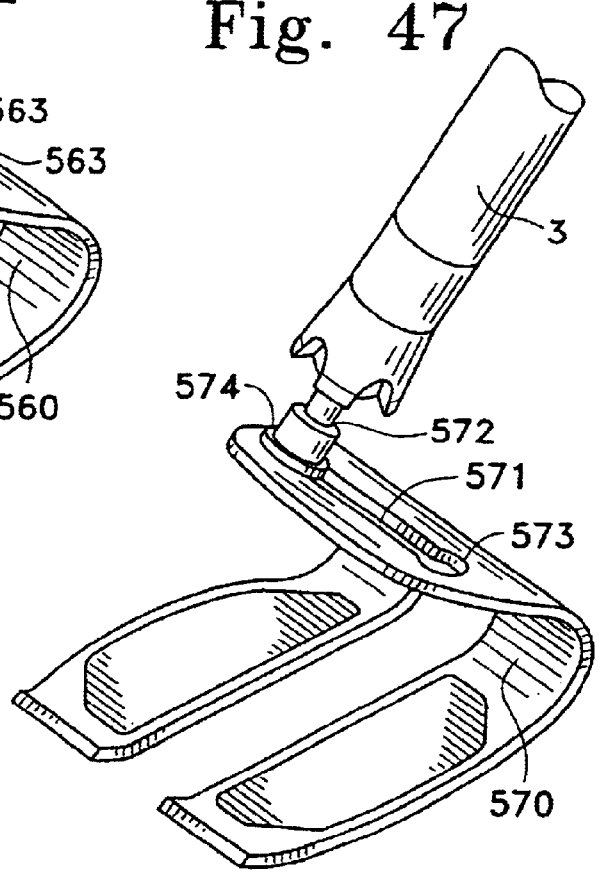
FIG. 47 is a perspective view illustrating another tissue stabilizer embodiment 5 having a moveable ball/post.
Figure 48:
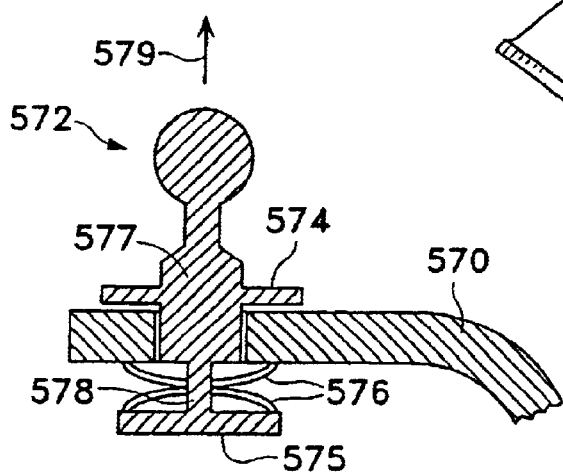
FIG. 48 is a partial cross-section taken through the ball/post of FIG. 47 showing a spring biased ball/post.

Referring to FIGS. 47 and 48, ball/post 572 may be captured within slot 571 formed in stabilizer base 570. Slot 571 preferably has two or more positions where the ball/post can be positively locked. In a preferred embodiment, slot 571 preferably has two or more key-hole openings 573. Key openings 573 are sized to receive first post portion 577 having an outside diameter which closely matches the inside dimension of key opening 573. First post portion 577 of ball/post 572 is released from key hole 573 by pulling ball post in the direction indicated by arrow 579 until second post portion 578 is positioned within keyhole 573. Second post portion 578 is sized to have an outside diameter small enough to fit arid traverse through slot 571. Ball/post 572 may then be traversed along the path defined by slot 571 until the next desired key hole is reached, which may then be engaged by first post portion 577 to secure ball/post 572 in position on stabilizer base 570.

Figure 49:
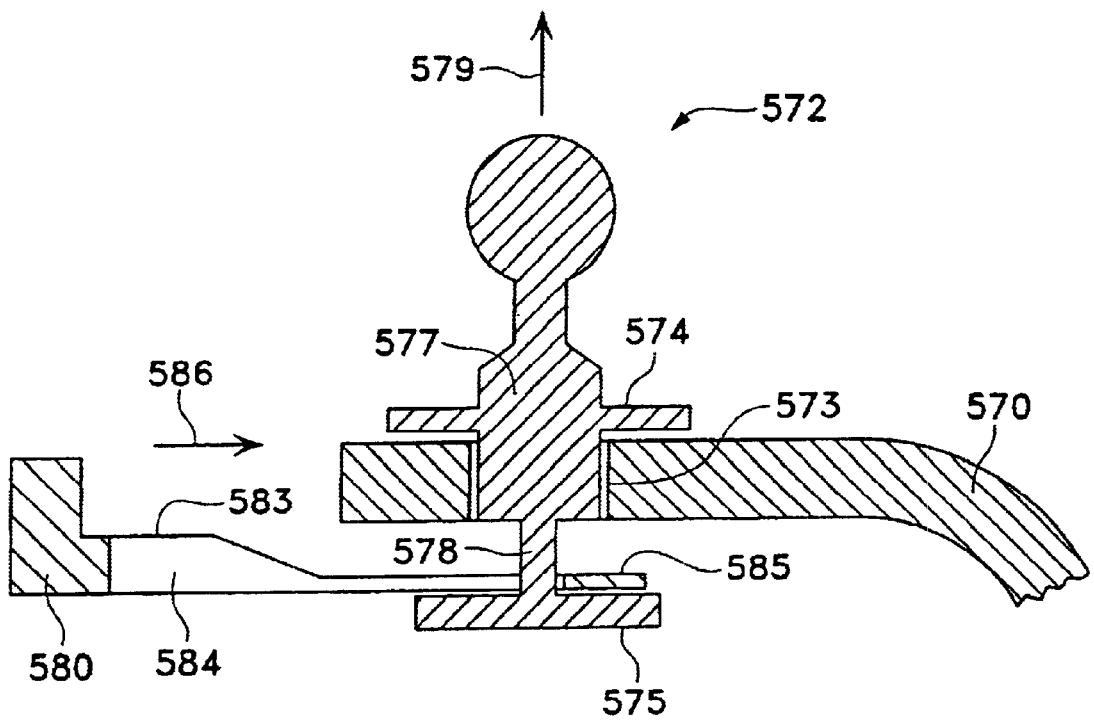
FIG. 49 is a partial cross-section showing the ball/post of FIG. 48 utilizing a locking clip to secure the ball/post.
Figure 50:
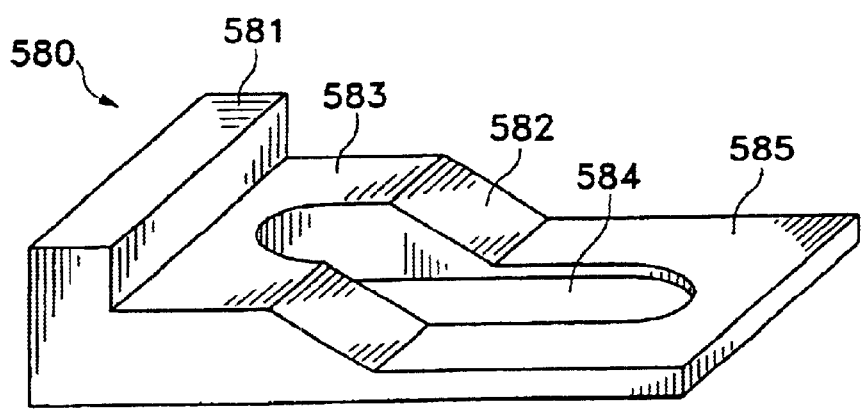
FIG. 50 is a perspective view of the locking clip of FIG. 49.

First post portion 577 may be kept in engagement with keyholes 573 by any, convenient manner. For example, ball/post 572 may be spring biased in the locked position between upper flange 574 and lower flange 575, preferably using spring washers 576 as shown. Ball/post 572 may also be locked into operating position within keyholes 573 by using a retaining or locking clip, such as locking clip 580 illustrated with reference to FIGS. 49 and 50. Locking clip 580 has slot 584 adapted to slide over second post portion 578. Locking clip 580 includes a thin portion 585, a thick portion 583, a transition ramp 582 between thin portion 585 and thick portion 583, and a grip or handle portion 581. With locking clip 580 in the open position shown in FIG. 44, ball to post 572 is free to move upwards in the direction of arrow 579, thus releasing first post portion 577 from key hole 573. When locking clip 580 is moved in the direction indicated by arrow 586, the outer thickness of thick portion 583 is wedged between lower flange 575 and stabilizer base 570, thus locking ball/post 572 in place within keyhole 573.

Figure 51:
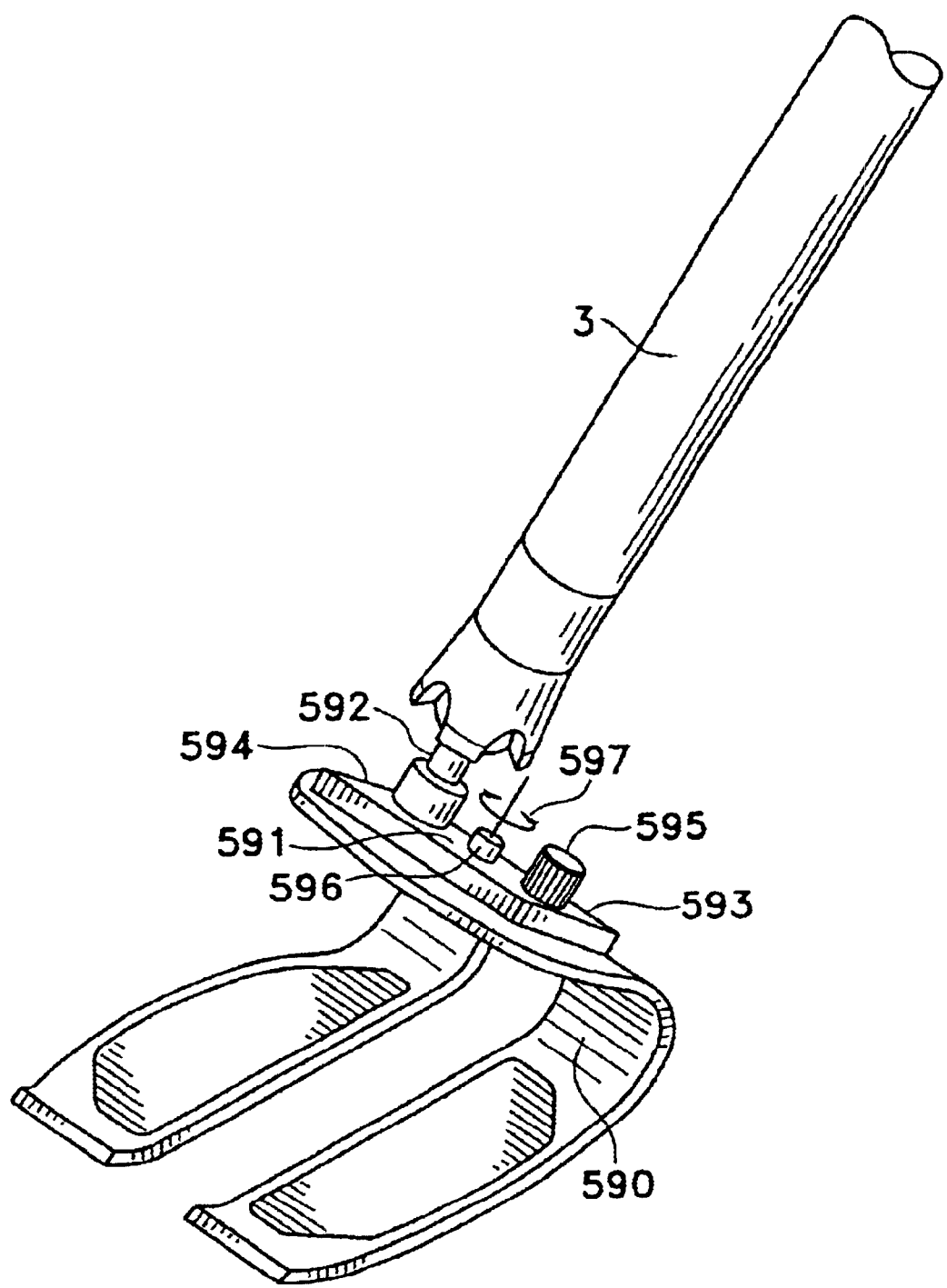
FIG. 51 is a perspective view illustrating another moveable ball/post stabilizer embodiment.

Stabilizer base 590 in FIG. 51 has ball/post 592 mounted to an articulating member which is moveable between two or more positions. Preferably, ball/post 592 is mounted on first end 594 of pivoting link 591 which is pivotably attached to stabilizer base 590 at pivot pin 596. Preferably, pivot pin 596 is centrally located on pivoting link 591. At second end 593 of pivoting link 591, a locking knob 595 may be provided to engage stabilizer base 590. Preferably, locking knob 595 has a threaded shaft or other such fastening or locking feature which engages mating threaded holes (typically one positioned under locking knob 595 and one under ball/post 592) in stabilizer base 590. The ball/post 592 and locking knob 595 are preferably spaced equal distances from pivot pin 596 such that when pivoting link 591 is rotated as indicated by, arrow 597, the position of ball/post 592 and locking knob 595 are reversed.

Another embodiment of a tissue stabilizer having an adjustable attachment position of the delivery stem is illustrated in FIGS. 52–55. Stabilizer base assembly 625 includes top member 605 and stabilizer base 600, having contact members 606 and 607 and notch or relief 603 under which a vessel may safely pass without being occluded. At least a portion of stabilizer base 600 has outer profile 601 which is generally curved or circular at a predetermined radius. Top member 605 has a mating interior curvature such that stabilizer base 600 and top member 605 concentrically rotate relative to each other, preferably about a common center point. Ball/post 602 may be attached at a convenient position, typically centered, on top member 605. Rotation of top member 605 relative to stabilizer base 600, as indicated by arrows 620 and 619, thus adjusts the position of ball/post 602 along an arcuate path relative to contact members 606 and 607.

To facilitate the secure attachment and smooth rotation of top member 605 relative to stabilizer base 600, top member 605 may be provided with one or more projections adapted to be received within guide slots provided in stabilizer base 600. In a preferred embodiment, top member 605 has side projections or rails 608 and 609 which snap into lower slots or channels 611 and 610 in stabilizer base 600 as top member 605 is urged into a concentric position over stabilizer base 600. Rails 608 and 609 slide within channel 611 and 610 to maintain a secure attachment and controlled rotation of top member 605 and stabilizer base 600. Top member 605 may optionally have tab 612 adapted to be received within upper slot 604 on stabilizer base 600. Upper slot 604 may have a plurality of detents or teeth which form a desired number of detented positions as tab 612 is rotated around the path of upper slot 604. In a preferred embodiment, detented position 617 is formed between tooth 613 and slot end 616 and detented position 618 is formed between tooth 614 and tooth 615. Of course, detented positions may be created at any desired location using a variety of alternate constructions. Preferably, the detent action of tab 612 allows the operator to manually select a position of ball/post 602, but then holds the position of top member 605 relative to stabilizer base 600 against movement during use to ensure effective stabilization of a target vessel on the beating heart.

In addition to the critical function of stabilizing the beating heart, it is also important for the tissue stabilizer to present the stabilized coronary artery in a manner which allows sutures to be easily placed around the mouth of the arteriotomy as required to create the anastomosis. FIGS. 56A–59 illustrate a tissue stabilizer embodiment involving a base portion having a single contacting surface for stabilizing a target vessel on the beating heart and a mechanical bail element to facilitate optimal vessel presentation.

Figure 56A:
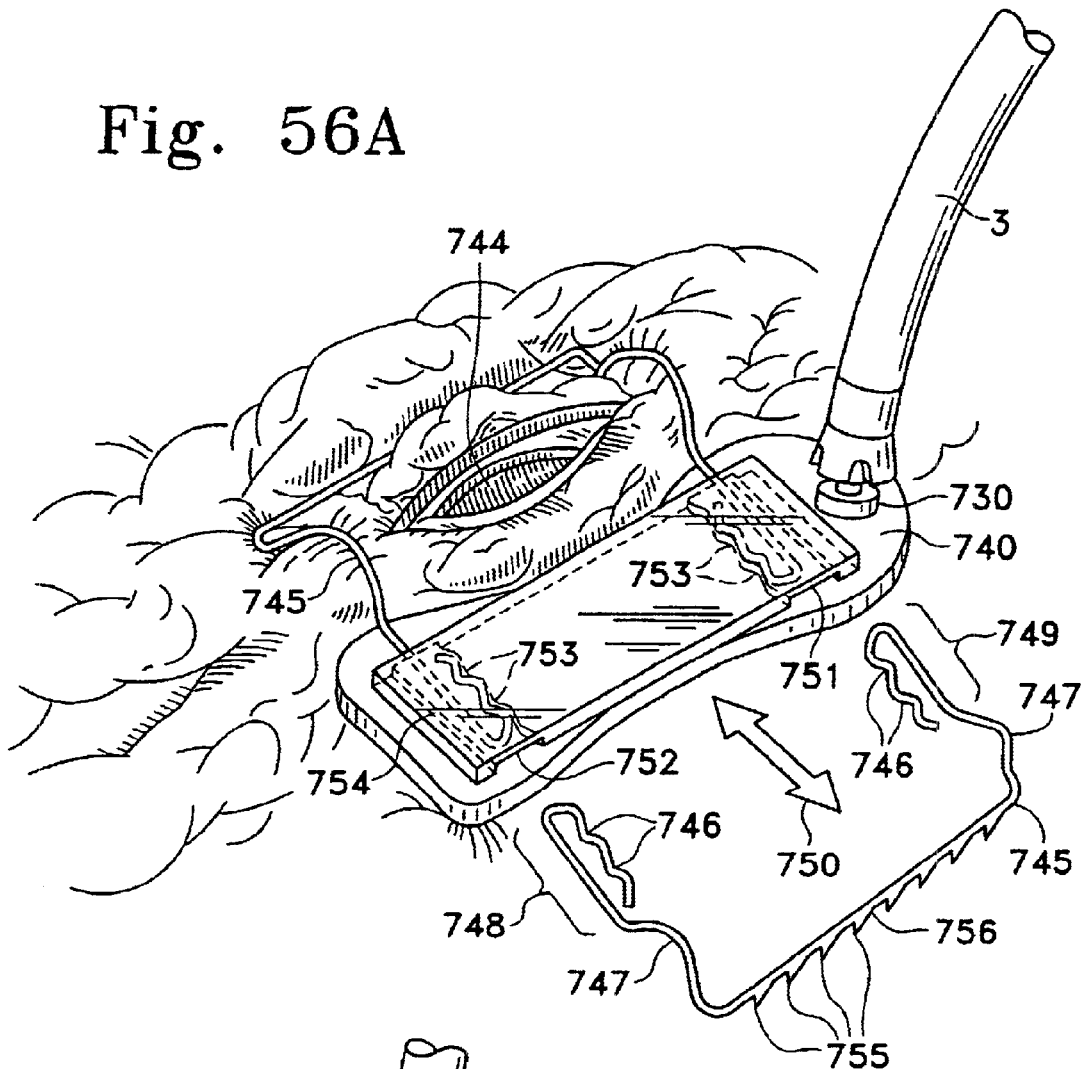
FIG. 56A is a perspective view of a stabilizer base embodiment having a single contact member and bail construction.
Figure 56B:
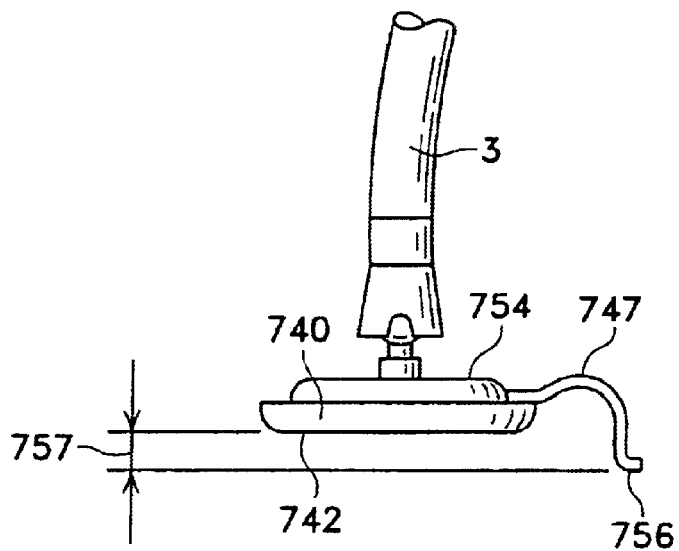
FIG. 56B is an end plan view of the stabilizer embodiment of FIG. 56A.

Referring to FIGS. 56A and 56B stabilizer base 740 is shown attached to delivery stem 3 using ball/post 730. Delivery stem 3 is shown connected generally to the center of stabilizer base 740 at approximately a right angle, however, as discussed above, the ball/post 730 could be connected at any desired offset or orientation or the position of ball/post 730 could be adjustable. Stabilizer base 740 preferably has a single contacting surface 742 which may be flat or curved to at least partially conform to the surface of the heart. Contacting surface 742 is sized to provide sufficient contacting area such that sufficient compressive force can be applied to the beating heart to achieve effective immobilization or stabilization of a target coronary artery.

Stablizer base 740 preferably has an extending frame member or bail 745 attached thereto. Bail 745 may be a thin, round or square cross-sectioned member, and is preferably a stainless steel wire. Bail 740 has a bail portion 756 which is generally parallel to stabilizer base 740 and may have relieved sections 747 formed therein so as not to occlude the vessel during use. Bail portion 756 may have tissue gripping features, such as teeth 755. In an optional embodiment, bail portion 756 may be provided with rotating cover or a spiral wound thread (not shown) so that bail portion may be more easily repositioned, under a stabilizing load, over the surface of the heart as discussed below.

In a preferred embodiment, bail 745 is moveable relative to stabilizer base 740. Bail 745 can, be moved in or out in the direction indicated by arrow 750 to cause bail section 756, which is generally parallel with stabilizer base 740, to compress tissue towards stabilizer base 740 or stretch tissue away from stabilizer base 740. Thus, bail 745 can be moved in and out to compress or stretch the tissue surrounding a coronary artery until the optimum presentation for performing the anastomosis is achieved. The generally parallel portion may be vertically offset from contacting surface 742 by a distance 757 which is typically about 0.050 inches to about 0.200 inches.

Although bail 745 may be attached in a number of ways, bail 745 is preferably formed with first and second end portions 748 and 749 having detents or teeth 746. Stabilizer base 740 preferably has channels 751 and 752 for receiving end portions 749 and 748 respectively. Channels 751 and 752 preferably have internal mating teeth 753 for engaging teeth 746. End portions 748 and 749 can be incrementally advanced into channels 752 and 751 as teeth 746 deflect and release from a mated position relative to teeth 753 and then successively engage the next mated position. Stabilizer base 740 may include cover 754 over channels 751 and 752. So that the stabilizer can be removed from around a completed anastomosis, at least one end of bail 745 is detachable from stabilizer base 740. In a preferred embodiment, stabilizer base 740 is substantially symmetrical allowing bail 745 to be assembled from either side in a right or left handed configuration.

Bail 745 is preferably flexible or semi-flexible relative to stabilizer base 740. As a result of its inherent flexibility, bail 745 applies a predetermined force against the heart that, under operating conditions, may be generally independent of the stabilizing force applied to stabilizer base 740 to stabilize the beating-heart. That is, once stabilizer base 740 is forced against the surface of the heart, the force applied by bail 745 is a function of its mechanical spring rate relative to stabilizer base 740.

Figure 57A:
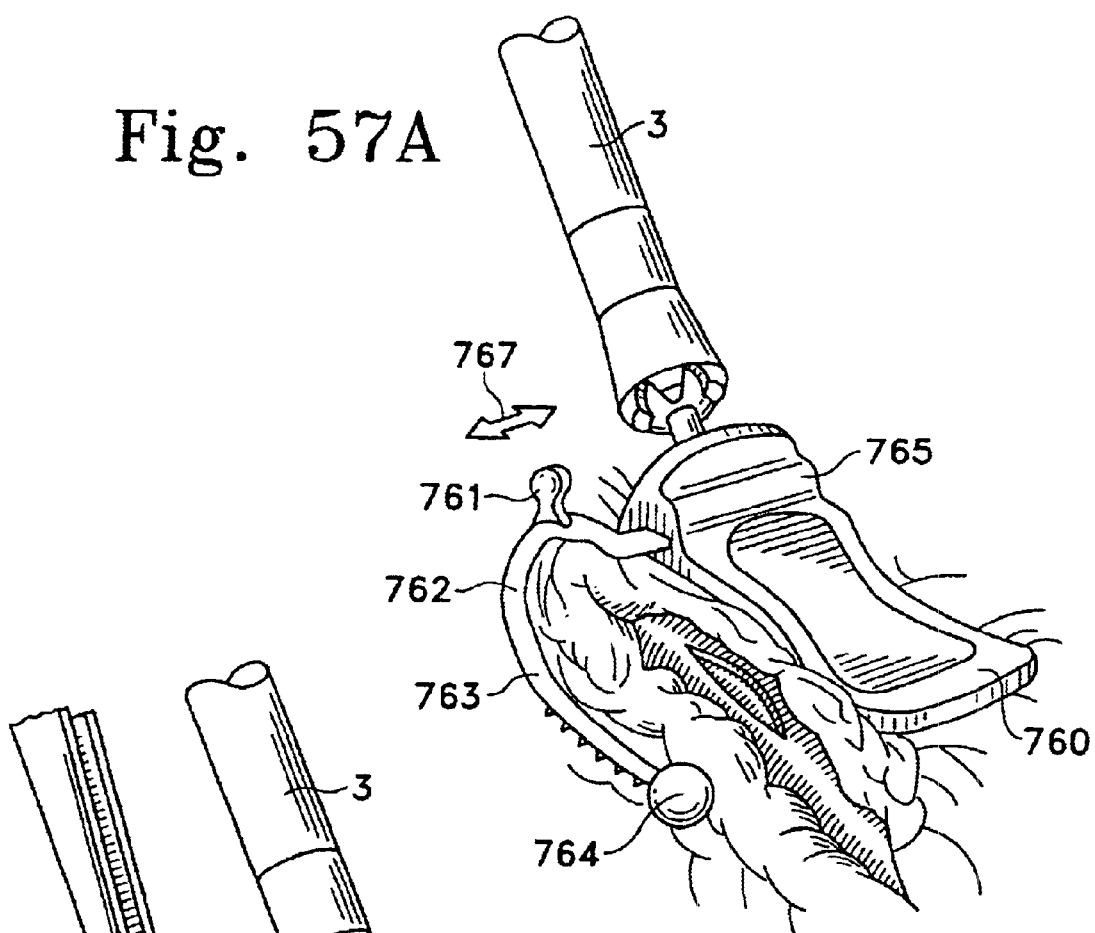
FIGS. 57A and 57B are perspective views illustrating another stabilizer base embodiment having a single contact member and bail construction.
Figure 57B:
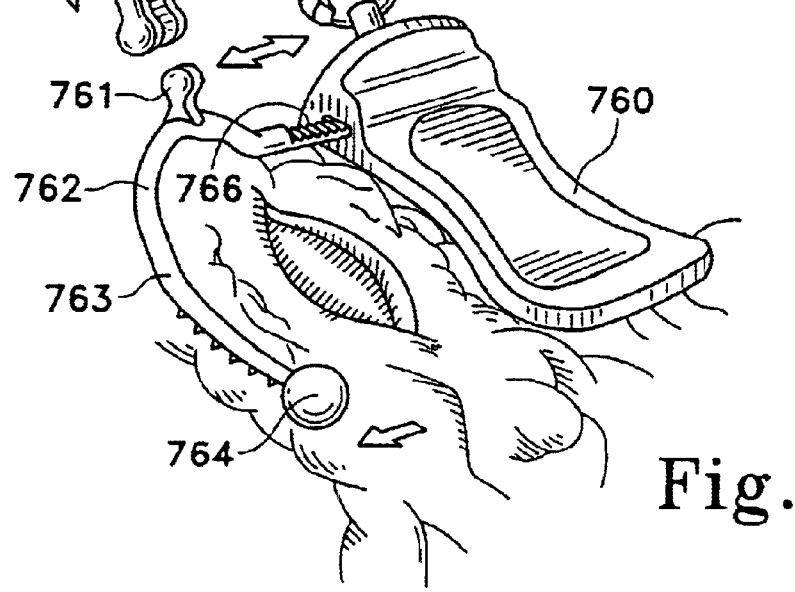

FIGS. 57A and 57B illustrate another single contact stabilizer base having a bail 762 which is secured at only one end. Stabilizer base 760 may have a housing 765 having a series of internal teeth (not shown). Bail 762 has a toothed end 766 which is received within housing 765 to engage with the mating teeth provided therein. As with the embodiment above, bail 762 has a generally parallel portion 763 which is moveable relative to stabilizer base 760 in the direction generally indicated by arrow 767 to stretch or compress the surrounding tissue for optimum vessel presentation. Bail 762 may have tab 761 to facilitate grasping by an instrument, such as for example forceps 761. The free end 764 of bail 762 is preferably rounded or somewhat bulbous so as to be a traumatic. Because bail 762 attaches only at one end, the stabilizer can be easily removed from the completed anastomosis without removing bail 762 from stabilizer base 760.

Figure 58:
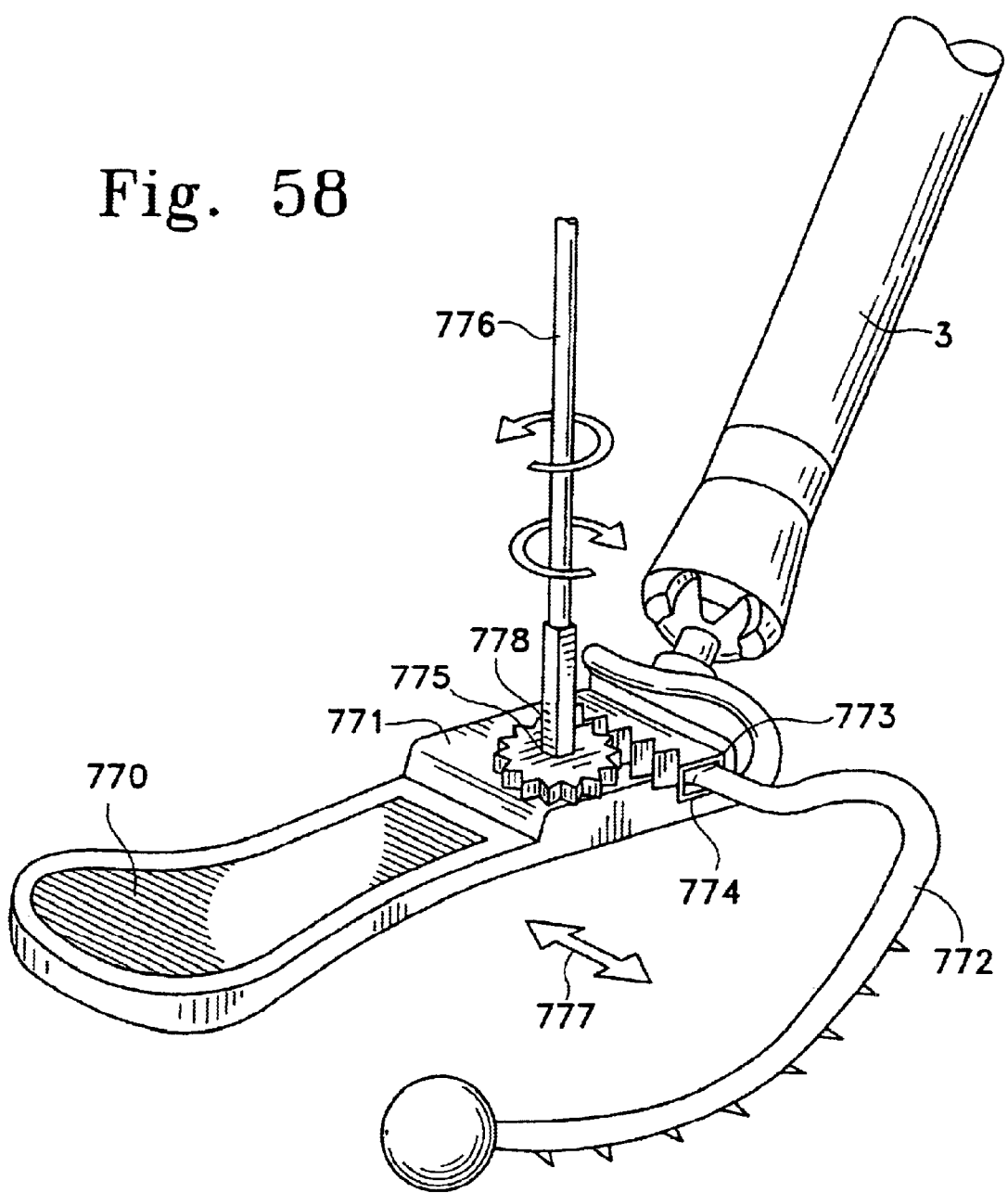
FIGS. 58 and 59 are perspective views illustrating stabilizer base embodiments having a single contact member and a bail having a mechanical drive.

In another embodiment of the stabilizer, the wire frame member or bail may have a drive mechanism for moving the bail relative to the stabilizer base. Referring to FIG. 58 stabilizer base 770 has housing 771 which is constructed with guide channel 774 having gear 775 mounted for rotation therein. Bail 772 has a toothed end 773 which may be assembled within guide channel 774 such that rotation of gear 775 causes bail 772 to be moved in and out in the direction indicated by arrow 43. Gear 775 may be driven by any suitable tool, for example, gear 775 may have a drive hole 778 for engagement by a suitable drive tool 771.

Figure 59:
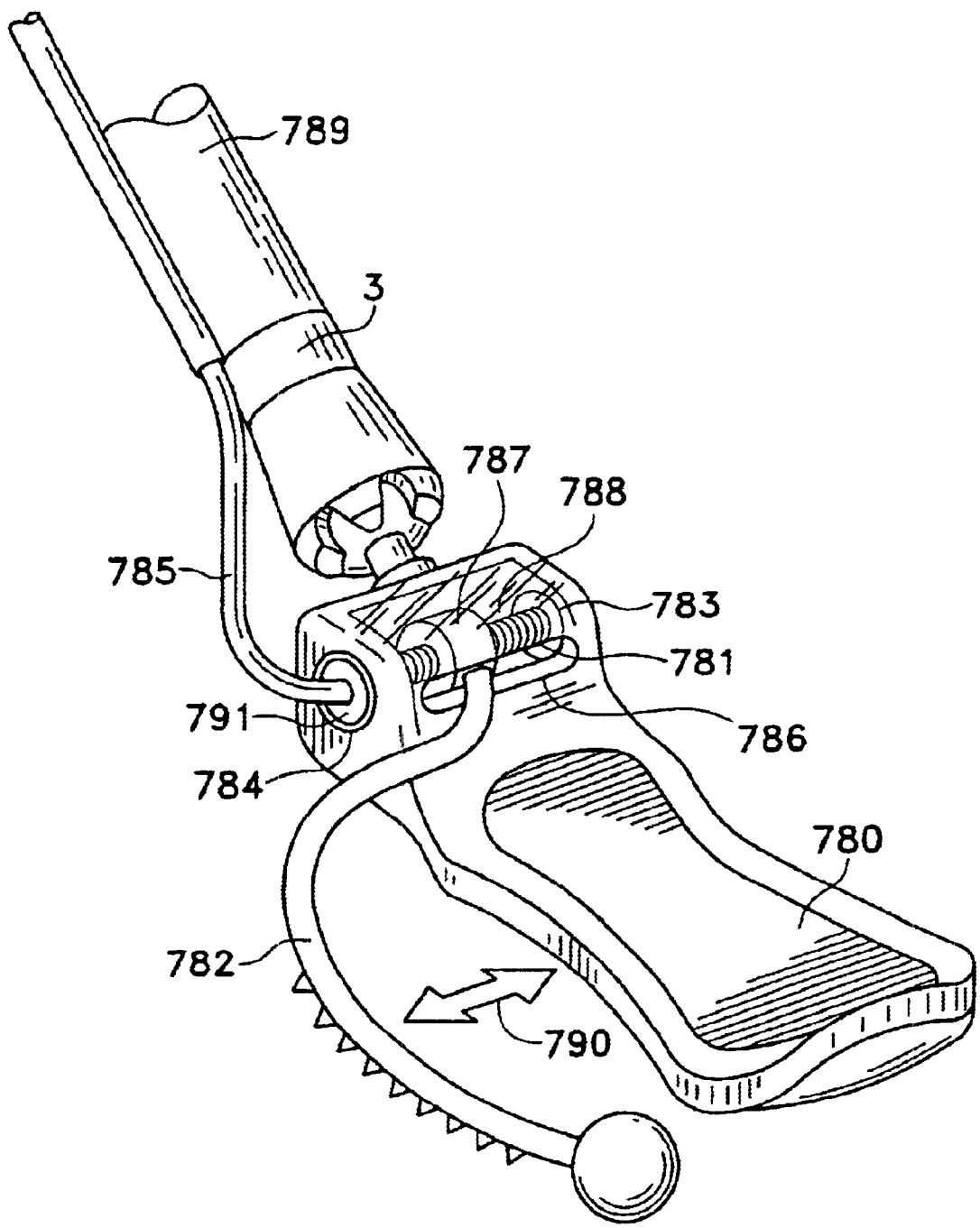

Another driven bail stabilizer is shown in FIG. 59. In this embodiment, stabilizer base 780 has threaded shaft 781 preferably supported at its end portions by bushings or bearings 783 and 784. One end of the threaded shaft is connected to a flexible drive 785 through a flexible or universal joint 791. The flexible drive maybe routed up delivery stem 3. Preferably flexible drive 785 is secured to delivery stem 3 by way of a thin polymeric coating. Bail 782 is connected to threaded collar 787 which cooperates with threaded shaft 781 to move bail in and out relative to stabilizer base 780 in the general direction indicated by arrow 790. The screw and collar drive mechanism is preferably concealed by housing 788 which has only a small slotted opening 786 allowing passage of bail 782.

With each of the flexible bail embodiments described above, stabilization and vessel presentation are relatively independent. First, the beating heart is typically stabilized using a compressive force delivered by way of the single contacting surface provided by the stabilizer base. The bail may then be manipulated in or out to obtain the optimum presentation of the vessel for whatever surgical-procedure is underway. For example, one bail position may be optimal for creating the arteriotomy, another bail position for insertion of a shunt or like device (should one be used), another bail position for creating the anastomosis, and so on. All the while, the stabilization of the beating heart itself remains optimized by the contacting surface of the stabilizer base.

The Stabilization System

Figure 60:
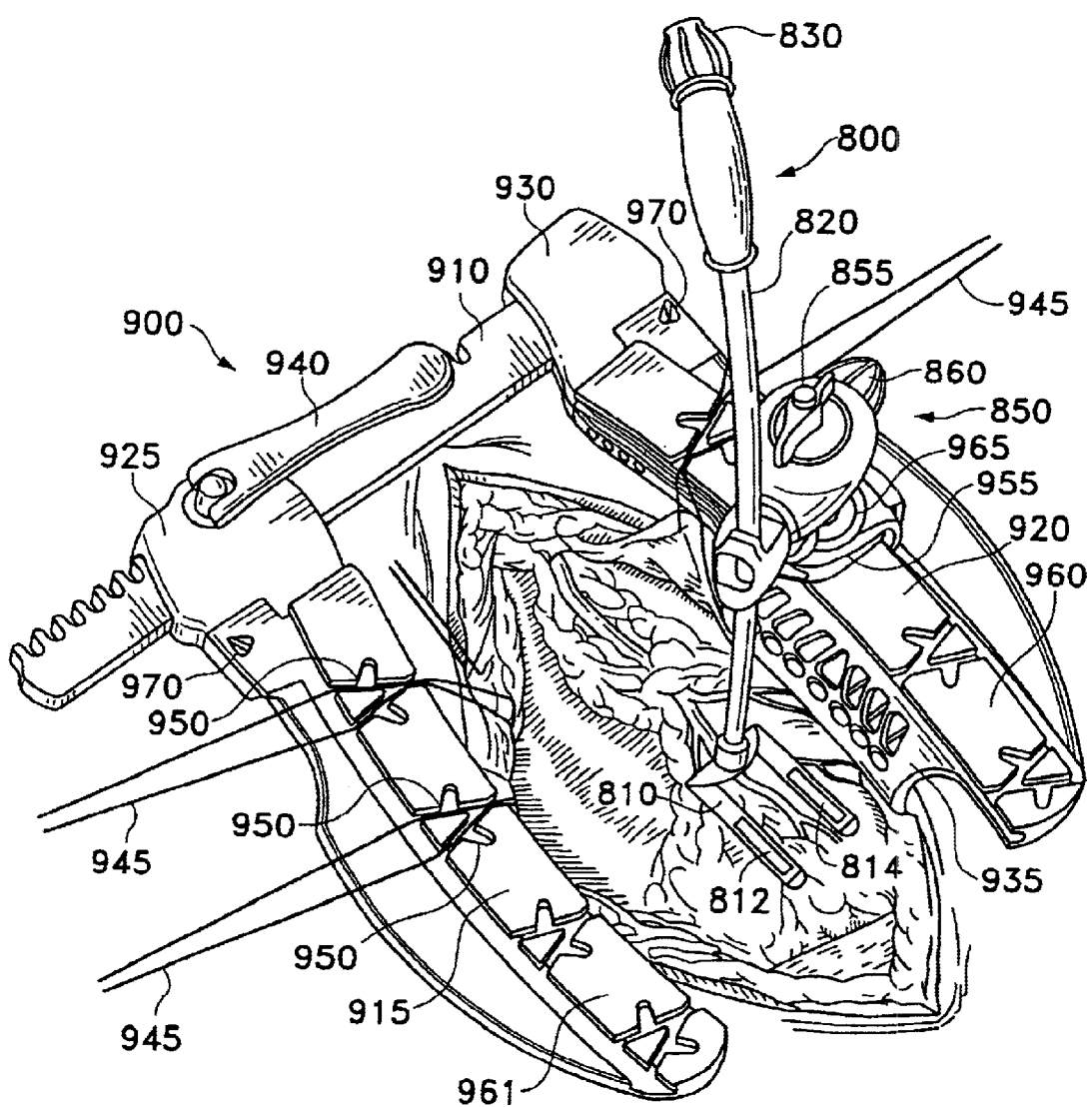
FIG. 60 is a perspective view of a preferred cardiac surgery system during operation according to the principles of the present invention.

Preferred embodiments for each of the retractor, the instrument mount and the tissue stabilizers have been discussed in detail above. While each component may be utilized separately, superior access and stabilization can be achieved when the multiple components are used together for performing a minimally invasive cardiac surgery, preferably through a sternotomy approach. Referring to FIG. 60, retractor assembly 900, including drive mechanism 910 and first and second platform blades 915 and 920, may be used to spread the sternum, providing access and direct visualization to the thoracic cavity. Retractor assembly 900 also allows sutures to be fixed or organized. Stabilizer assembly 800 isolates and provides local immobilization of the target vessel on the beating heart. Instrument mount assembly 850 facilitates precise maneuvering of the stabilizer and ensures a stable, motion free mount at the desired position and orientation.

To begin a typical beating heart CABG procedure using the preferred stabilization system illustrated in FIG. 60, drive mechanism 910 is preferably placed in the fully closed position with moveable housing 925 positioned against or adjacent fixed housing 930. First platform blade 915 is then assembled to moveable housing 925 and a second platform blade 920 is assembled to fixed housing 930. After ensuring that platform blades 915 and 920 are fully and securely attached to drive mechanism 910, engaging members 935 of platform blades 915 and 920 are securely seated on the incised sternum created using standard surgical procedures. Drive handle 940 may then be rotated clockwise to separate platform blades 915 and 920, thus creating the desired opening for accessing the beating heart.

If the heart is positioned using sutures, the sutures may be placed through the tissue at the desired location and secured to platform blades 915 and 920. Sutures 945 may be slid into suture holder slots 950 to engage the suture. To ensure proper a proper hold, only one suture strand is preferably engaged within each suture holder slot 950. Sutures 945 are released from platform blades 915 and 920 by concurrently pulling back and up on suture 945 while pulling the suture through the suture holder slot 950.

With the heart positioned as desired, instrument mount assembly 850 may be assembled to platform blade 920 (or 915) by hooking stabilizer mount base 955 onto rail 960 (or 961) at the desired location and moving the base lever (not visible in this view) clockwise to the closed position to secure instrument mount assembly 850 onto rail 960. Mount body 110 may be oriented to the desired angle by way of ball joint 965 and locked into place by turning the top mount knob 855 clockwise.

Stabilizer base 810, having contact members 812 and 814, may then be positioned on the epicardium of the beating heart by gently lowering delivery stem 820 using one hand to guide stabilizer base 810 onto the target area on the heart. Incremental pressure is applied to stabilizer base 810 situated on the epicardium until the desired immobilization, or stabilization is achieved. Delivery stem 820 is secured in the desired position by turning side mount knob 860 clockwise and stabilizer base 810 is secured in the desired position relative to delivery stem 820 by turning the stabilizer stem knob 830 clockwise. With the beating heart stabilized, the anastomosis, or other desired procedure, is completed.

To remove stabilizer base 810, delivery stem 820 is held with one hand while side mount knob 860 is loosened with the other hand. Stabilizer base 810 is then carefully removed from the anastomotic site. The base lever is moved to the open position to release instrument mount assembly 850, and stabilizer assembly 800 mounted thereto, from rail 960 on platform blade 920. When the entire bypass procedure is completed, drive handle 940 is rotated in the counter clockwise direction to close drive mechanism 910 and platform blades 915 and 920. Retractor assembly 900 may then be gently removed from the access incision. To remove platform blades 915 and 920 from moveable housing 925 and fixed housing 930, respectively, release latches 970 are manually activated and platform blades 915 and 920 may be pulled generally straight away from Drive mechanism 910. Drive mechanism 910 may then be sterilized and prepared for use in a subsequent procedure.

While certain embodiments are illustrated in the drawings and have just been described herein, it will be apparent to those skilled in the art that many modifications can be made to the embodiments without departing from the inventive concepts described. For purposes of illustration only, the principles of the present invention has been generally described with reference to a coronary artery bypass procedure, but may readily be applied to other types surgical procedures not specifically described. Many other uses are well-known in the art, and the concepts described herein are equally applicable to those other uses. Further, the different components of the various exemplar embodiments described above can be combined in any desirable construction. Accordingly, the invention is not to be restricted except by the claims which follow.

What is claimed is:

1. An instrument mount apparatus for positioning a surgical instrument comprising a mount body having a base portion moveably coupled at a first articulating joint and a side portion moveably coupled at a second articulating joint, and at least one actuator operatively connected to said first and second articulating joints, said'side portion configured for receiving said surgical instrument, said first and second articulating joints being freely moveable when said at least one actuator is in an unlocked position, wherein said first and second articulating joints are compressed each into a substantially immovable condition when said at least one actuator is placed in a locked position, and wherein said first articulating joint is at an angle relative to said second articulating joint.

2. The instrument mount apparatus of claim 1 wherein said angle is less than about 120 degrees.

3. The instrument mount apparatus of claim 2 wherein said angle is between about 100 degrees and about 45 degrees.

4. The instrument mount apparatus of claim 2 wherein said angle is about 90 degrees.

5. The instrument mount apparatus of claim 1, wherein said at least one actuator consists of a single actuator, said actuator comprising a base post assembled thorough said base portion and said mount body and interconnected at a first end to a cam operatively interfacing a contact surface on said mount body, and a tie pin having a slotted portion which receives said base post, wherein, upon operation of said cam, said base post is drawn toward said cam and said locked position and a ramped portion of said base post drives said tie pin towards said locked position.

6. The instrument mount apparatus of claim 5, wherein said first articulating joint comprises a ball and socket joint and said base post further comprises a flange at a second end opposite said first end, wherein movement of said cam to said locked position draws said flange against said base portion thereby locking said ball and socket joint.

7. The instrument mount apparatus of claim 5, wherein said second articulating joint comprises a rotational joint including a frustoconical member extending from said side portion and a cooperating frustoconical,cavity within said mount body.

8. The instrument mount apparatus of claim 7, further including a grip member, said side portion and said grip member positioned to form an opening therebetween for receiving a surgical instrument.

9. The instrument mount apparatus of claim 8, wherein said tie pin is connected, at a first end, to said grip member.

10. The instrument mount apparatus of claim 9, wherein said tie pin comprises a pair of flexible prongs which interconnect at said first end with said grip member.

11. The instrument mount apparatus of claim 10, wherein movement of said tie pin to said locked position draws and locks said grip member against said side portion and also locks said frustoconical member against said frustoconical cavity thereby locking said rotational joint.

12. The instrument mount apparatus of claim 9, wherein said tie pin is releasably connected to a release button at a second end of said tie pin, wherein pressing of said release button extends said tie pin and grip member to allow removal of said grip member to exchange surgical instruments.

13. The instrument mount apparatus of claim 1, wherein said first articulating joint comprises a ball and socket joint.

14. The instrument mount apparatus of claim 13, wherein said ball and socket joint comprises a ball-shaped member extending from said base portion and a cooperating socket formed with said mount body.

15. The instrument mount apparatus of claim 1, wherein said second articulating joint comprises a ball and socket joint.

16. The instrument mount apparatus of claim 1, wherein said second articulating joint comprises a rotational joint.

17. The instrument mount apparatus of claim 16, wherein said rotational joint comprises a frustoconical member extending from said side portion and a cooperating frustoconical cavity within said mount body.

18. The instrument mount apparatus of claim 17, wherein said side portion further includes a grip member, said side portion and said grip member positioned to form an opening therebetween for receiving a surgical instrument.

19. The instrument mount apparatus of claim 18, wherein said base portion is adapted to cooperatively engage a rail member.

20. The instrument mount apparatus of claim 19, wherein said rail has a top portion and a bottom portion, said bottom portion having a narrowed region adjacent said top portion forming first and second tabs on said top portion and said base portion further comprising first and second hooks adapted to engage said first and second tabs.

21. The instrument mount apparatus of claim 19, wherein said rail is fixed to a sternal retractor.

22. The instrument mount apparatus of claim 19 wherein said rail is fixed to a rib retractor.

23. The instrument mount apparatus of claim 1, further comprising:
   a post extending through said first articulating joint along a first axis, said post having a first end portion engaging said base portion;
   a pin extending through said second articulating joint along a second axis, said pin having an end portion engaging said side portion and a threaded portion; and a knob having an internal bore for receiving said at least a portion of said pin, said internal bore having threads adapted to engage said threaded portion of said pin, said knob having a thrust-surface associated therewith adapted to engage and move said post as said knob traverses over said threaded portion of said pin.

24. The apparatus of claim 23, wherein said first axis is at an angle relative to said second axis.

25. The apparatus of claim 24, wherein said angle is less than about 120 degrees.

26. The apparatus of claim 25, wherein said angle is between about 100 degrees and about 50 degrees.

27. The apparatus of claim 26, wherein said angle is about 90 degrees.

28. The apparatus of claim 23, wherein said first articulating joint is a ball and socket joint.

29. The apparatus of claim 28, wherein said ball and socket joint comprises a ball-shaped member extending from said base portion and a cooperating socket formed within said mount body.

30. The apparatus of claim 23, wherein said second articulating joint is a ball and socket joint.

31. The apparatus of claim 23, wherein said second articulating joint is a rotational joint allowing rotation of said side member about said second axis.

32. The apparatus of claim 31, wherein said rotational joint comprises a frustoconical member extending from said side portion and a cooperating frustoconical cavity within said mount body.

33. The apparatus of claim 23, wherein said post further comprises a cam surface positioned to mate with said thrust surface, whereby rotation of said knob along said threaded portion causes translation of said thrust surface in a direction along said second axis, said thrust surface engaging said cam surface to move said post in a direction along said first axis.

34. The apparatus of claim 33, wherein said first articulating joint becomes locked when said post is urged in a first direction along said first axis and returns to a condition which allows articulation when said post is urged in an opposite direction to said first-direction along said first axis.

35. The apparatus of claim 23, wherein said knob comprises a first end adapted to be grasped by a user and a housing end adapted to be received within said mount body, said thrust surface being located on said housing end.

36. The apparatus of claim 23, further comprising a lift member slidable along said second axis, said lift member having a first end having said thrust surface and a second end, said knob having a first end adapted to be grasped by a user and a housing end adapted to be received with said mount body, said housing end positioned to engage said second end.

37. The apparatus of claim 23, wherein said mount body has a top opening and said post has a second end constrained within said top opening, said second end being slidable within said top opening along said first axis.

38. The instrument mount apparatus of claim 23, wherein said base portion is adapted to cooperatively engage a rail member associated with a retractor apparatus.

39. The instrument mount apparatus of claim 38, wherein said rail has a top portion and a bottom portion, said bottom portion having a narrowed region adjacent said top portion forming first and second tabs on said top portion and said base portion further comprising first and second hooks adapted to engage said first and second tabs.

40. An apparatus for stabilizing a localized portion of a beating heart, comprising:
    a substantially rigid base member having at least one surface adapted to contact the surface of the heart, a post having a first end moveably coupled to said base member and a second end having a ball-shaped member extending therefrom.

41. The apparatus of claim 40, wherein said at least one surface of said substantially rigid base member is adapted to frictionally engage the surface of the beating heart adjacent a first side of a target vessel; said apparatus further comprising:
    a wire frame coupled to said base member, said wire frame having a frame portion adapted to engage the beating heart adjacent a second side of the target vessel opposite to the first side and at least one leg portion, said leg portion connecting said frame portion to said base member.

42. The apparatus of claim 41, further comprising a delivery stem having a proximal end and a distal end, said base member being operably connected, via said ball-shaped member, to said distal end.

43. The apparatus of claim 42, wherein said delivery stem is substantially rigid.

44. The apparatus of claim 43, wherein said delivery stem is curved.

45. The apparatus of claim 41, wherein said leg portion is substantially perpendicular to said frame portion.

46. The apparatus of claim 41, wherein said wire frame is moveable relative to said base member.

47. The apparatus of claim 46, wherein said base member further comprises a channel for slidably receiving at least a portion of said leg portion.

48. The apparatus of claim 47, wherein said leg portion has a plurality of detented positions within said channel.

49. The apparatus of claim 46, wherein said base member further comprises a pinion gear having a plurality of gear teeth and said leg portion further comprising a rack having a plurality of mating teeth adapted to engage said gear teeth.

50. The apparatus of claim 46, wherein said base member further comprises a threaded shaft rotatably coupled to said base member, and said leg portion further comprises a collar having a threaded interior adapted to receive said threaded shaft.

51. The apparatus of claim 48, wherein said channel further comprises a plurality of teeth and said leg portion further comprises a plurality of mating teeth adapted to engage said teeth.

52. The apparatus of claim 41, wherein said leg portion is substantially flexible relative to said base member.

53. The apparatus of claim 52, wherein said wire frame is formed from a unitary length of wire material.

54. The apparatus of claim 53, wherein said wire material is selected from the group consisting of stainless steel and titanium.

55. The apparatus of claim 41, wherein said frame portion has a first end and a second end and said wire frame comprises a first leg portion attached to said first end and a second leg portion attached to said second end, said first and second leg portions being coupled to said base member.

56. The apparatus of claim 55, wherein said base portion further comprises a first channel and a second channel for slidably receiving said first leg portion and said second leg portion respectively.

57. The apparatus of claim 41, wherein said frame portion is vertically offset form said at least one contact area.

58. The apparatus of claim 57, wherein said vertical offset is between about 0.05 inches to about 0.2 inches.

59. The apparatus of claim 57, wherein said at least one contact area is substantially planar.

60. The apparatus of claim 41, wherein said at least one leg portion further comprises a vertically relieved portion.

61. The apparatus of claim 40, wherein said substantially rigid base member is formed from a unitary piece of sheet material having a first side and a second side, said base member having a first section adapted to contact the surface of the beating heart and a second section at a fixed angle to said first section, said first section defining a first contact surface, a second contact surface, and an open space therebetween; and said post is connected to said second section at a location which is offset from said open space.

62. The apparatus of claim 61, further including a delivery stem having a proximal end and a distal end having a socket operably engaged with said ball-shaped member.

63. The apparatus of claim 61, wherein said delivery stem is curved.

64. The apparatus of claim 60, wherein said delivery stem is a shaft.

65. The apparatus of claim 61, wherein said angle is from about 75 degrees to about 105 degrees.

66. The apparatus of claim 65, wherein said angle is about 90 degrees.

67. The apparatus of claim 66, wherein said post extends from said first side.

68. The apparatus of claim 61, wherein said angle is more than about 120 degrees and said post extends from said second side.

69. The apparatus of claim 40, further comprising a delivery stem having a proximal end and a distal end, said distal end having a socket operably engaged with said ball-shaped member.

70. The apparatus of claim 40, wherein said delivery stem is substantially rigid.

71. The apparatus of claim 40, wherein said base member has a first section having at least one surface for contacting the surface of a heart and a second section adjacent said first section, said post being moveably coupled to said second section.

72. The apparatus of claim 71, wherein said second section is at an angle relative to said first section.

73. The apparatus of claim 71, wherein said second section has a slot adapted to receive said first end of said post, said first end being moveable within said slot from a first position to a second position.

74. The apparatus of claim 40, wherein at least a portion of said base member has a curved outer profile and said post is mounted to a top member having an interior profile adapted to engage and concentrically rotate about said curved outer profile.

75. The apparatus of claim 74, wherein said base member has at least one elongate slot and said top member has at least one tab engaged within said at least one slot.

76. The apparatus of claim 40, further comprising:

a link member pivotably coupled to said base member at a predetermined pivot point, said link member having a first link end spaced a distance away from said pivot point, and said post being moveably coupled to said base member by a first post end attached to said first link end.

77. The apparatus of claim 76, further comprising a delivery stem having a proximal end and a distal end, said distal end having a socket operably engaged with said ball shaped member.

78. The apparatus of claim 77, wherein said delivery stem is substantially rigid.

79. The apparatus of claim 76, wherein said link member has a second link end opposite said first link end, said second link end being releasably locked to said base member to substantially prevent relative movement of said link member relative to said base member.

80. The apparatus of claim 76, wherein said link member pivots about a pivot pin extending from said base member.

81. The apparatus of claim 80, wherein said base member has a first contact surface, a second contact surface, and an open space therebetween.

82. The apparatus of claim 81, wherein said link member has a first position wherein said post is offset from said open space in a first direction and a second position wherein said post is offset from said open space in a second direction.

\* \* \* \* \*

UNITED STATES PATENT AND TRADEMARK OFFICE
CERTIFICATE OF CORRECTION

PATENT NO. : 6,685,632 B1
DATED : February 3, 2004
INVENTOR(S) : Hu et al.

It is certified that error appears in the above-identified patent and that said Letters Patent is hereby corrected as shown below:

Title page,
Item [62], Related U.S. Application Data, delete "Continuation-in-part of application 09/372,661 filed on May 4, 1999, now abandoned, and a continuation-in-part of application No. 09/305,803, filed May 4, 1999, now Pat. No. 6,231,506, and a continuation-in-part of application No. 09/305,810, filed on May 4, 1999, now Pat. No. 6,331,158, and a continuation-in-part of application No. 09/305,811 filed on May 4, 1999, now Pat. No. 6,283,912, and a continuation-in-part of application No. 09/305,813, filed on May 4, 1999, now Pat. No. 6,290,644, which is a continuation-in-part of application No. 09/305,810, filed on May 4, 1999, now Pat. No. 6,331,158," and insert therefore -- this application is a 35 USC 371 of PCTUS00/12239 filed May 4, 2000, which is a continuation in part of U.S. application Serial No. 09/305,803, filed May 4, 1999, now U.S. Patent No. 6,231,506; and a continuation in part of U.S. application Serial No. 09/305,810, filed May 4, 1999, now U.S.Patent No. 6,331,158; and a continuation in part of U.S. application Serial No. 09/305,811, filed May 4, 1999, now U.S. Patent No. 6,283,912; and a continuation in part of U.S. application Serial No. 09/305,813, filed May 4, 1999, now U.S. Pat. No. 6,290,644; and a continuation in part of U.S. application Serial No. 09/372,661, filed May 4, 1999, now abandoned; which is a continuation in part of U.S. application Serial No. 09/305,810, filed May 4, 1999, now U.S. Patent No. 6,331,158 --.

Column 37,
Line 39, delete "said'" and insert therefore -- said --.

Column 38,
Line 7, delete "frustoconical," and insert therefore -- frustoconical --

UNITED STATES PATENT AND TRADEMARK OFFICE
CERTIFICATE OF CORRECTION

PATENT NO.    : 6,685,632 B1
DATED         : February 3, 2004
INVENTOR(S)   : Hu et al.

It is certified that error appears in the above-identified patent and that said Letters Patent is hereby corrected as shown below:

Column 39,
Line 39, delete "first-direction" and insert therefore -- first direction --.

Signed and Sealed this

Nineteenth Day of July, 2005

JON W. DUDAS
*Director of the United States Patent and Trademark Office*